United States Patent
Kim et al.

(10) Patent No.: US 11,778,909 B2
(45) Date of Patent: Oct. 3, 2023

(54) COMPOUND AND ORGANIC LIGHT EMITTING DEVICE COMPRISING THE SAME

(71) Applicant: LG CHEM, LTD., Seoul (KR)

(72) Inventors: Sunmin Kim, Daejeon (KR); Yongbum Cha, Daejeon (KR); Sang Young Jeon, Daejeon (KR); Yeon Hwan Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 596 days.

(21) Appl. No.: 16/964,723

(22) PCT Filed: May 2, 2019

(86) PCT No.: PCT/KR2019/005993
§ 371 (c)(1),
(2) Date: Jul. 24, 2020

(87) PCT Pub. No.: WO2019/212325
PCT Pub. Date: Nov. 7, 2019

(65) Prior Publication Data
US 2020/0358006 A1   Nov. 12, 2020

(30) Foreign Application Priority Data

May 3, 2018  (KR) .................. 10-2018-0051361

(51) Int. Cl.
*H01L 51/00* (2006.01)
*C07D 251/24* (2006.01)
(Continued)

(52) U.S. Cl.
CPC ....... *H10K 85/6572* (2023.02); *C07D 239/26* (2013.01); *C07D 251/24* (2013.01);
(Continued)

(58) Field of Classification Search
None
See application file for complete search history.

(56) References Cited

U.S. PATENT DOCUMENTS

2004/0251816 A1   12/2004   Leo et al.
2009/0092853 A1   4/2009    Park et al.
(Continued)

FOREIGN PATENT DOCUMENTS

| CN | 108117508 | 6/2018 |
| CN | 108117511 | 6/2018 |

(Continued)

OTHER PUBLICATIONS

Machine English translation of Kim et al. (KR 10-2017-0095602). Feb. 27, 2023.*

*Primary Examiner* — Jay Yang
(74) *Attorney, Agent, or Firm* — Bryan Cave Leighton Paisner LLP

(57) ABSTRACT

Provided is a compound of Chemical Formula 1:

[Chemical Formula 1]

(Continued)

wherein:
  L is a single bond, a substituted or unsubstituted $C_{6-60}$ arylene, or a substituted or unsubstituted $C_{2-60}$ heteroarylene containing at least one selected from the group consisting of N, O and S, and
  Ar is a substituted or unsubstituted $C_{2-60}$ heteroaryl containing at least one selected from the group consisting of N, O and S,
and to an organic light emitting device comprising the same.

9 Claims, 1 Drawing Sheet

(51) Int. Cl.
  *C07D 239/26* (2006.01)
  *C07D 405/04* (2006.01)
  *C07D 409/04* (2006.01)
  *H10K 85/60* (2023.01)
  *H10K 50/18* (2023.01)
(52) U.S. Cl.
  CPC ......... *C07D 405/04* (2013.01); *C07D 409/04* (2013.01); *H10K 85/624* (2023.02); *H10K 85/626* (2023.02); *H10K 85/6574* (2023.02); *H10K 85/6576* (2023.02); *H10K 50/18* (2023.02)

(56) References Cited

U.S. PATENT DOCUMENTS

| | | |
|---|---|---|
| 2013/0328021 A1 | 12/2013 | Lim et al. |
| 2014/0014916 A1 | 1/2014 | Han et al. |
| 2014/0306190 A1 | 10/2014 | Lee et al. |

FOREIGN PATENT DOCUMENTS

| | | |
|---|---|---|
| KR | 10-2000-0051826 | 8/2000 |
| KR | 10-2009-0035974 | 4/2009 |
| KR | 10-2013-0139105 | 12/2013 |
| KR | 10-2014-0008213 | 1/2014 |
| KR | 10-2014-0124029 | 10/2014 |
| KR | 10-2017-0095602 | 8/2017 |
| KR | 10-2018-0045695 | 5/2018 |
| WO | 2003-012890 | 2/2003 |

\* cited by examiner

[FIG. 1]
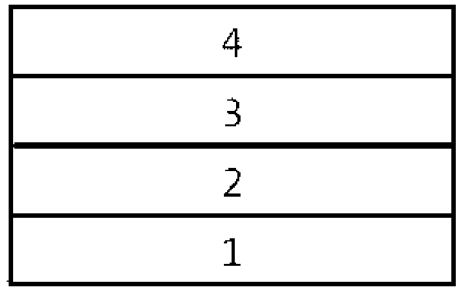
[FIG. 2]
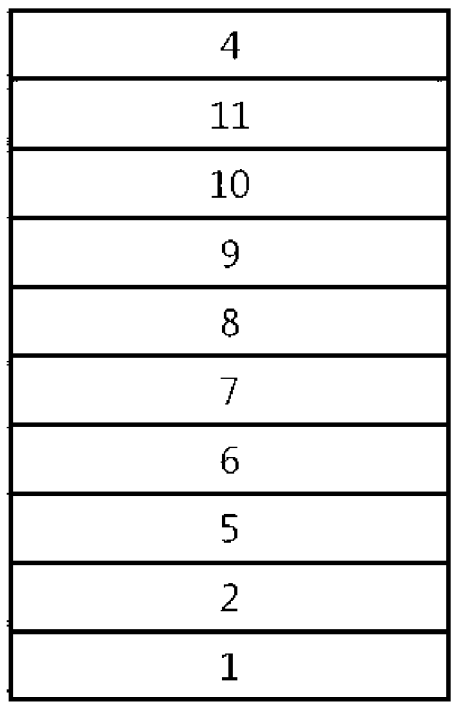

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/005993 filed on May 2, 2019, which claims the benefit of the filing date of Korean Patent Application No. 10-2018-0051361 filed with Korean Intellectual Property Office on May 3, 2018, the entire content of which is incorporated herein by reference.

TECHNICAL FIELD

The present invention relates to a novel compound and to an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE

Patent Literature (Patent Literature 0001) Korean Patent Laid-open Publication No. 10-2000-0051826

BRIEF DESCRIPTION

Technical Problem

It is an object of the present invention to provide a novel compound and an organic light emitting device including the same.

Technical Solution

In one aspect of the invention, there is provided a compound of Chemical Formula 1:

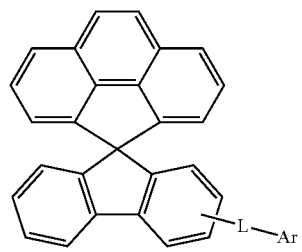

Chemical Formula 1 wherein in Chemical Formula 1:

L is a single bond, a substituted or unsubstituted $C_{6-60}$ arylene, or a substituted or unsubstituted $C_{2-60}$ heteroarylene containing at least one selected from the group consisting of N, O and S; and Ar is a substituted or unsubstituted $C_{2-60}$ heteroaryl containing at least one selected from the group consisting of N, O and S.

In another aspect of the invention, provided is an organic light emitting device including a first electrode; a second electrode provided opposite to the first electrode; and one or more organic material layers provided between the first electrode and the second electrode, wherein one or more layers of the organic material layers includes the compound of Chemical Formula 1.

Advantageous Effects

The compound of Chemical Formula 1 described above can be used as a material of an organic material layer of an organic light emitting device, and can improve the efficiency, achieve low driving voltage and/or improve lifetime characteristics in the organic light emitting device. In particular, the compound of Chemical Formula 1 described above can be used as a material for hole injection, hole transport, hole injection and transport, light emitting, electron transport, or electron injection.

BRIEF DESCRIPTION OF DRAWINGS

FIG. 1 shows an example of an organic light emitting device comprising a substrate 1, an anode 2, an organic material layer 3, and a cathode 4.

FIG. 2 shows an example of an organic light emitting device comprising a substrate 1, an anode 2, a hole injection layer 5, a hole transport layer 6, an electron blocking layer 7, a light emitting layer 8, a hole blocking layer 9, an electron transport layer 10, an electron injection layer 11, and a cathode 4.

DETAILED DESCRIPTION

Hereinafter, the present invention will be described in more detail to help understanding of the present invention.

In one embodiment of the invention, provided is a compound of Chemical Formula 1.

As used herein, the notation, ⊢ or ⊣ means a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a hetero-cyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group, and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulae, but is not limited thereto:

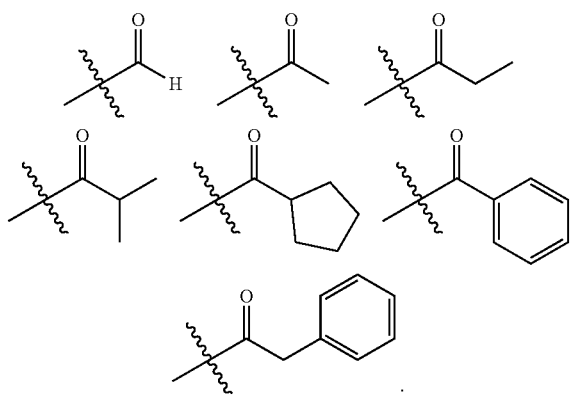

In the present specification, for an ester group, the oxygen of the ester group can be substituted with a straight-chain, branched-chain, or cyclic alkyl group having 1 to 25 carbon atoms, or an aryl group having 6 to 25 carbon atoms. Specifically, the ester group can be a compound having the following structural formulae, but is not limited thereto:

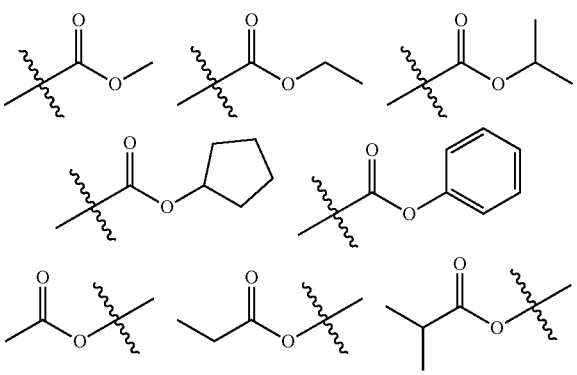

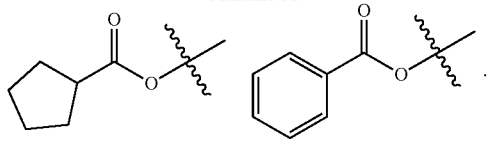

In the present specification, the number of carbon atoms of an imide group is not particularly limited, but is preferably 1 to 25. Specifically, the imide group can be a compound having the following structural formulae, but is not limited thereto:

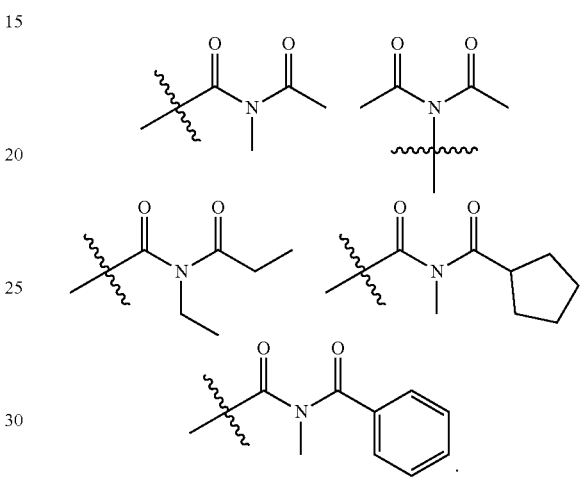

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group can be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethyl-cyclopentyl, cyclohexyl, 3-methylcyclohexyl, 4-methylcyclohexyl, 2,3-dimethyl-cyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group can be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group and a fluorenyl group or the like, but is not limited thereto.

In the present specification, a fluorenyl group can be substituted, and two substituent groups can be bonded to each other to form a spiro structure. In the case where the fluorenyl group is substituted,

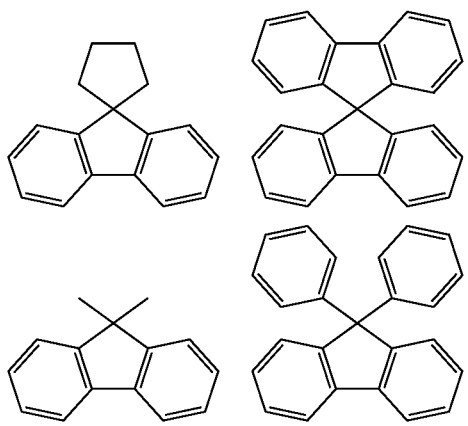

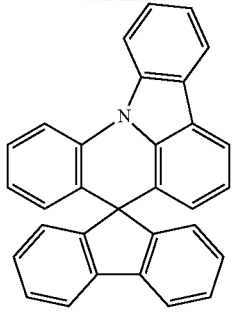

and the like can be formed. However, the structure is not limited thereto.

In the present specification, a heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

Preferably, Chemical Formula 1 is one of the following Chemical Formula 1-1, 1-2 or 1-3:

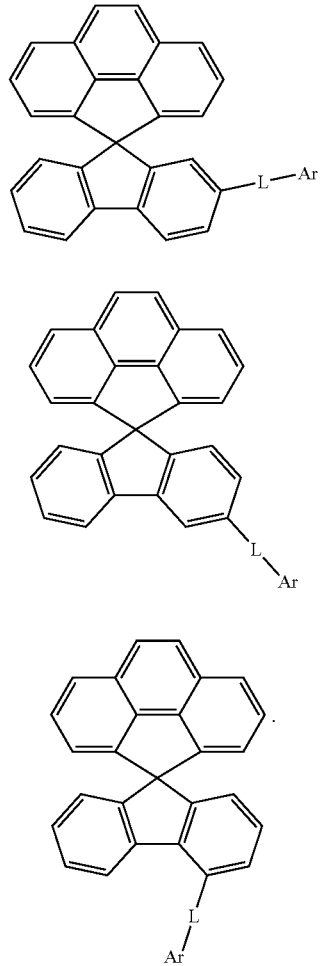

Chemical Formula 1-1

Chemical Formula 1-2

Chemical Formula 1-3

Preferably, L is a single bond, phenylene, or carbazoldiyl. More preferably, L is a single bond, 1,4-phenylene, 1,3-phenylene, 1,2-phenylene, or

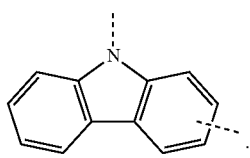

Preferably, Ar is any one selected from the group consisting of the following:

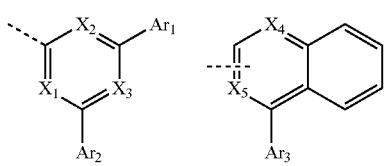

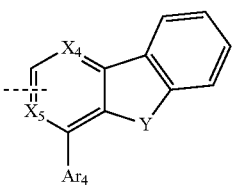

wherein:

$X_1$ to $X_3$ are N, or CH, with the proviso that at least one of $X_1$ to $X_3$ is N;

$Ar_1$ and $Ar_2$ are each independently a substituted or unsubstituted $C_{6-60}$ aryl or a substituted or unsubstituted $C_{2-60}$ heteroaryl containing at least one selected from the group consisting of N, O and S;

$X_4$ and $X_5$ are N, or CH, with the proviso that at least one of $X_4$ and $X_5$ is N;

$Ar_3$ is independently a substituted or unsubstituted $C_{6-60}$ aryl or a substituted or unsubstituted $C_{2-60}$ heteroaryl containing at least one selected from the group consisting of N, O and S;

Y is $N(Ar_5)$, O or S;

$Ar_4$ is hydrogen, a substituted or unsubstituted $C_{6-60}$ aryl, or a substituted or unsubstituted $C_{2-60}$ heteroaryl containing at least one selected from the group consisting of N, O and S; and $Ar_5$ is a substituted or unsubstituted $C_{6-60}$ aryl.

Preferably, $Ar_1$ and $Ar_2$ are each independently phenyl, biphenylyl, terphenylyl, naphthyl, phenanthrenyl, triphenylenyl, dibenzofuranyl, dibenzo-thiophenyl, or 9-phenyl-9H-carbazolyl.

Preferably, $Ar_3$ is phenyl, biphenylyl, or naphthyl.

Preferably, $Ar_4$ is hydrogen, phenyl, biphenylyl, or naphthyl.

Preferably, $Ar_5$ is phenyl.

Representative examples of the compound of Chemical Formula 1 are the following:

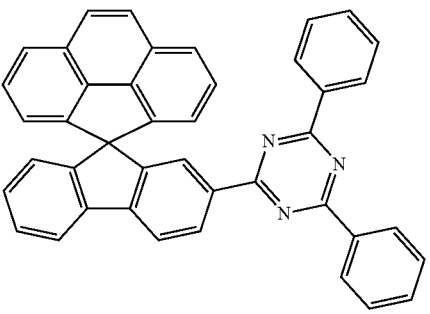

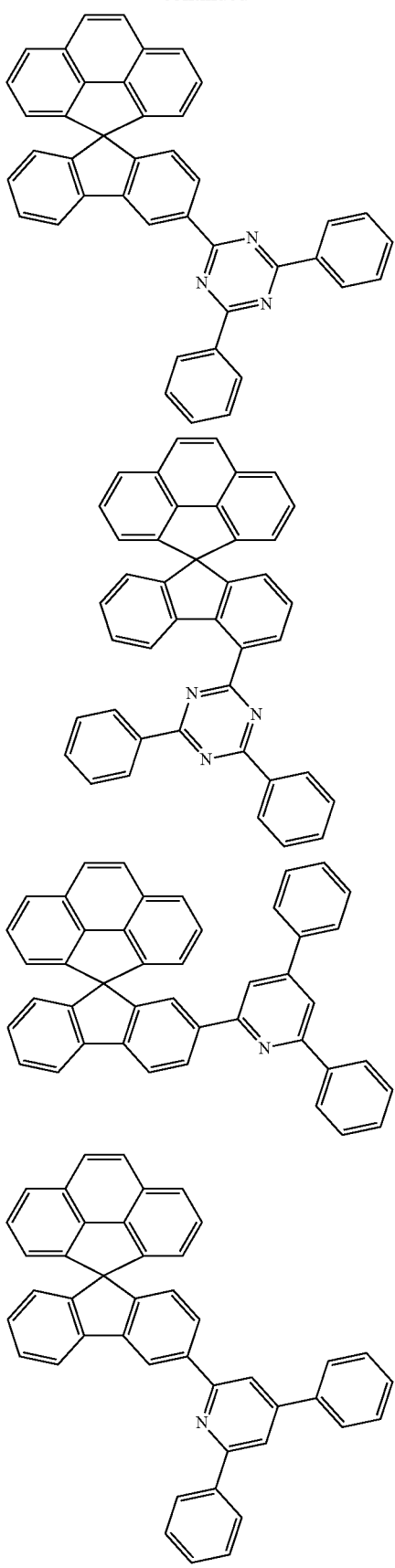
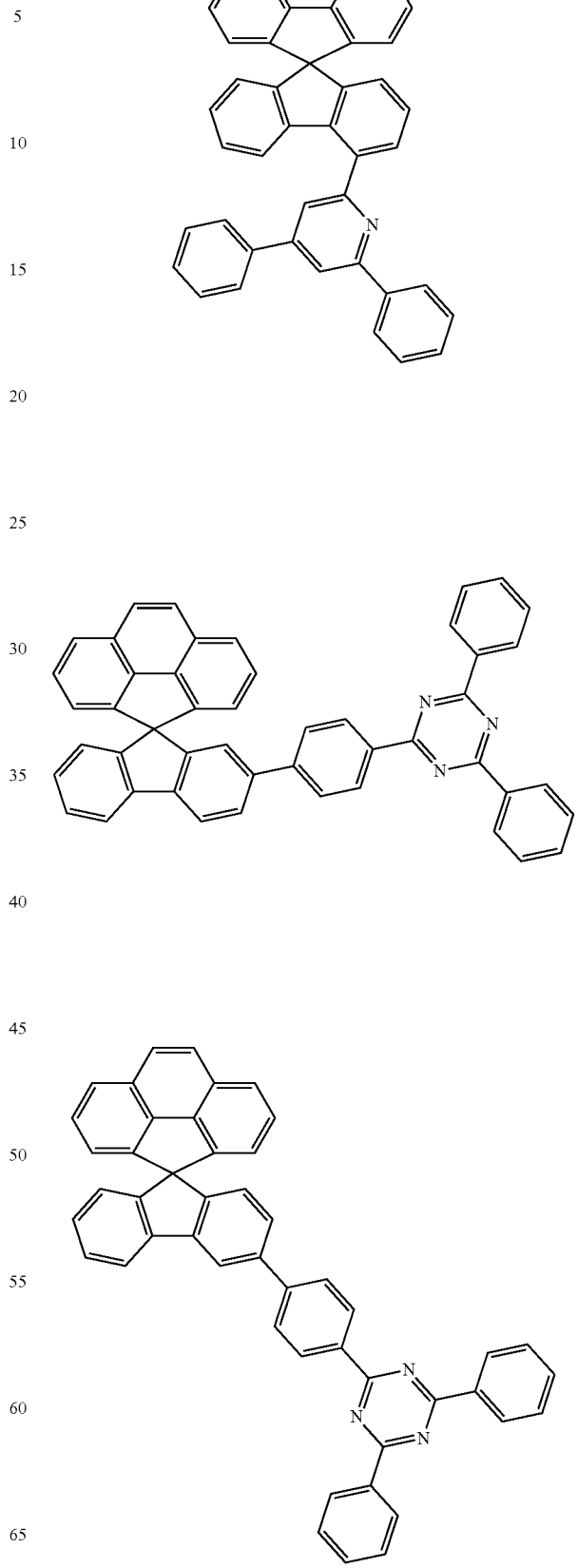

-continued
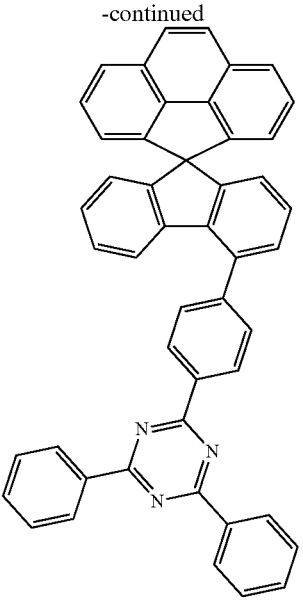
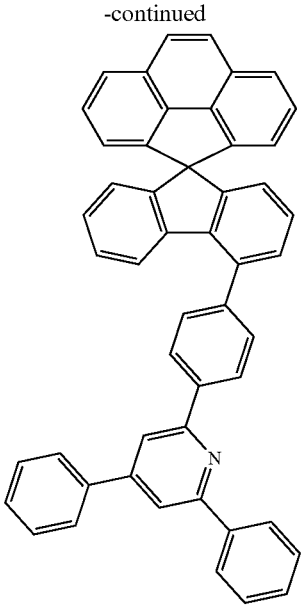
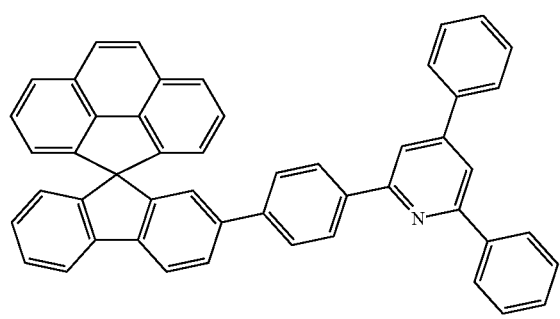
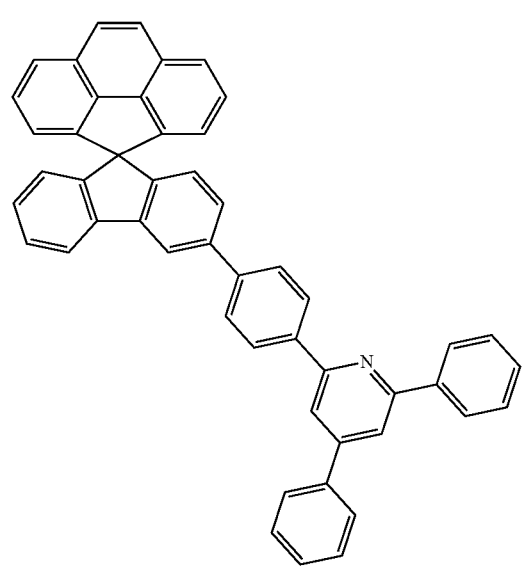
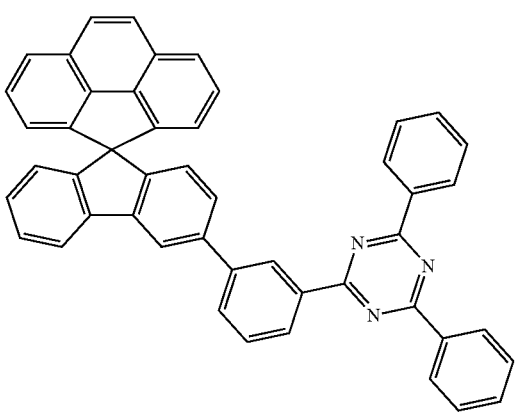

13
-continued
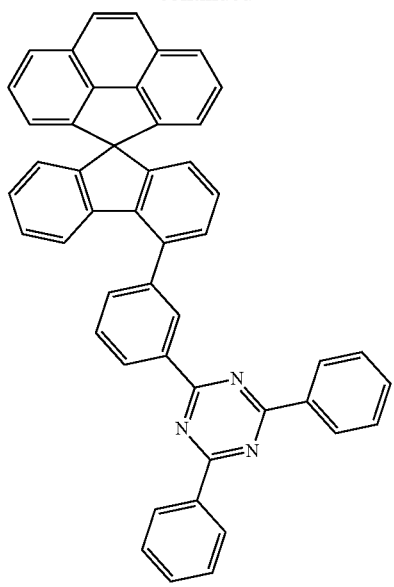
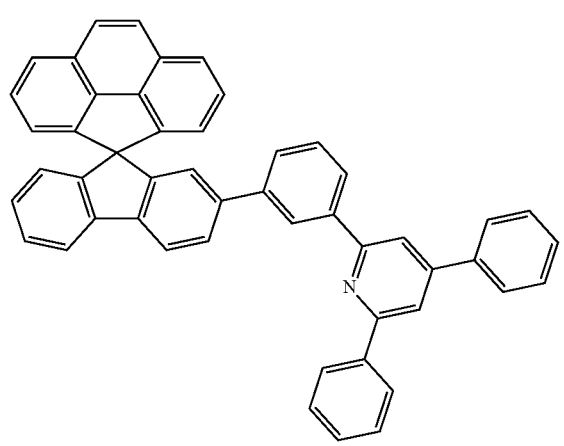
14
-continued
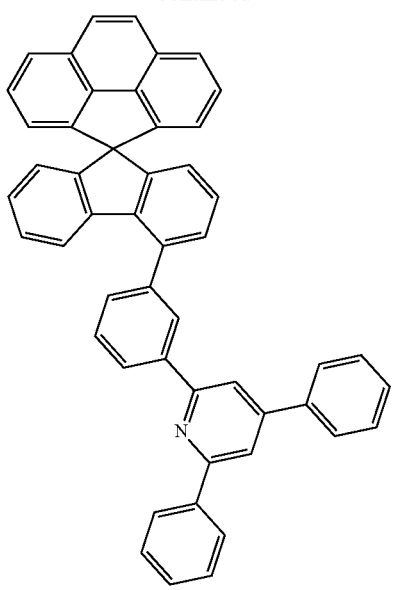
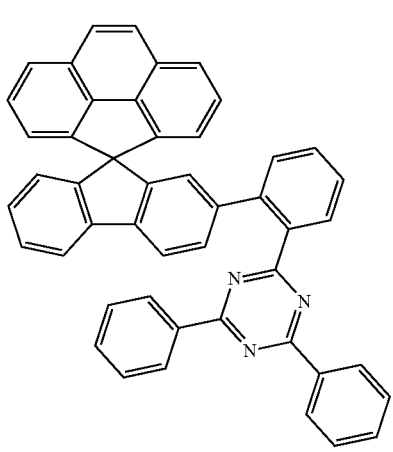
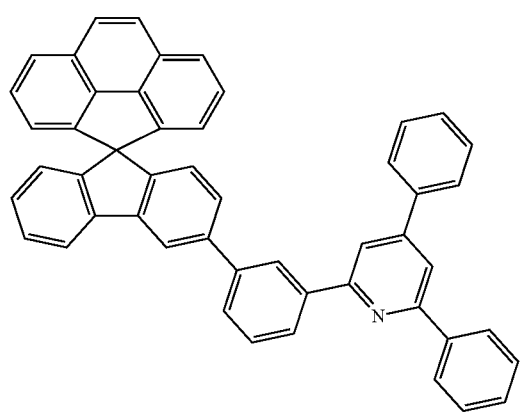
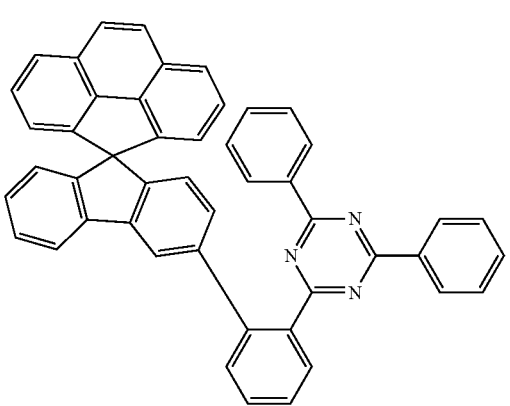

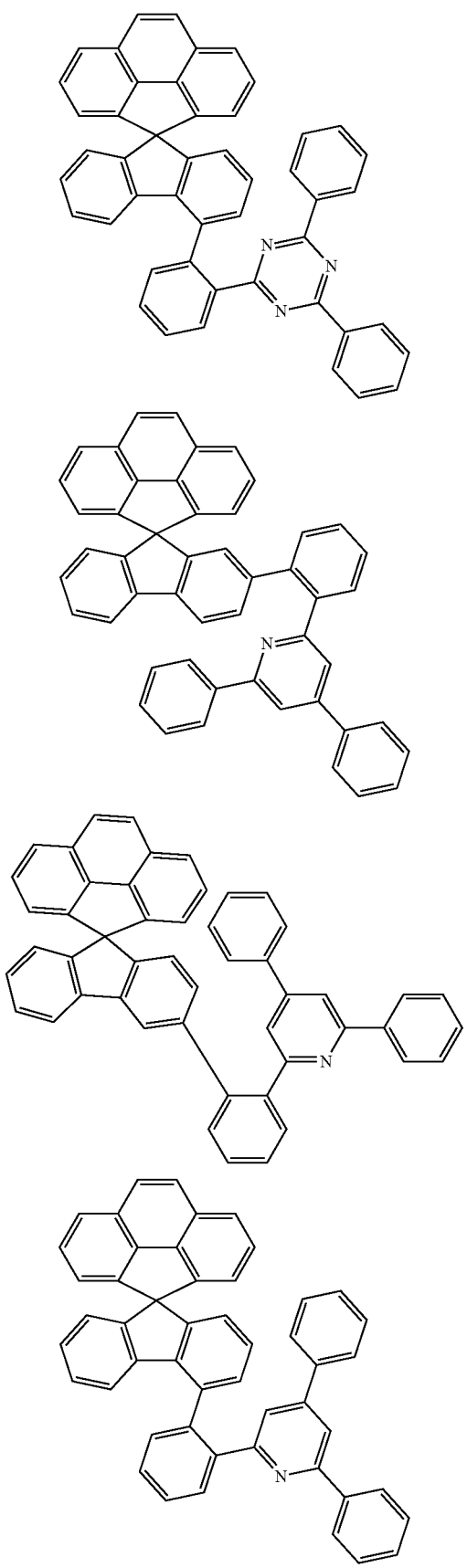 [SMILES: c1ccc(-c2nc(-c3ccccc3)nc(-c3ccccc3-c3cccc4c3-c3ccccc3C43c4cccc5ccc6cccc3c6c45)n2)cc1 ; c1ccc(-c2cc(-c3ccccc3)nc(-c3ccccc3-c3ccc4c(c3)C3(c5ccccc5-4)c4cccc5ccc6cccc3c6c45)c2)cc1 ; c1ccc(-c2cc(-c3ccccc3)nc(-c3ccccc3-c3ccc4c(c3)-c3ccccc3C43c4cccc5ccc6cccc3c6c45)c2)cc1 ; c1ccc(-c2cc(-c3ccccc3)nc(-c3ccccc3-c3cccc4c3-c3ccccc3C43c4cccc5ccc6cccc3c6c45)c2)cc1]
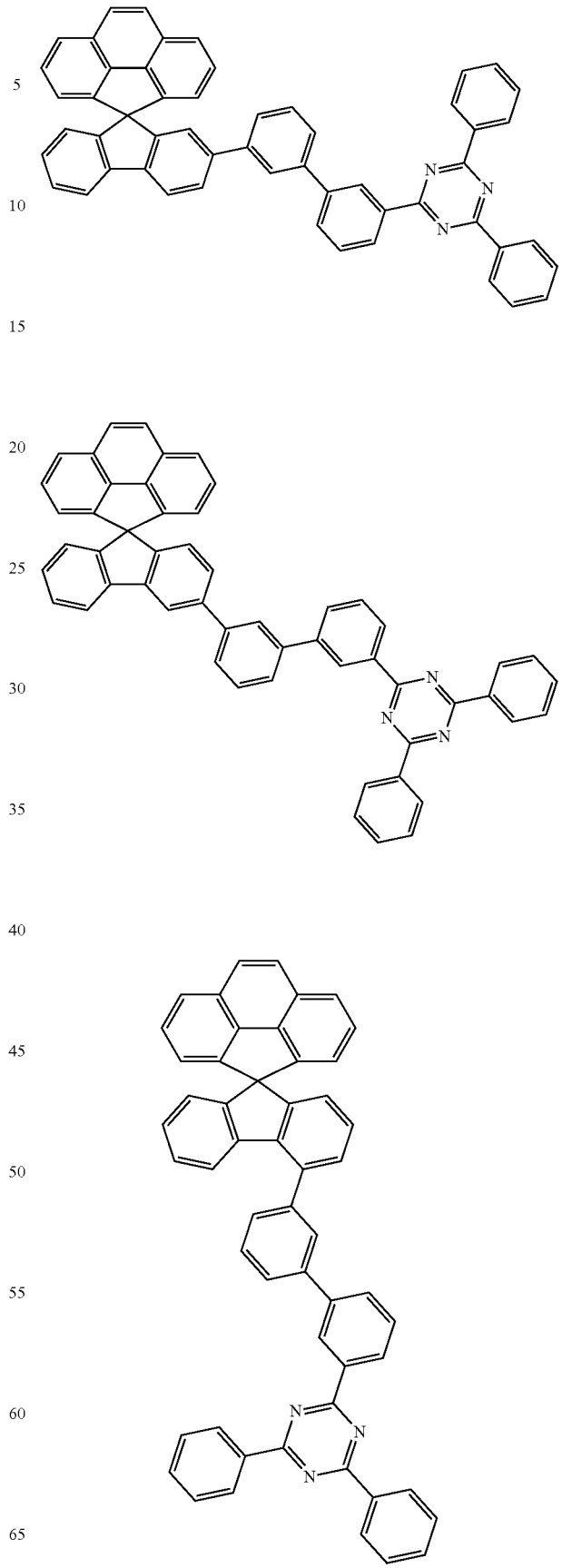

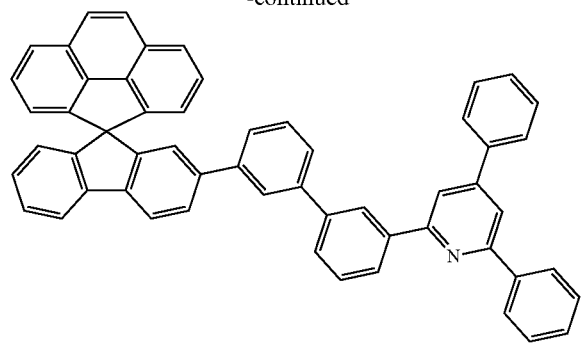
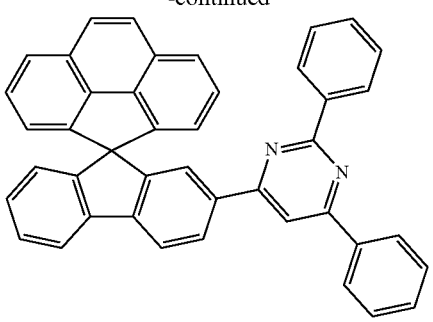

19
-continued
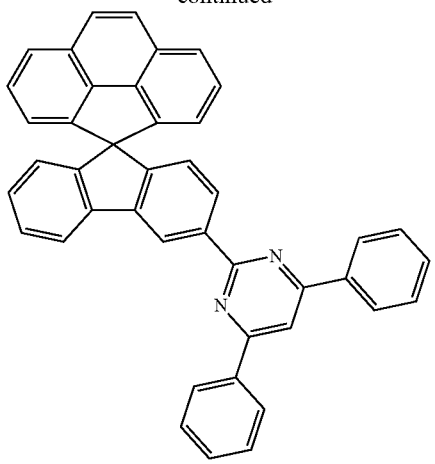
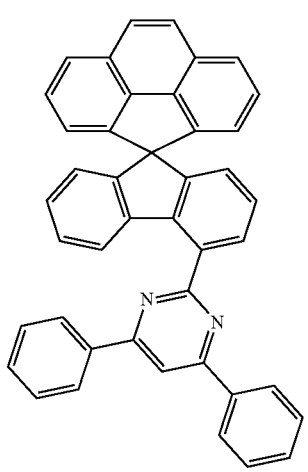
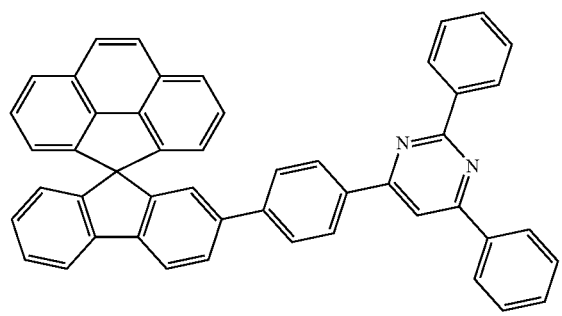
20
-continued
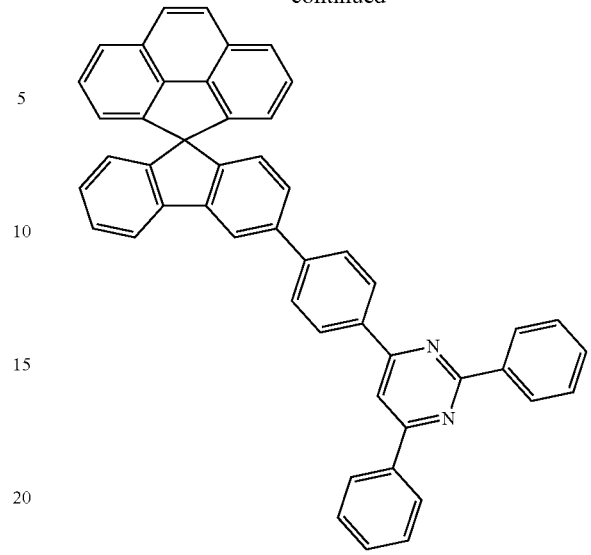
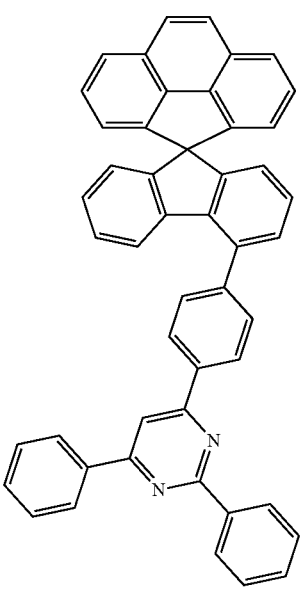
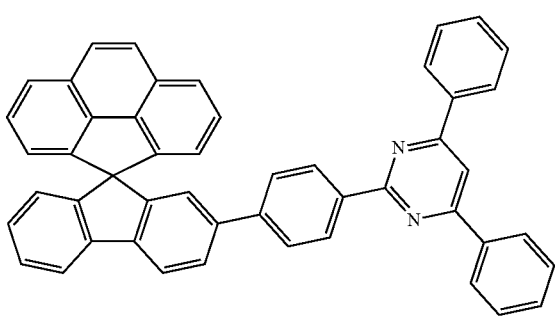

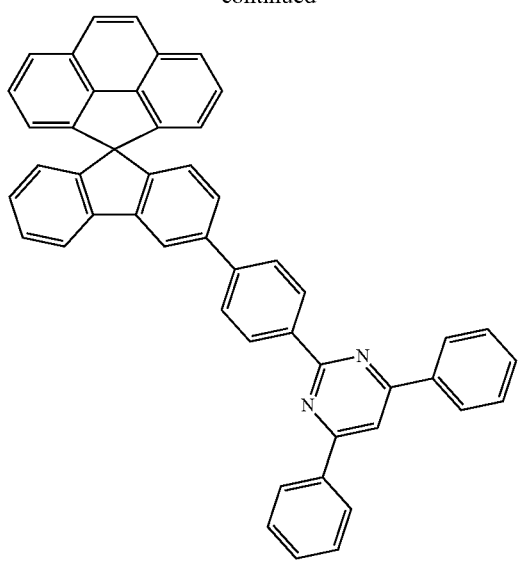
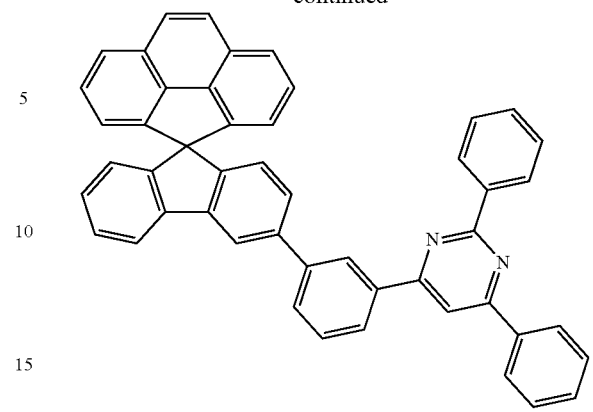
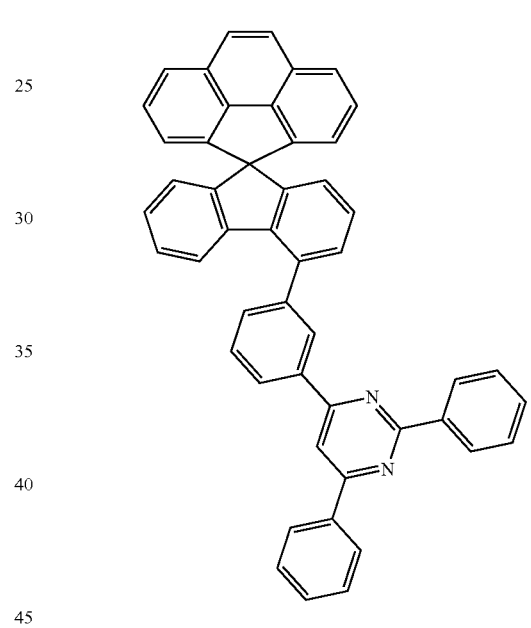
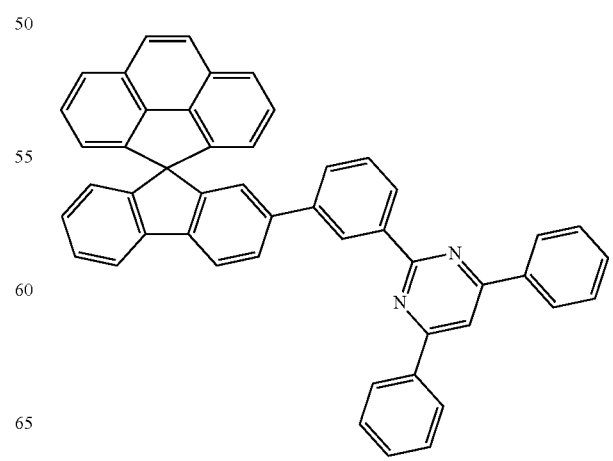

23
-continued
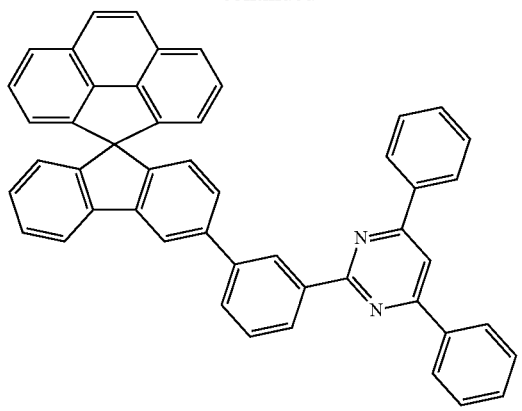
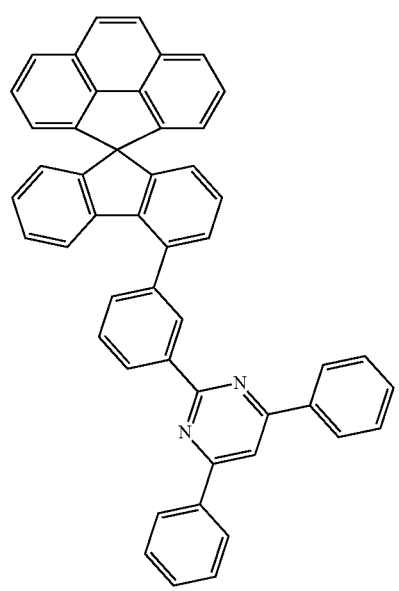
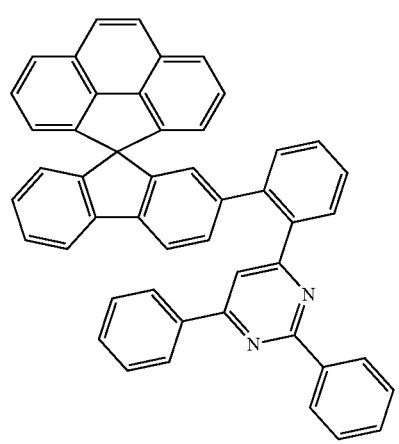
24
-continued
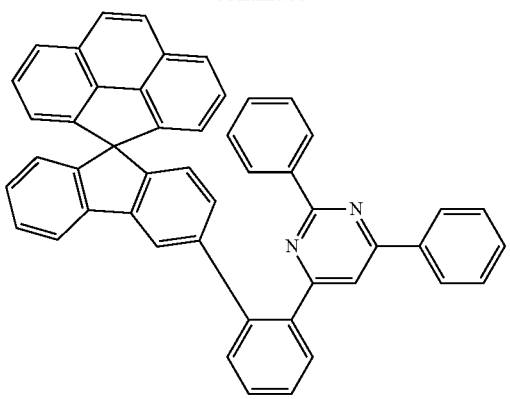
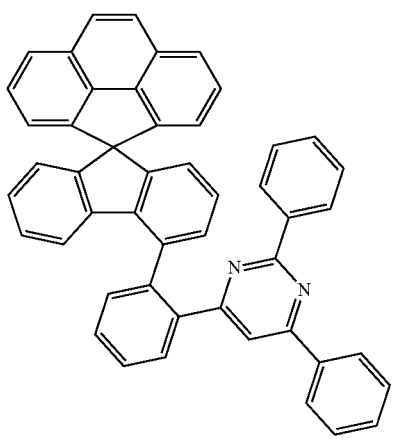
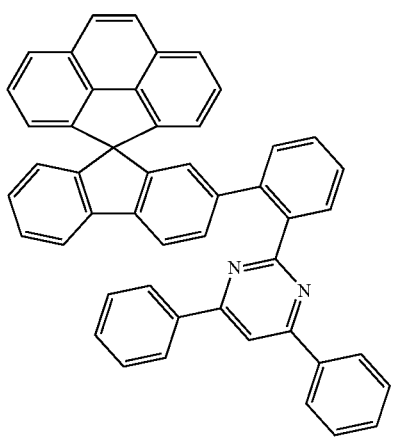
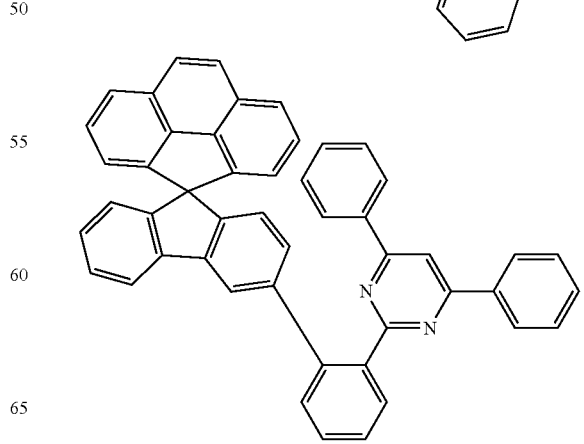

25
-continued
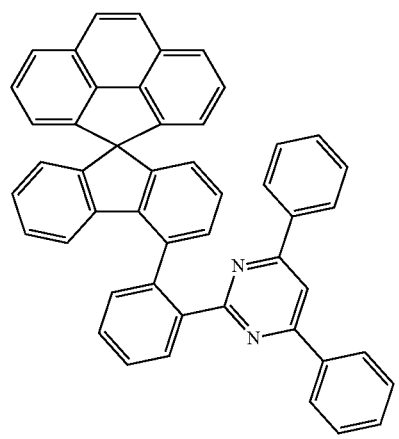
26
-continued
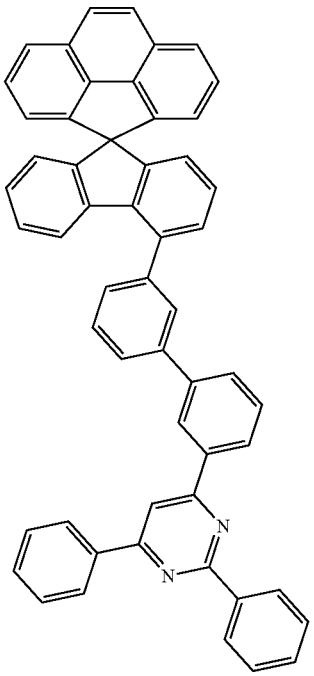
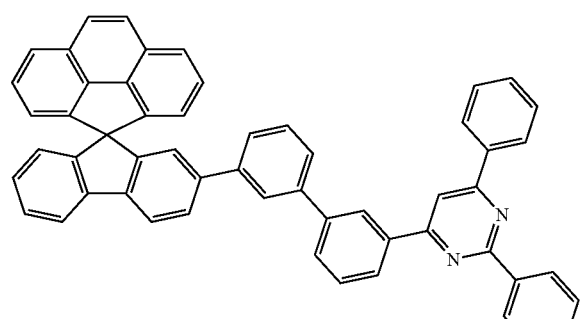
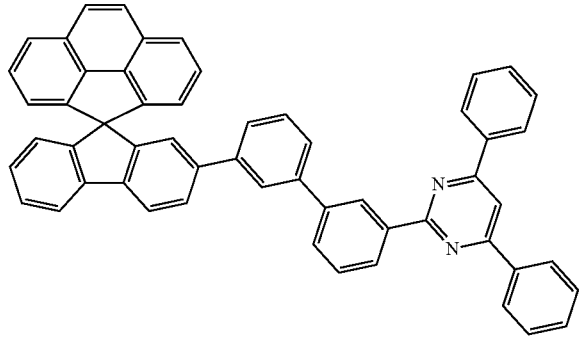
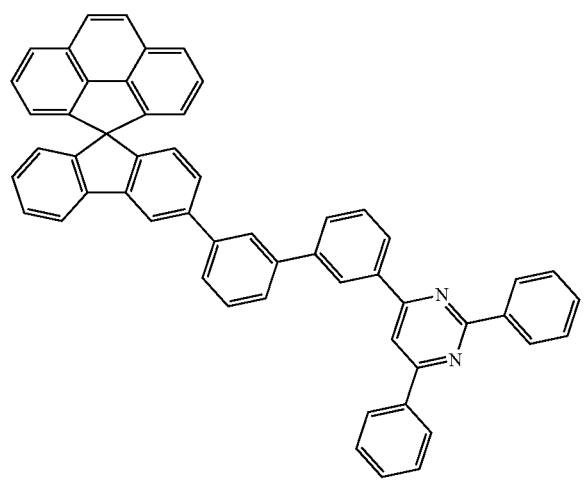
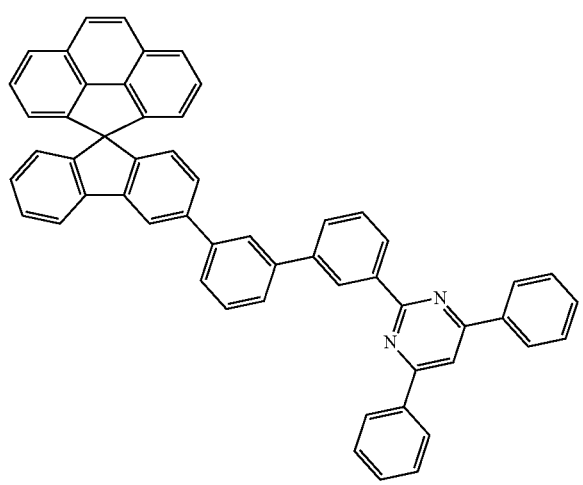

27
-continued
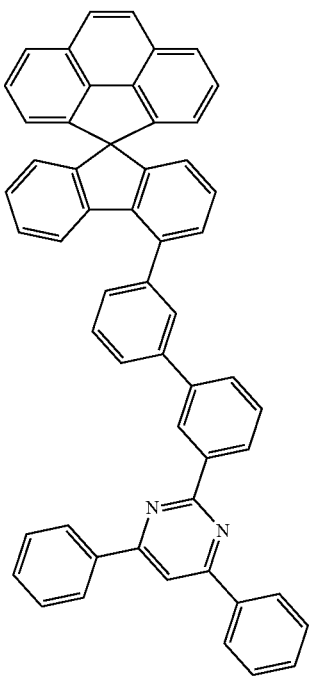
28
-continued
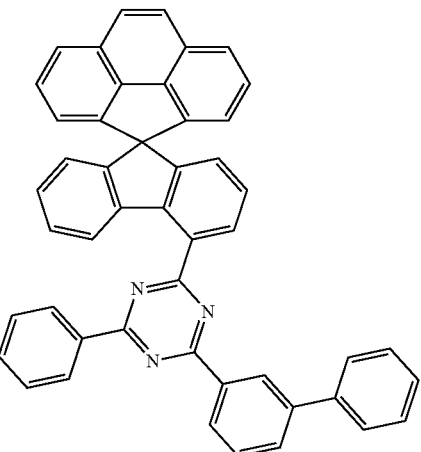
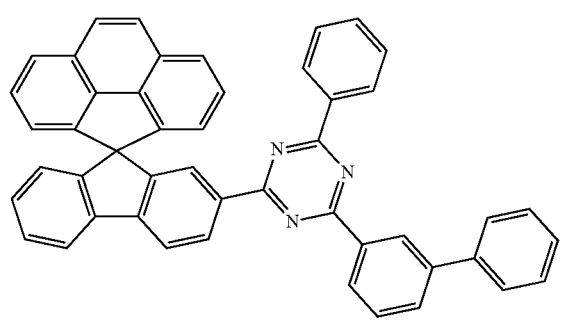
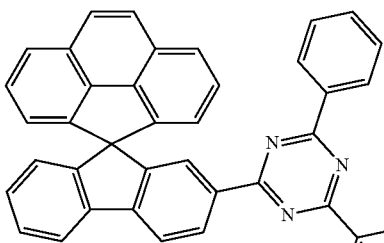
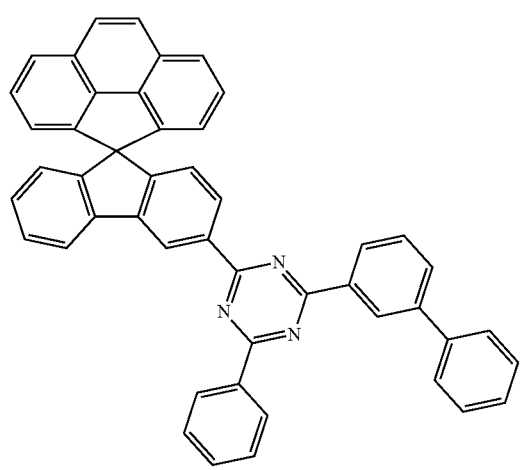
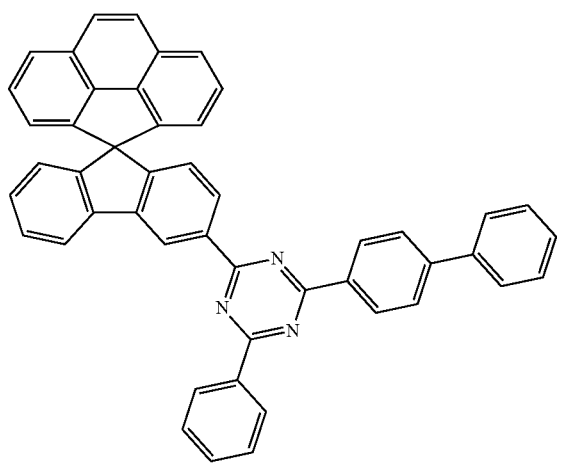

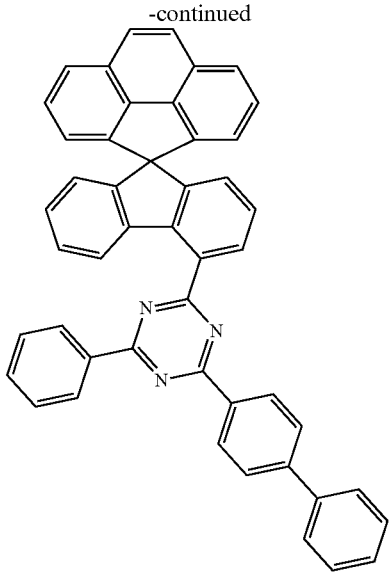
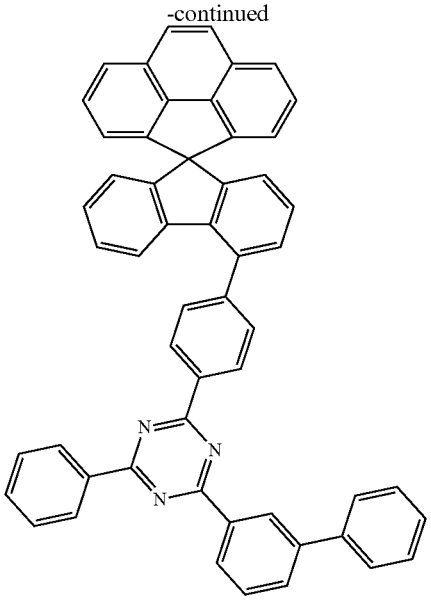
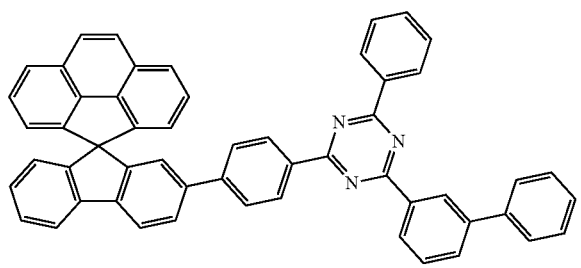
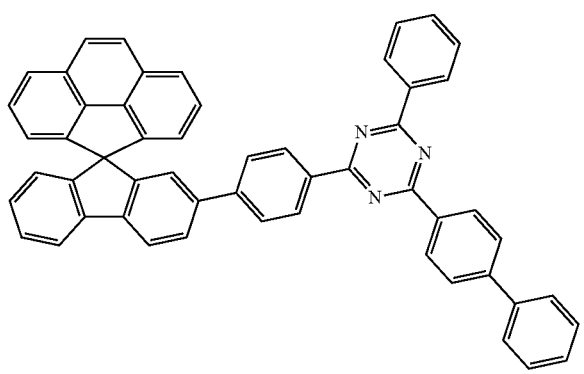
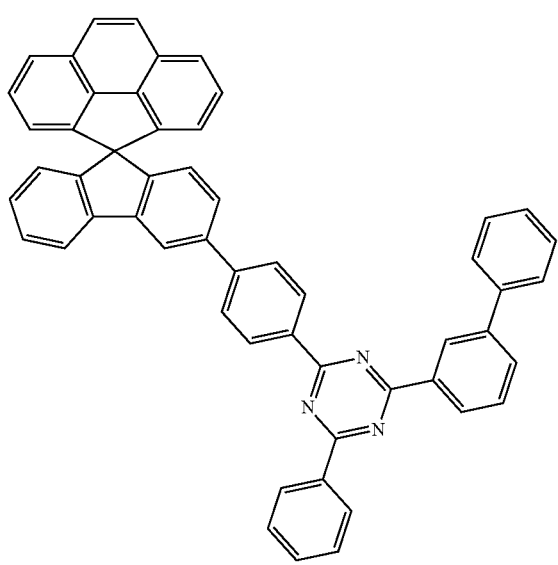
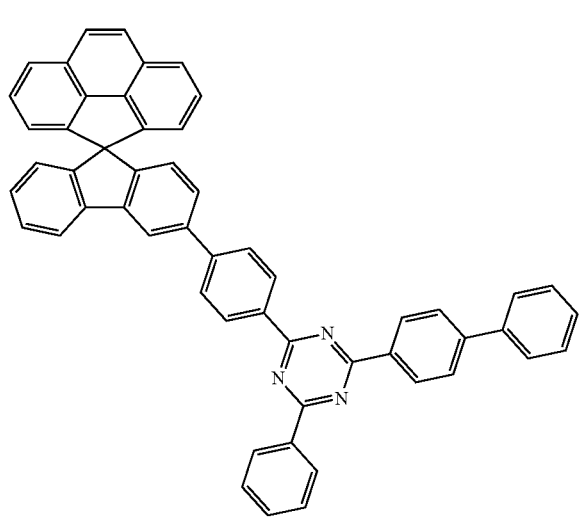

31
-continued
32
-continued
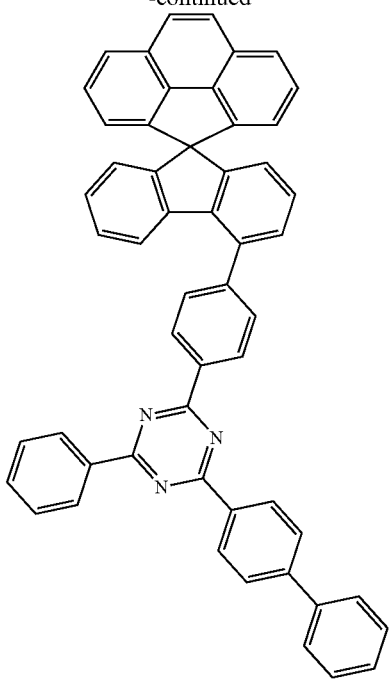
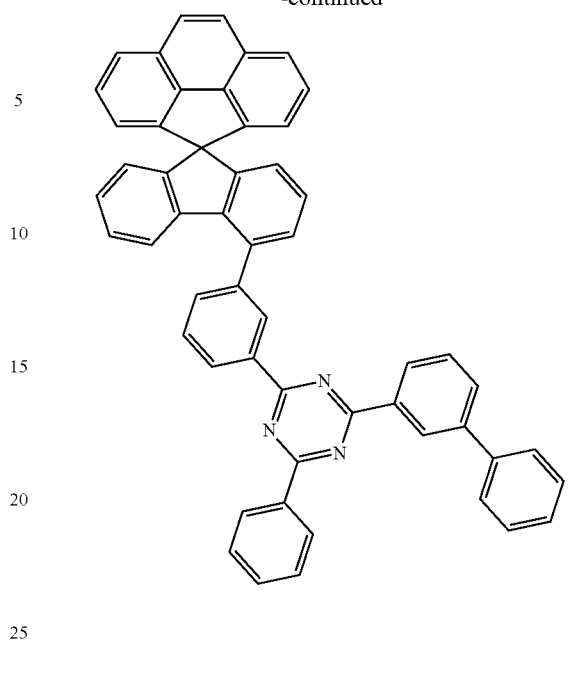
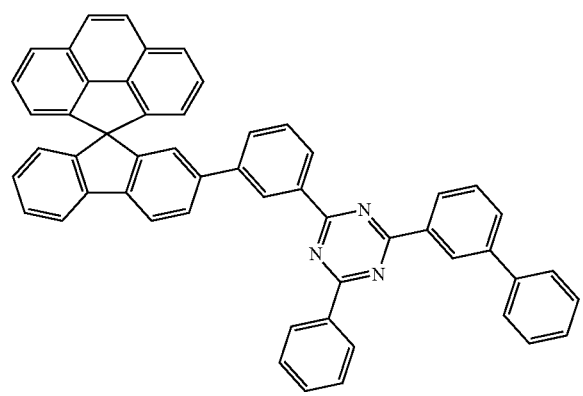
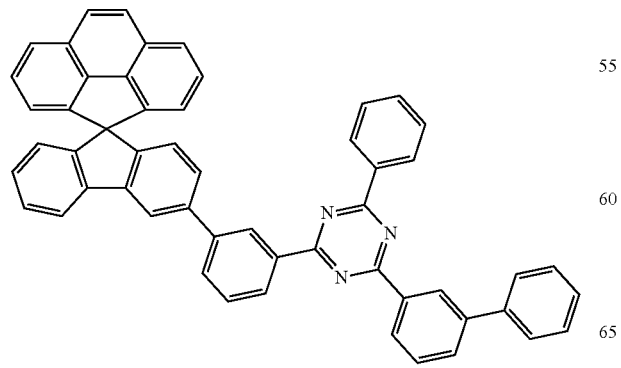

33
-continued
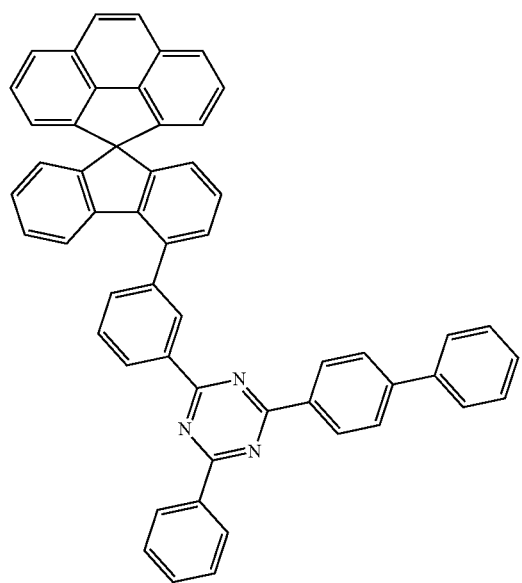
34
-continued
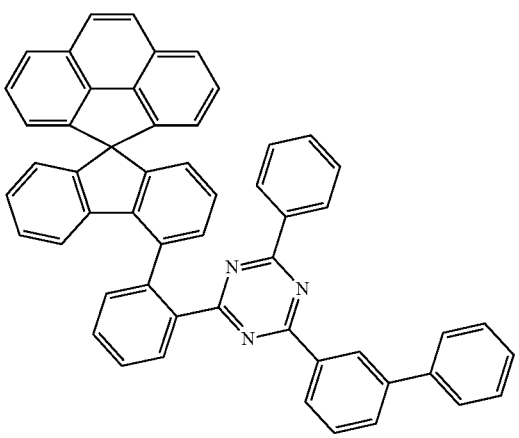
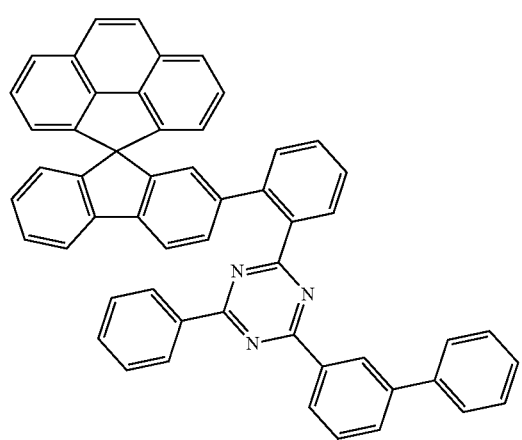
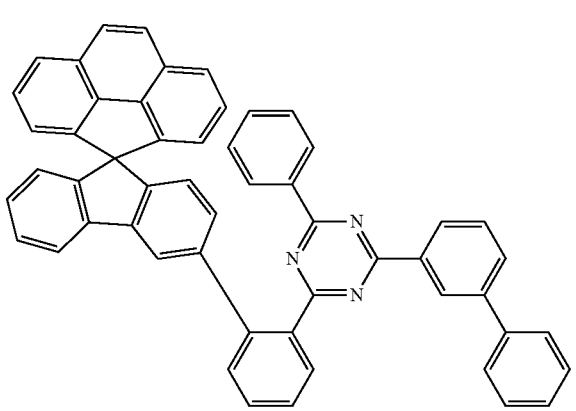
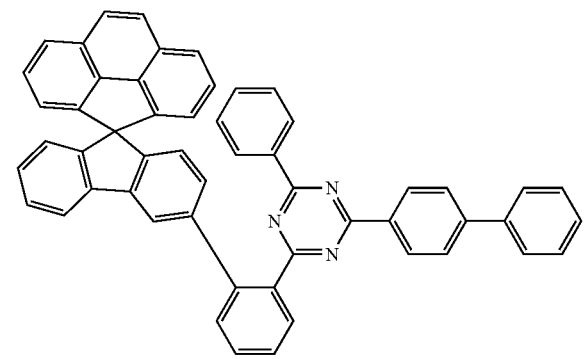

35
-continued
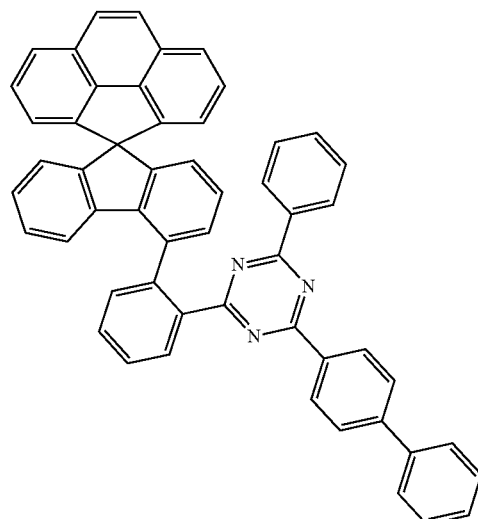
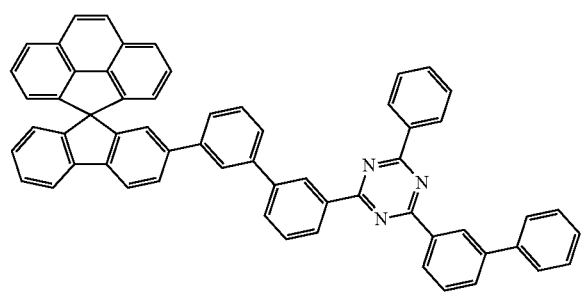
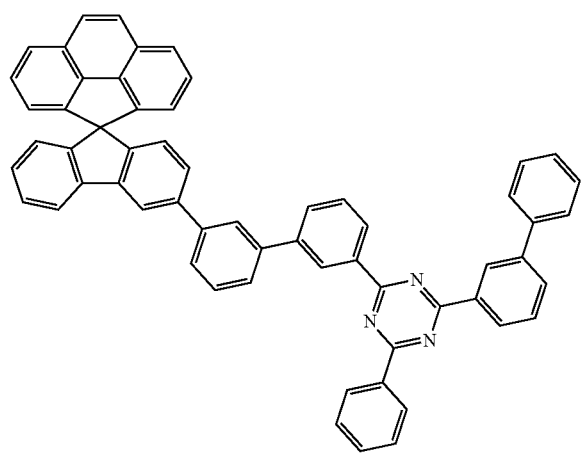
36
-continued
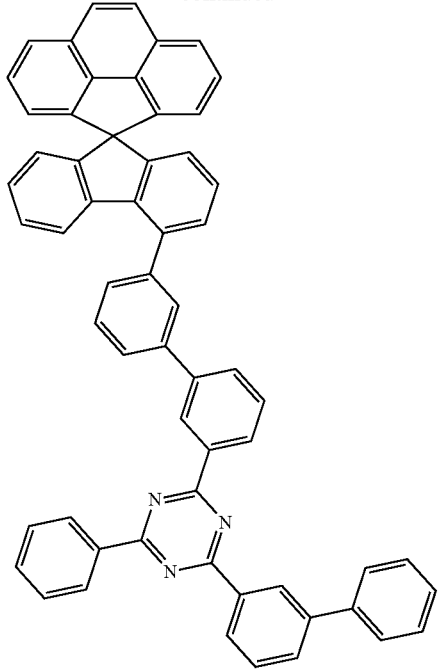
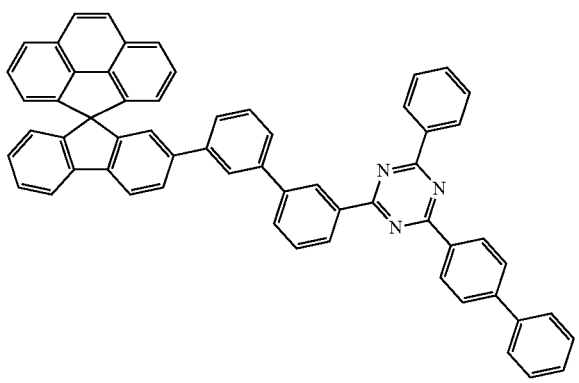
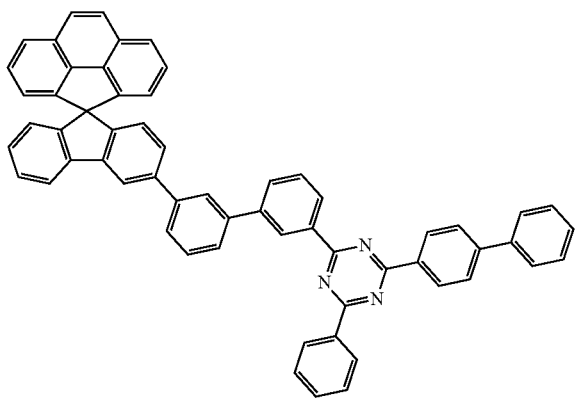

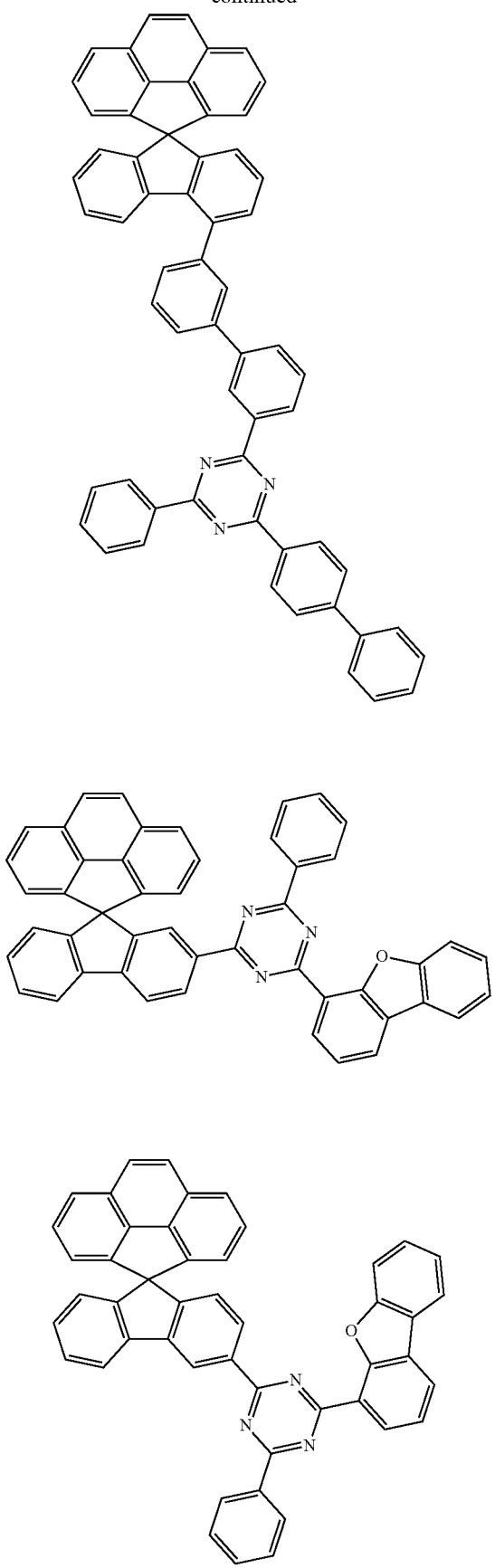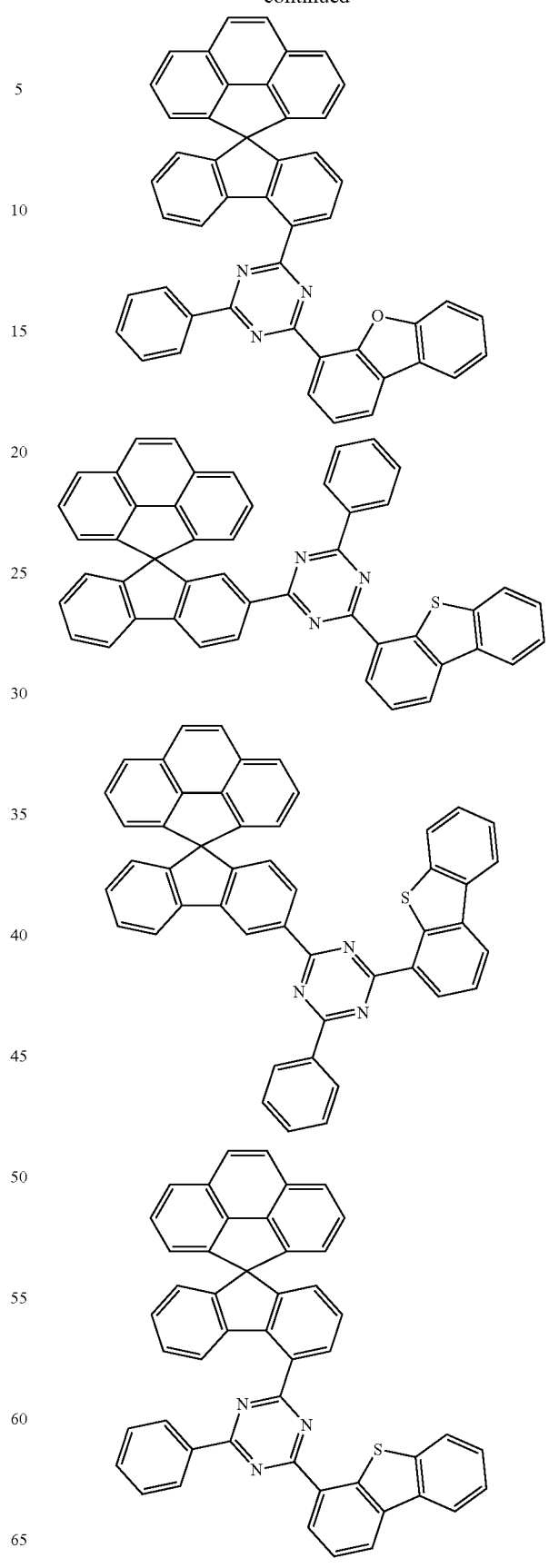

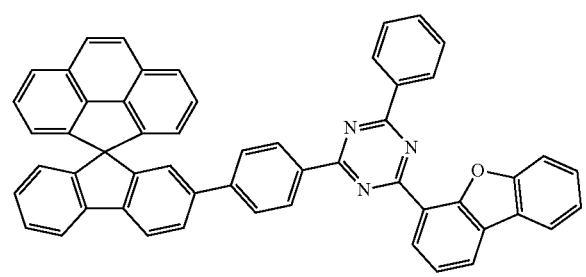
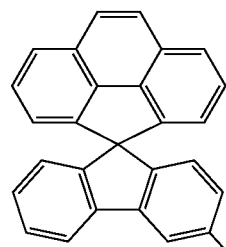
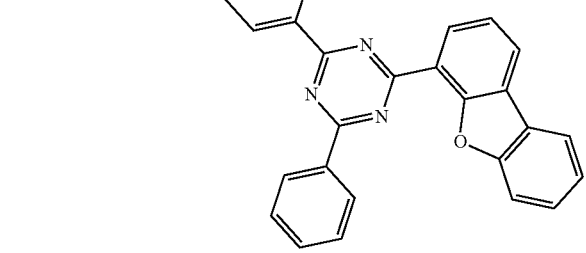
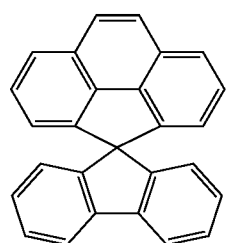
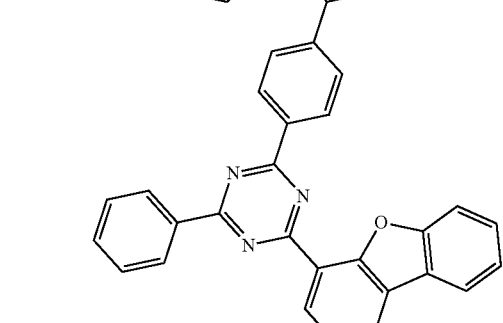
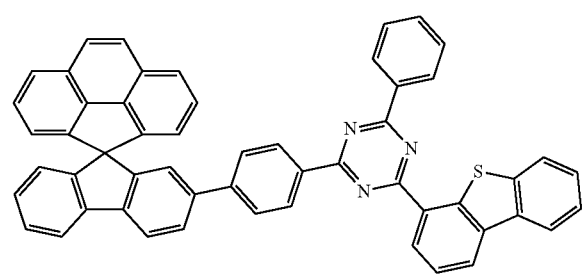
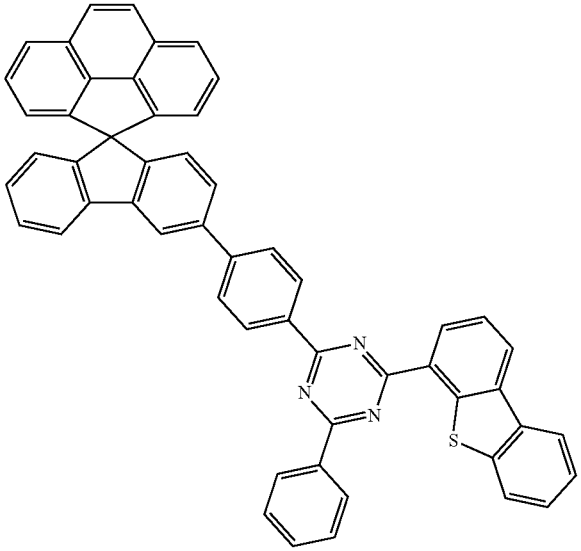
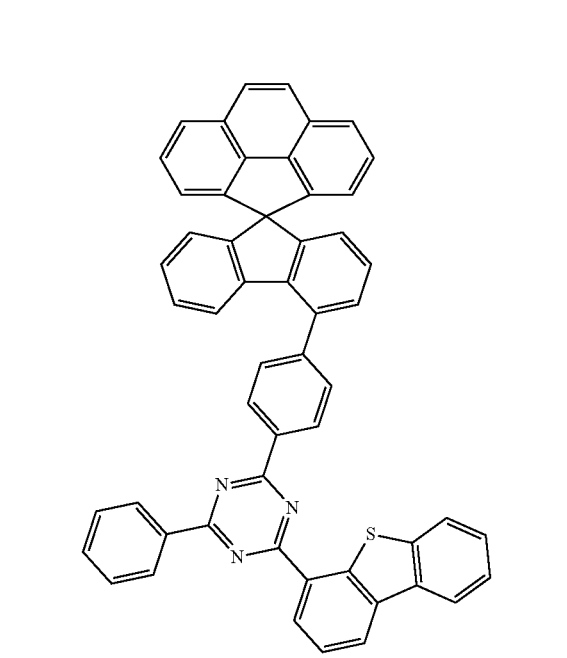
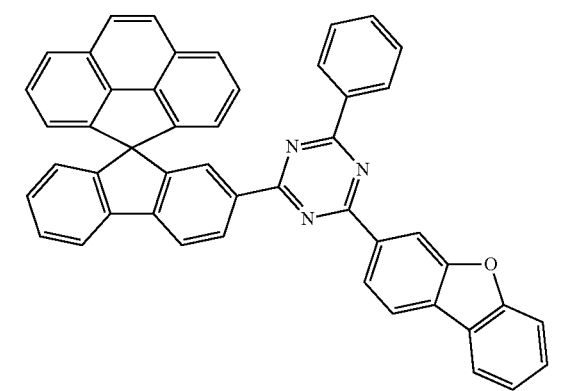

-continued
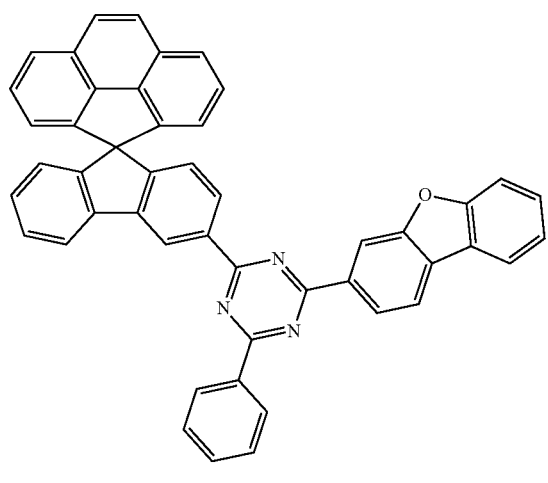
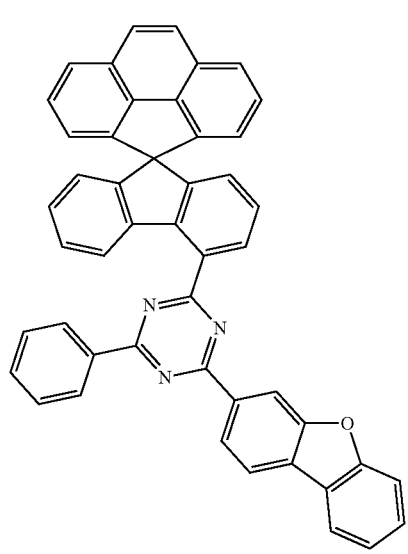
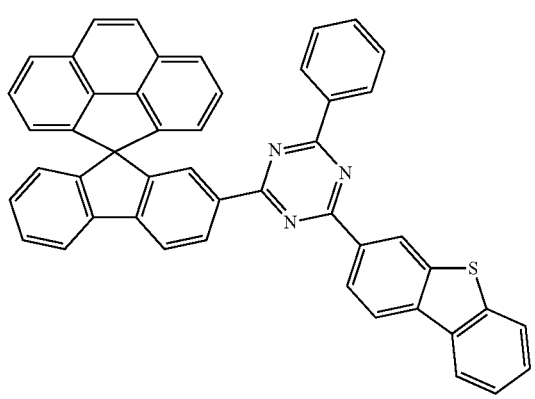
-continued
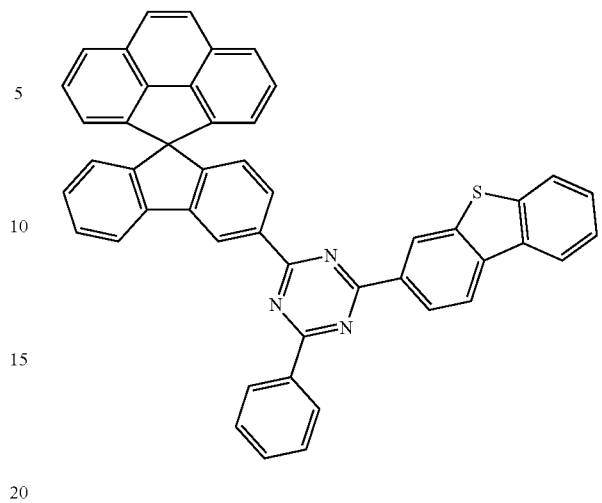
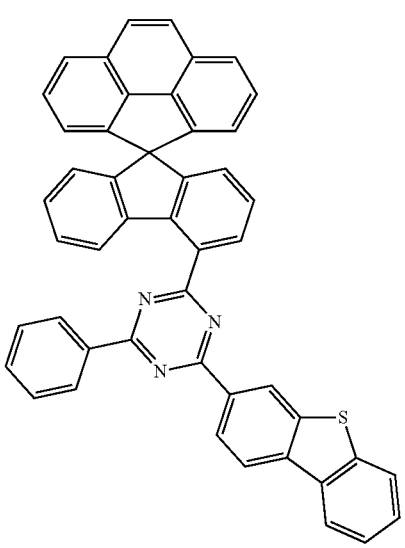
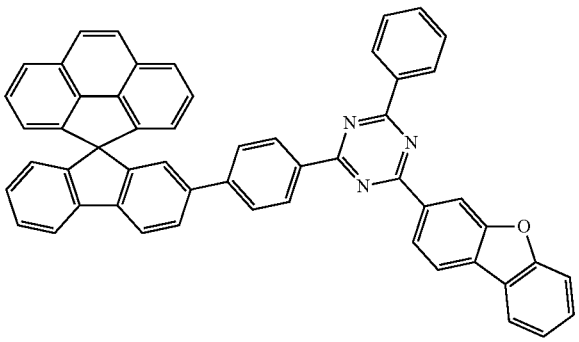

-continued
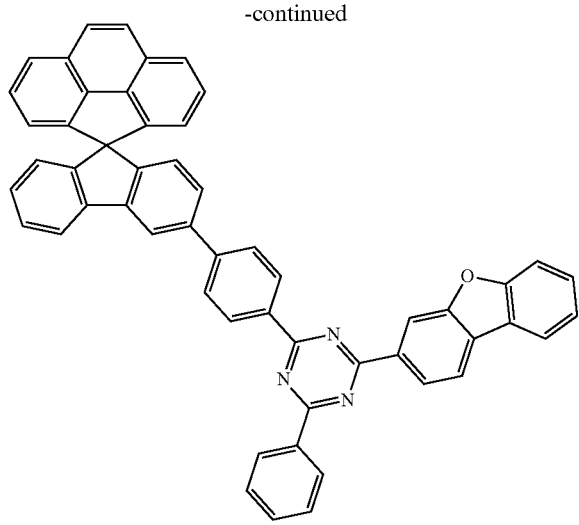
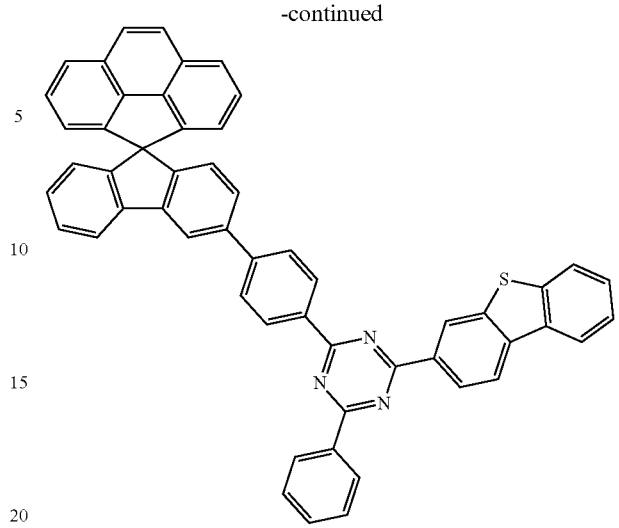
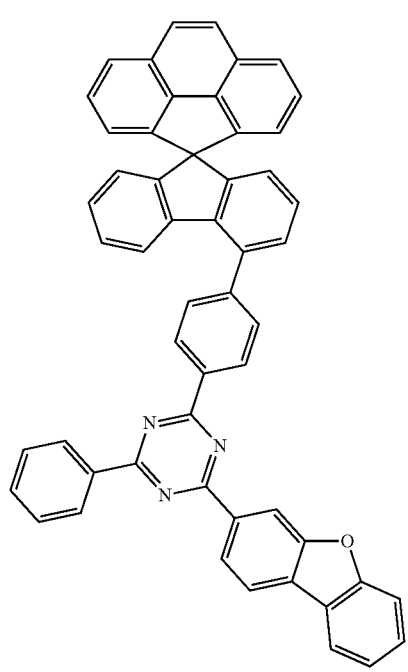
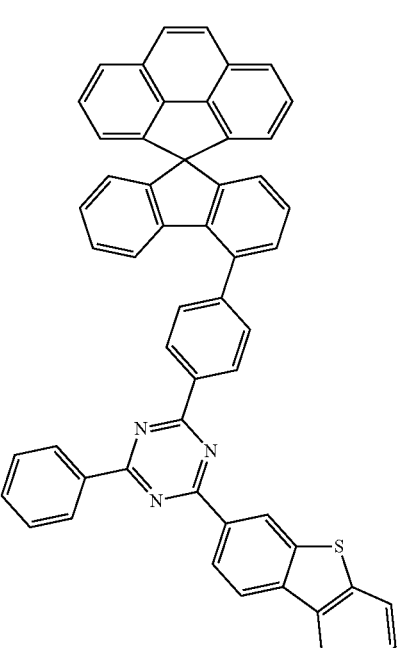
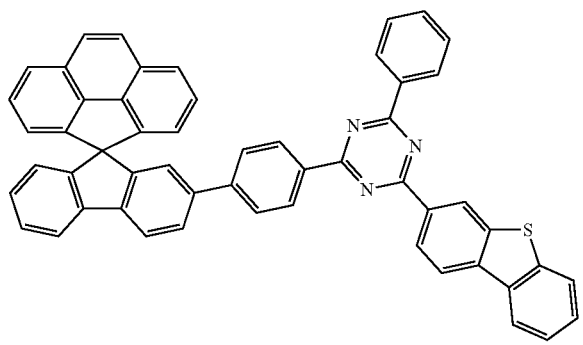
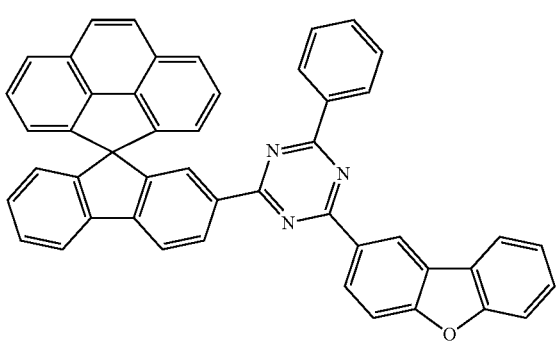

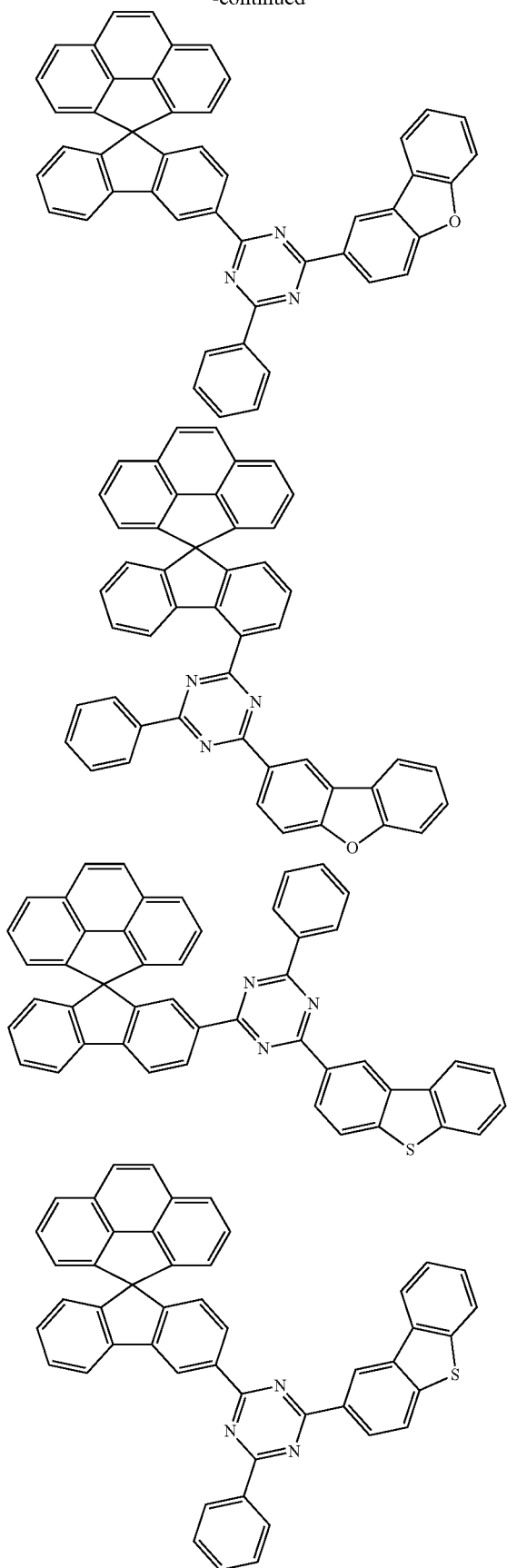

-continued
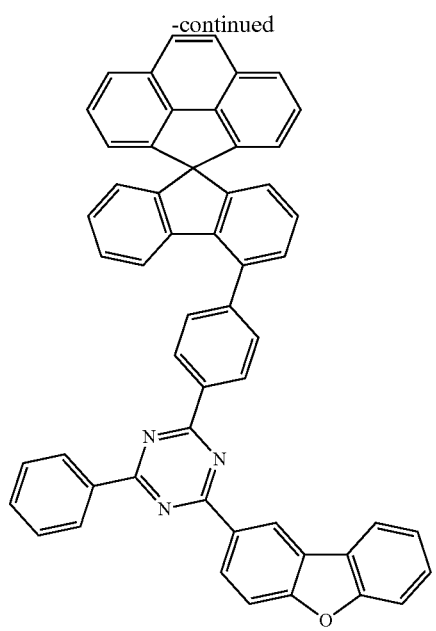
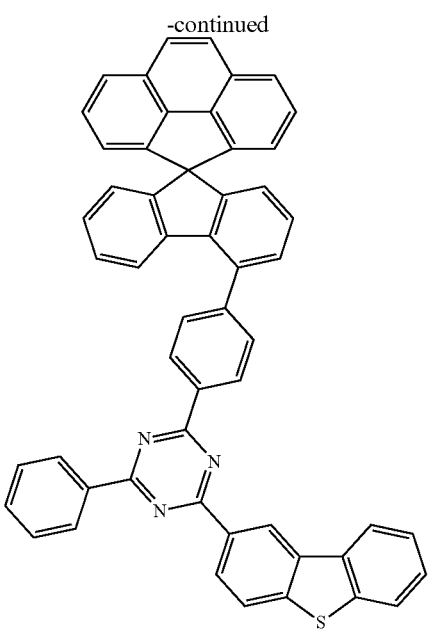
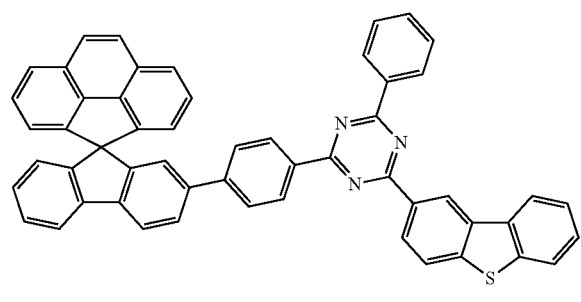
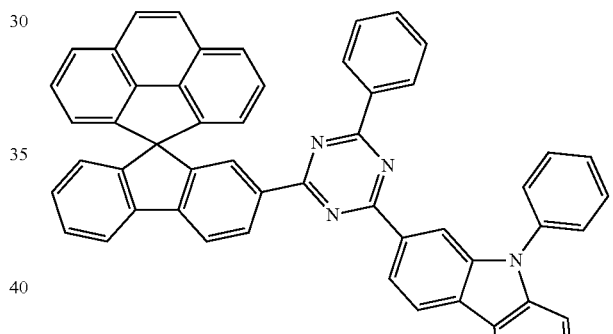
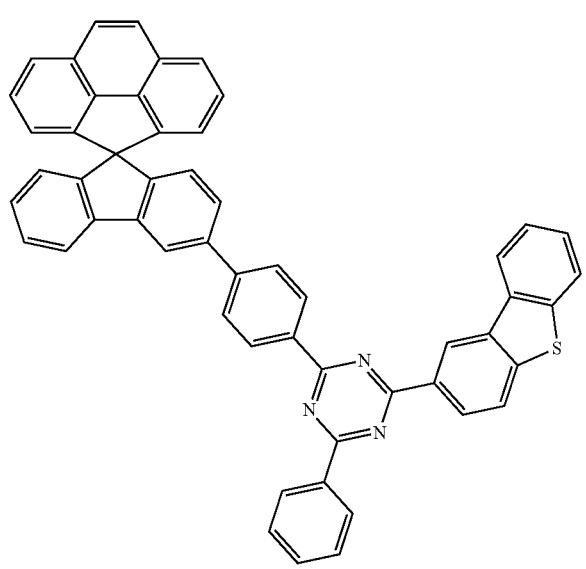
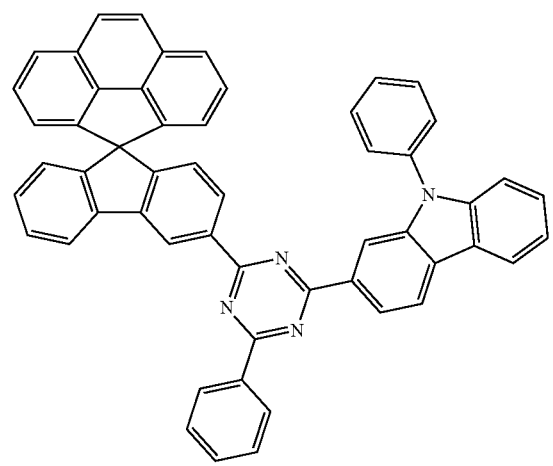

49
-continued
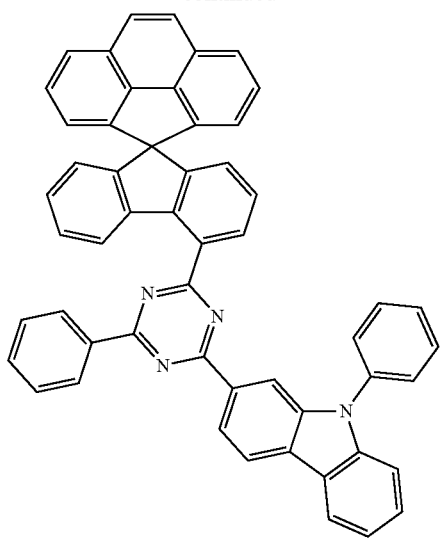
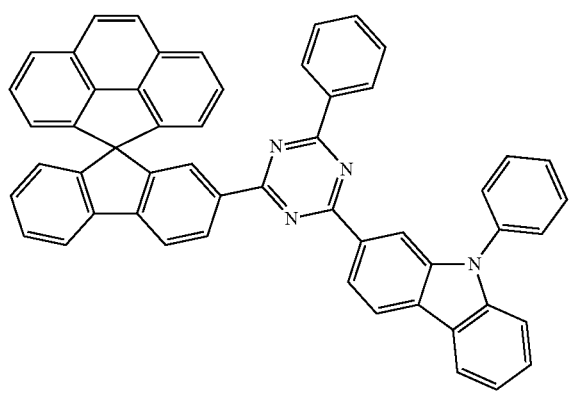
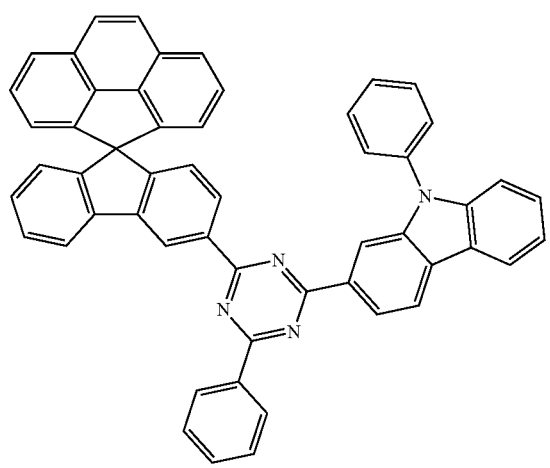
50
-continued
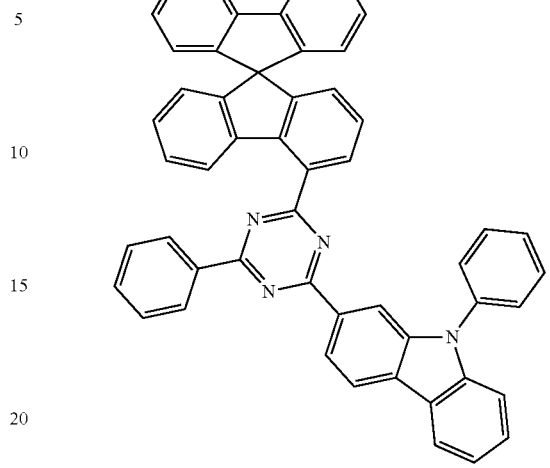
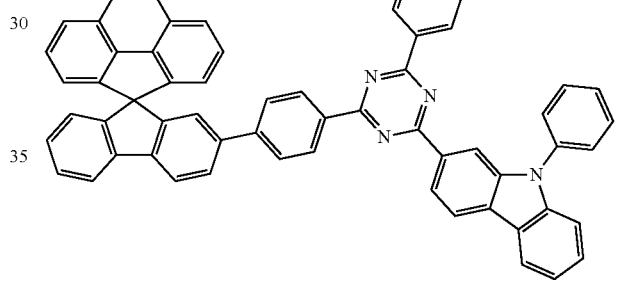
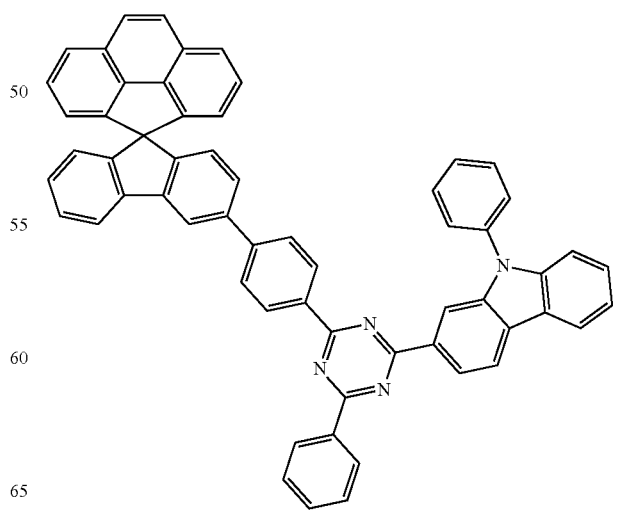

51
-continued
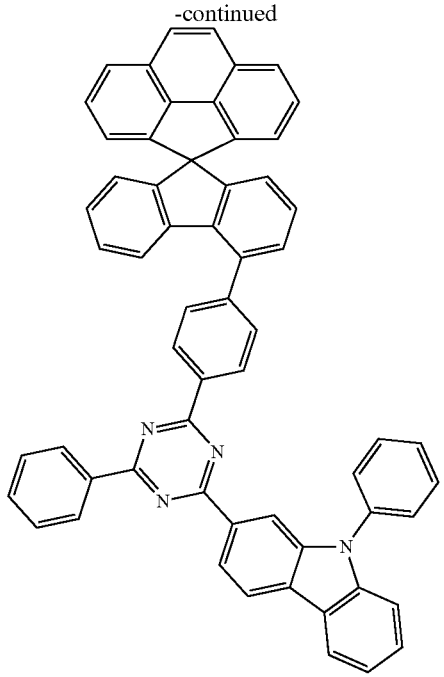
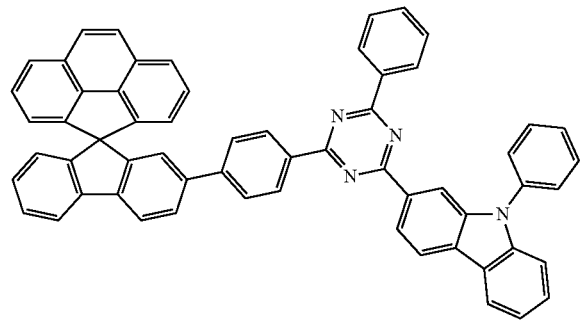
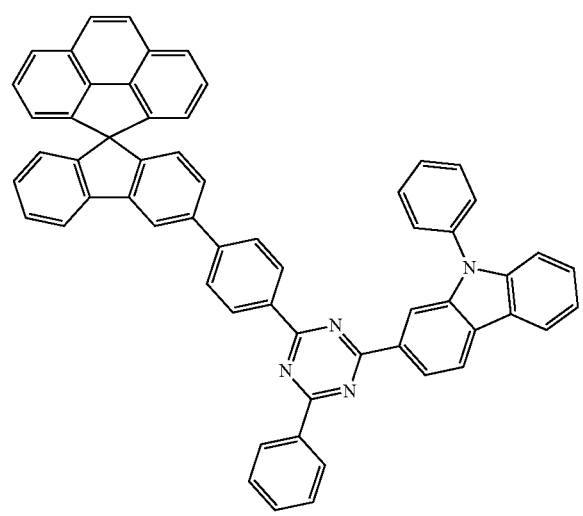
52
-continued
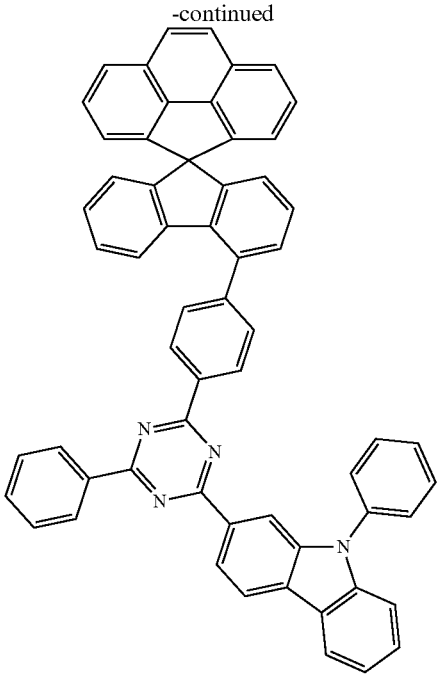
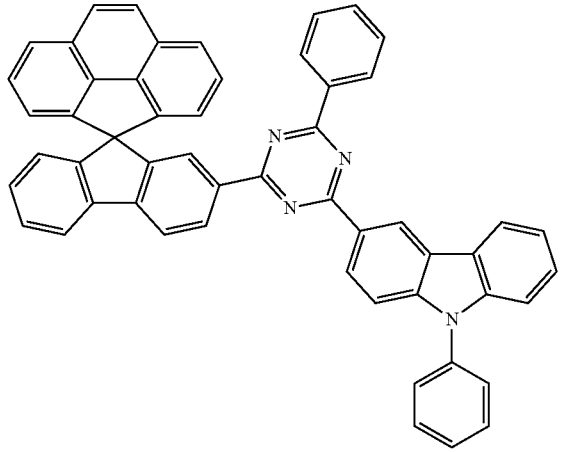
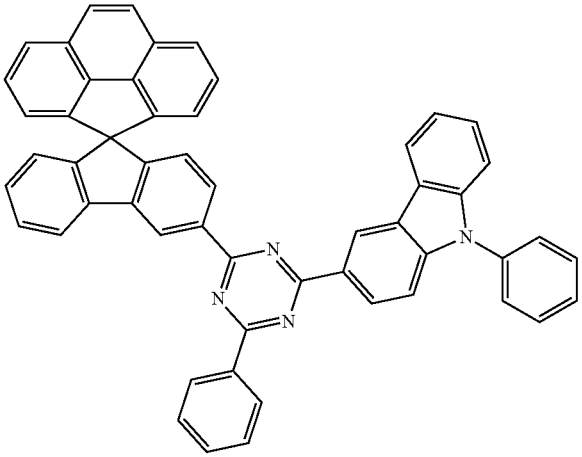

53
-continued
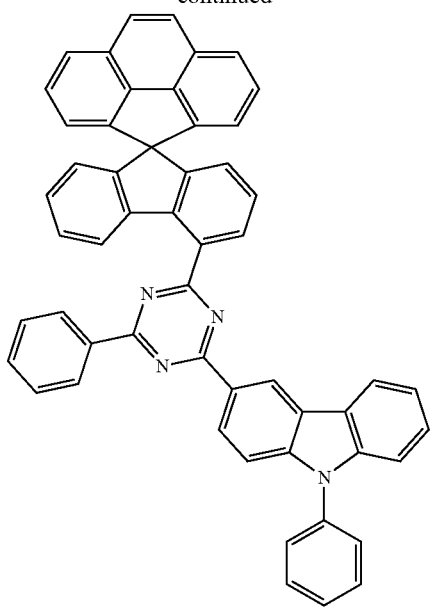
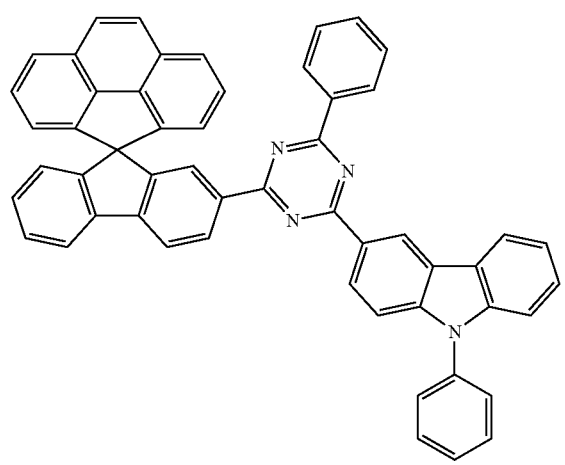
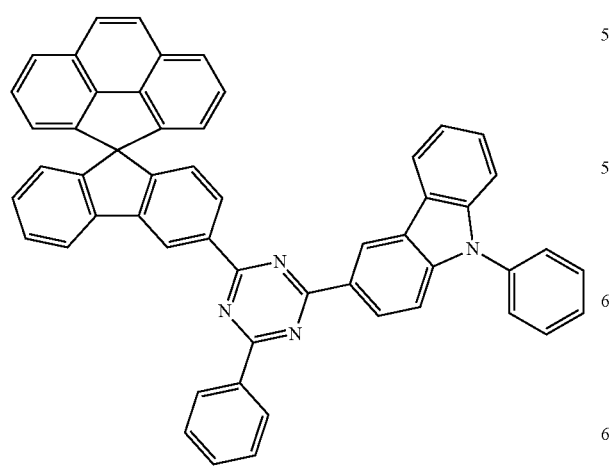
54
-continued
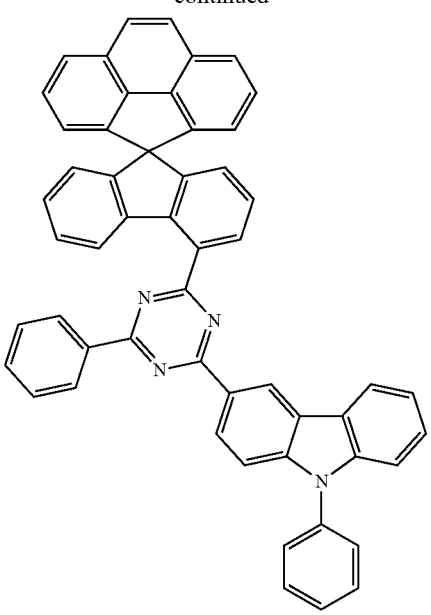
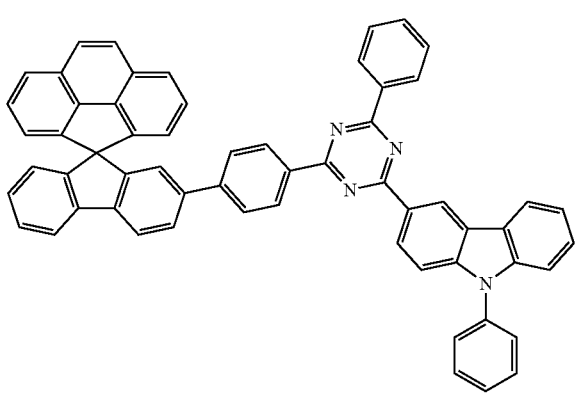
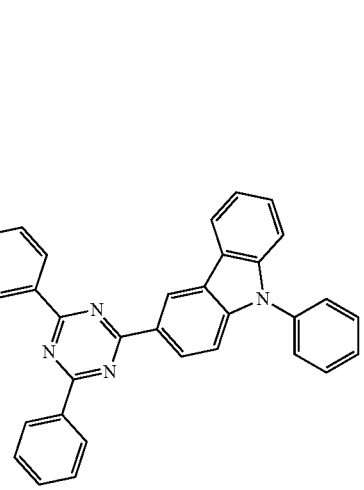

55
-continued
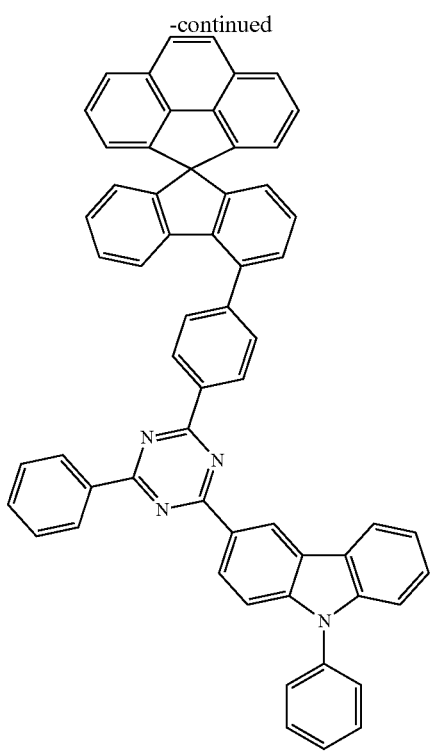
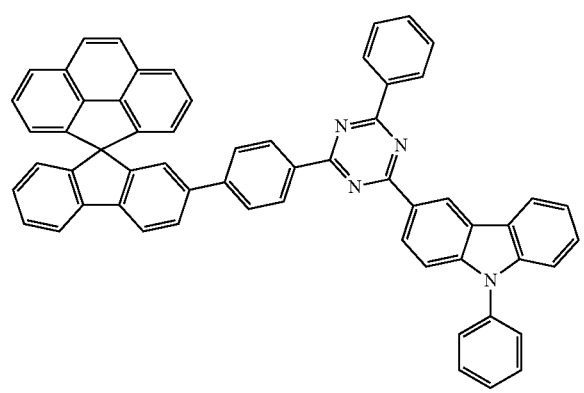
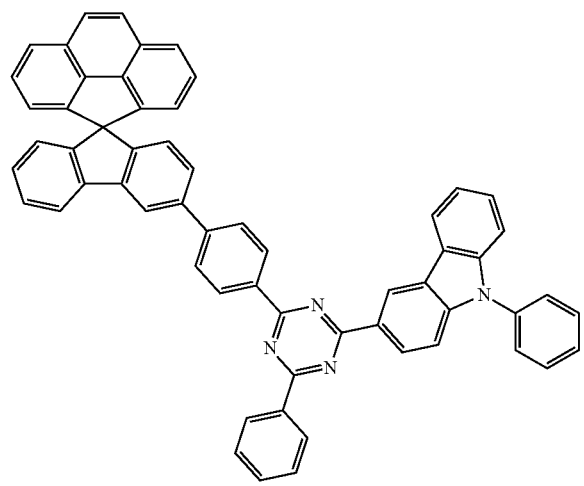
56
-continued
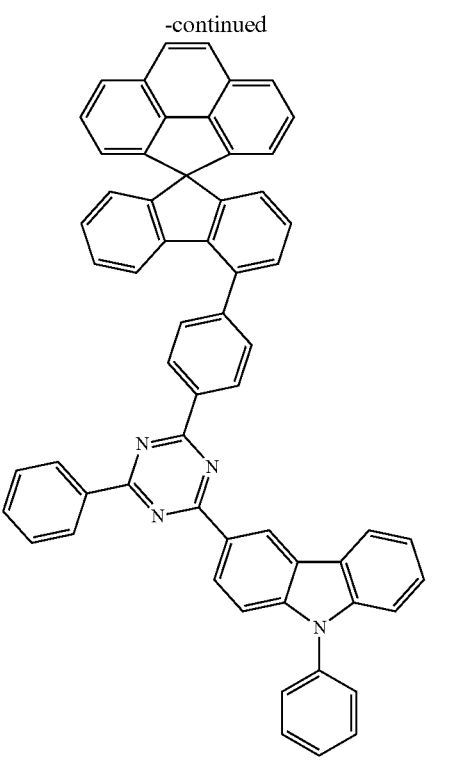
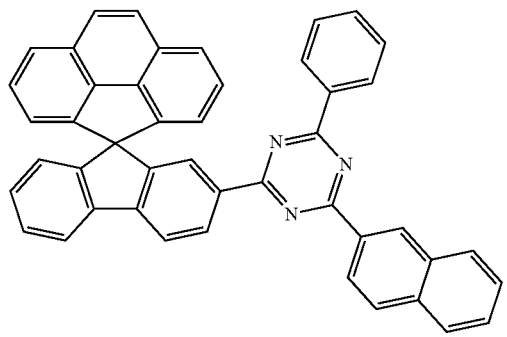
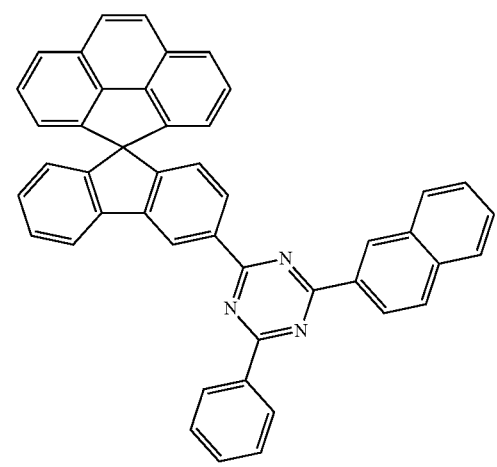

-continued
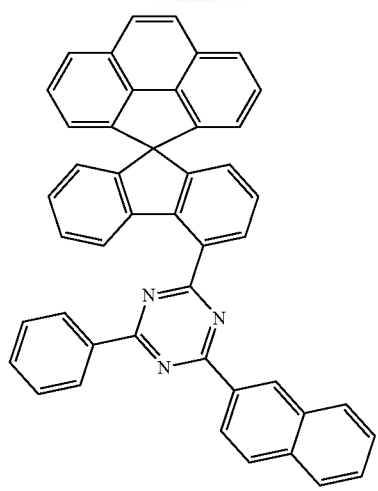
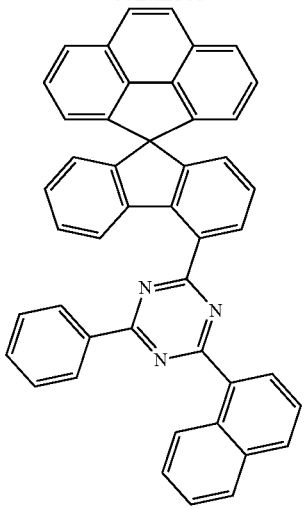
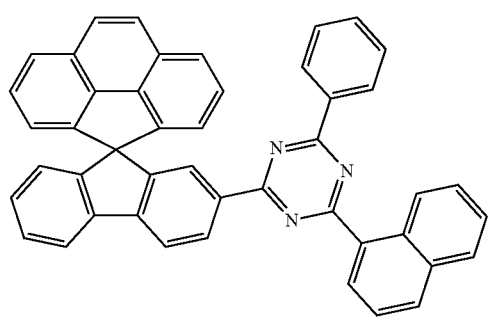
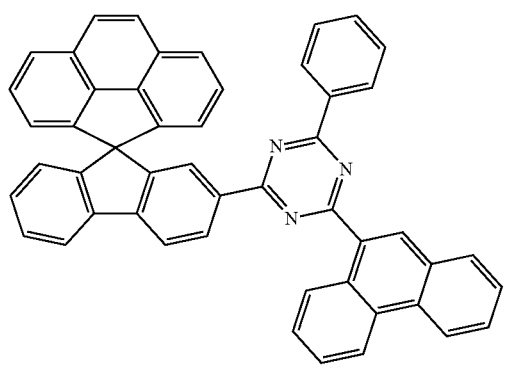
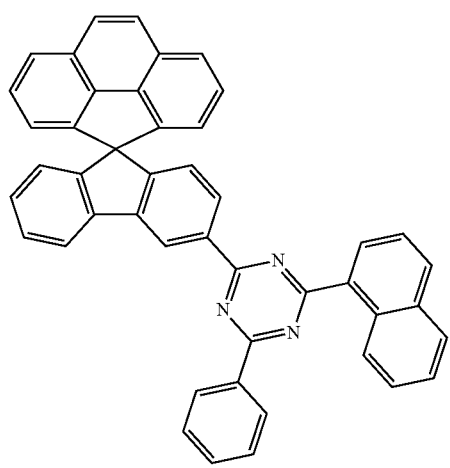
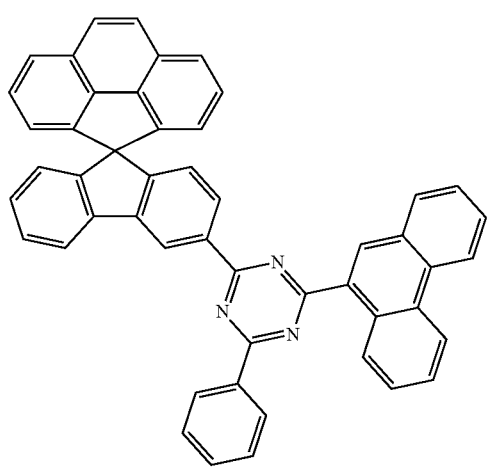

| 59 -continued | 60 -continued |
|---|---|
| 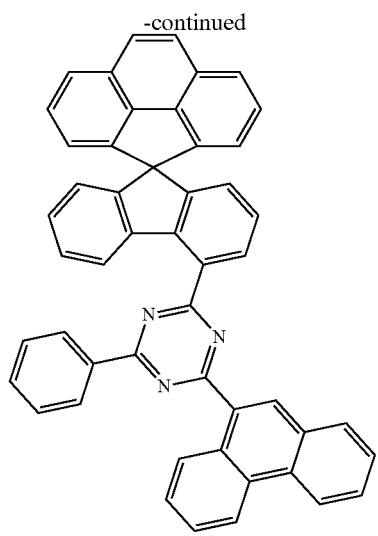 | 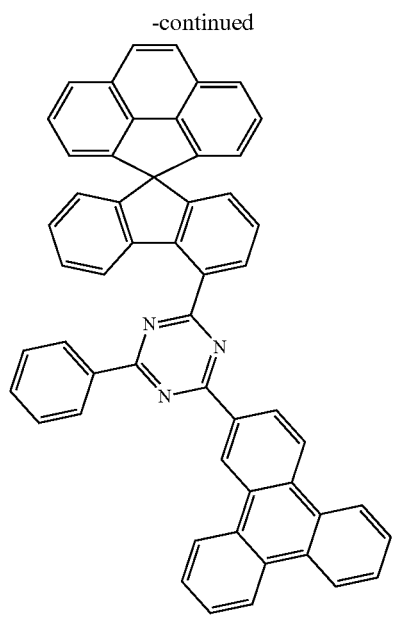 |
| 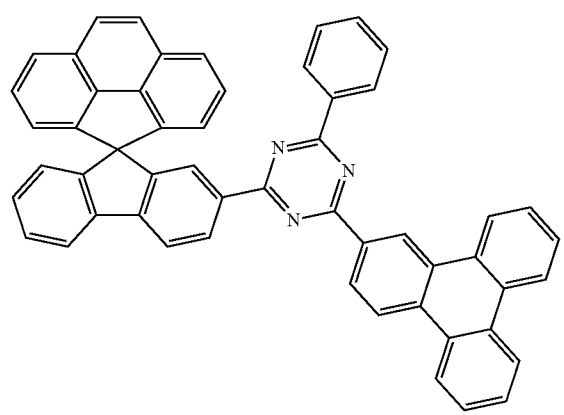 | 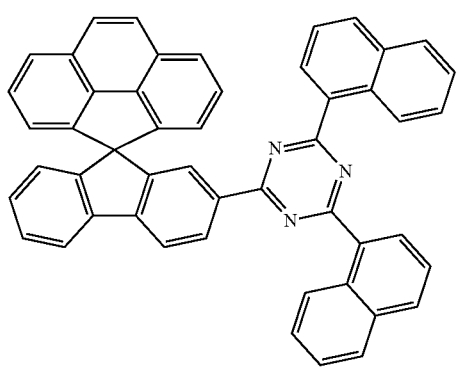 |
| 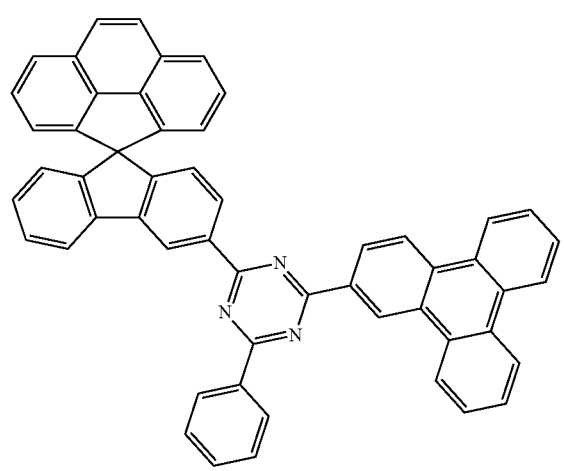 | 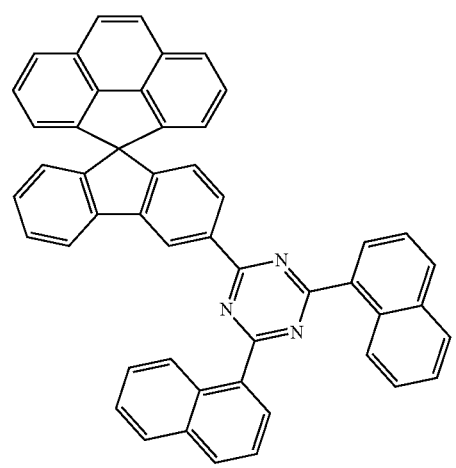 |

61
-continued
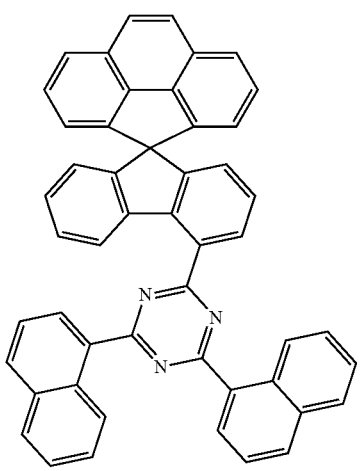
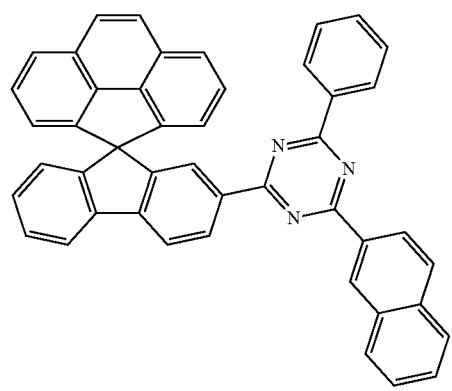
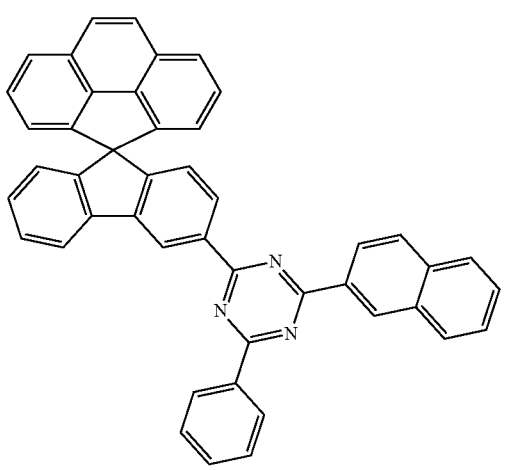
62
-continued
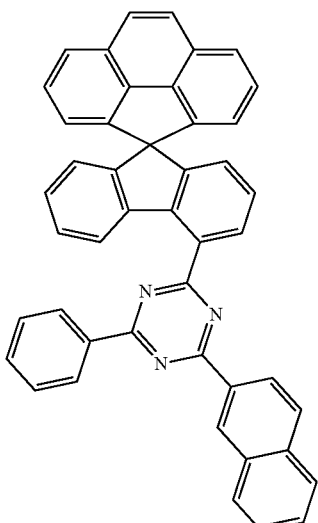
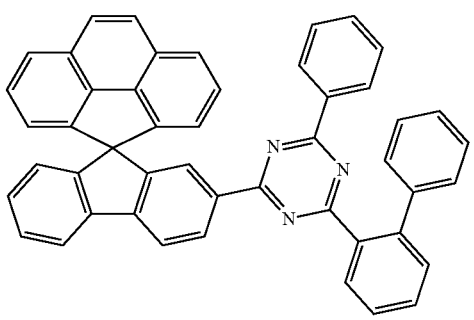
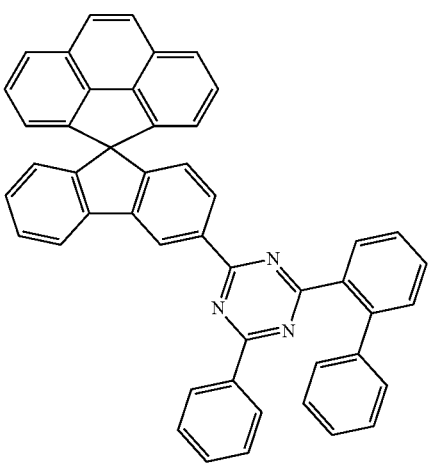

63
-continued
64
-continued
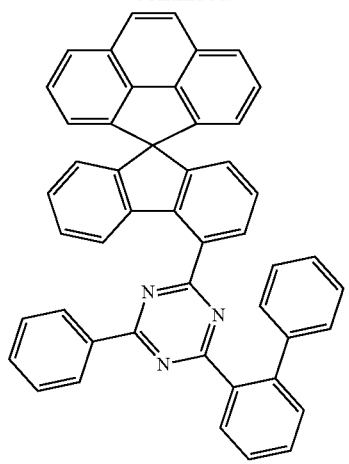
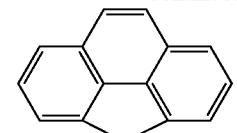
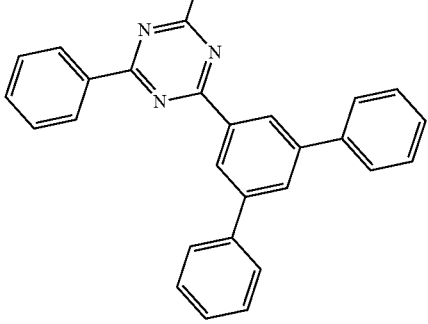
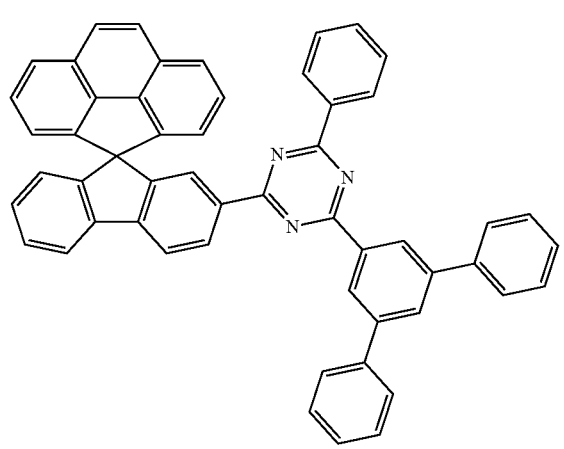
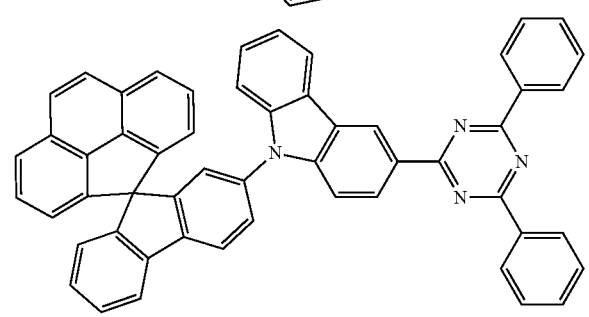
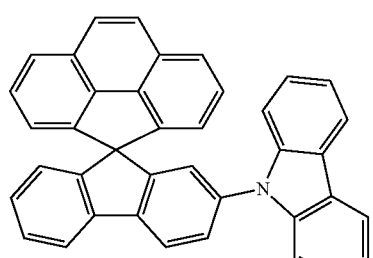
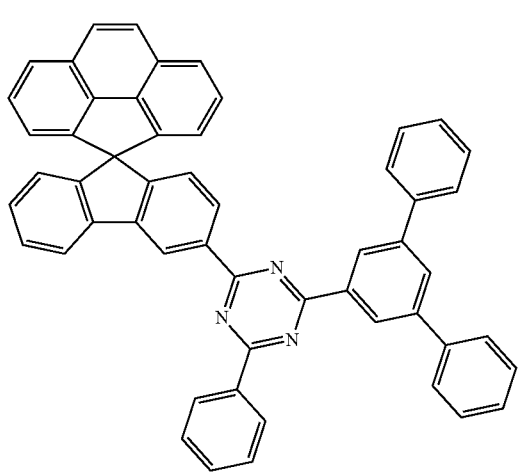
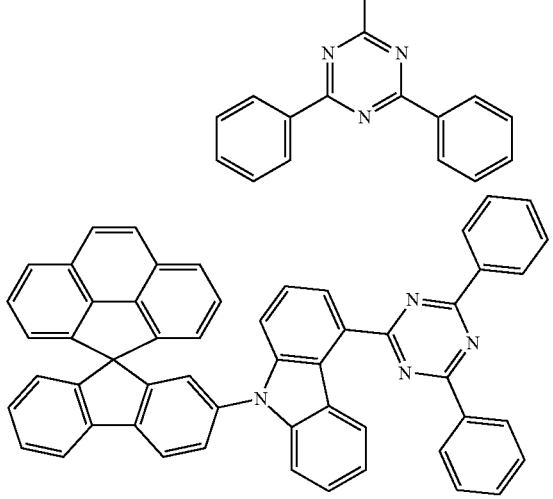

65
-continued
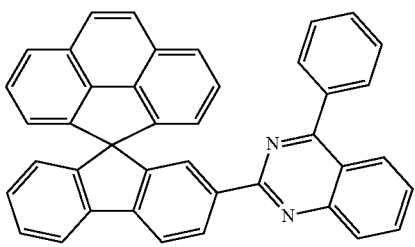
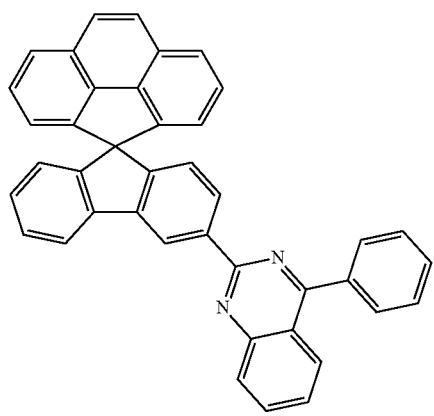
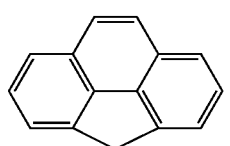
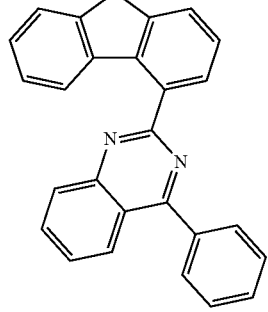
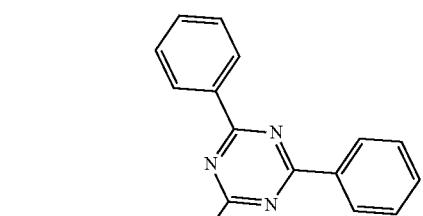
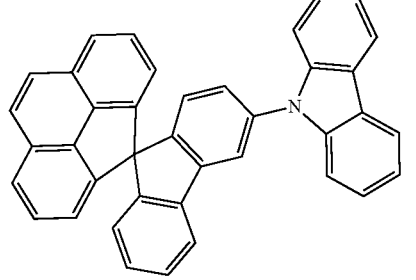
66
-continued
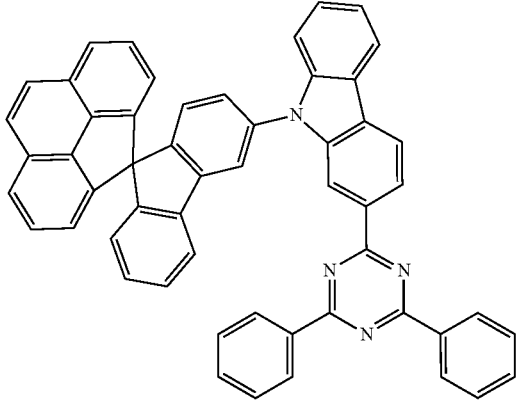
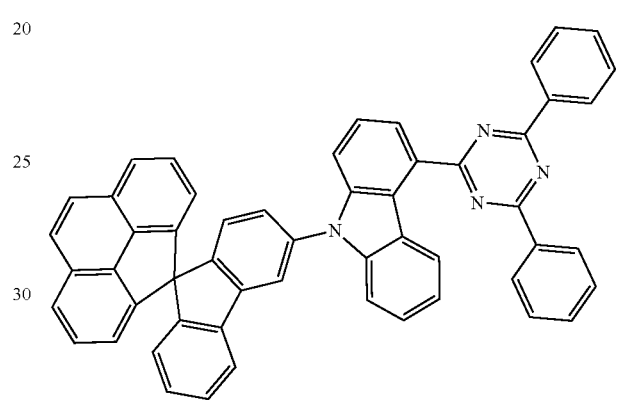
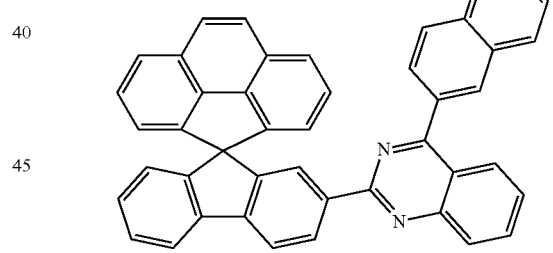
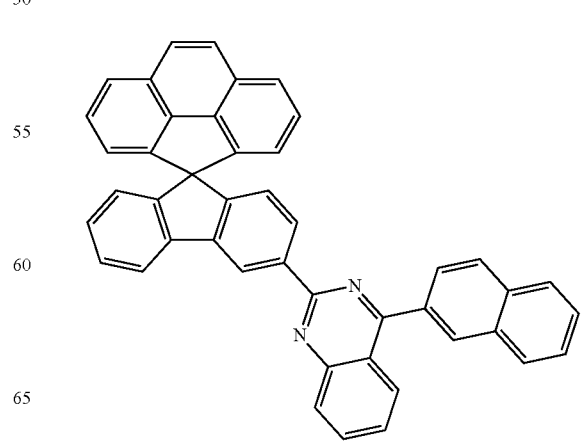

67
-continued
68
-continued
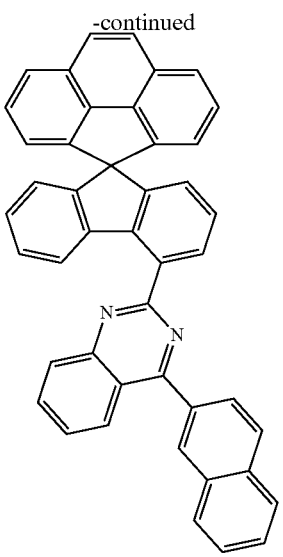
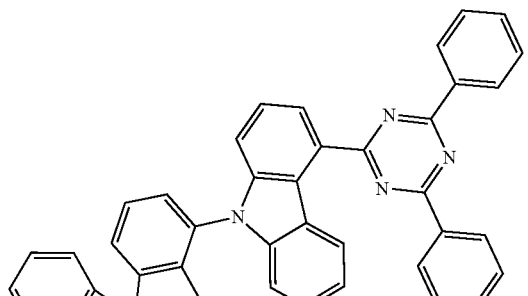
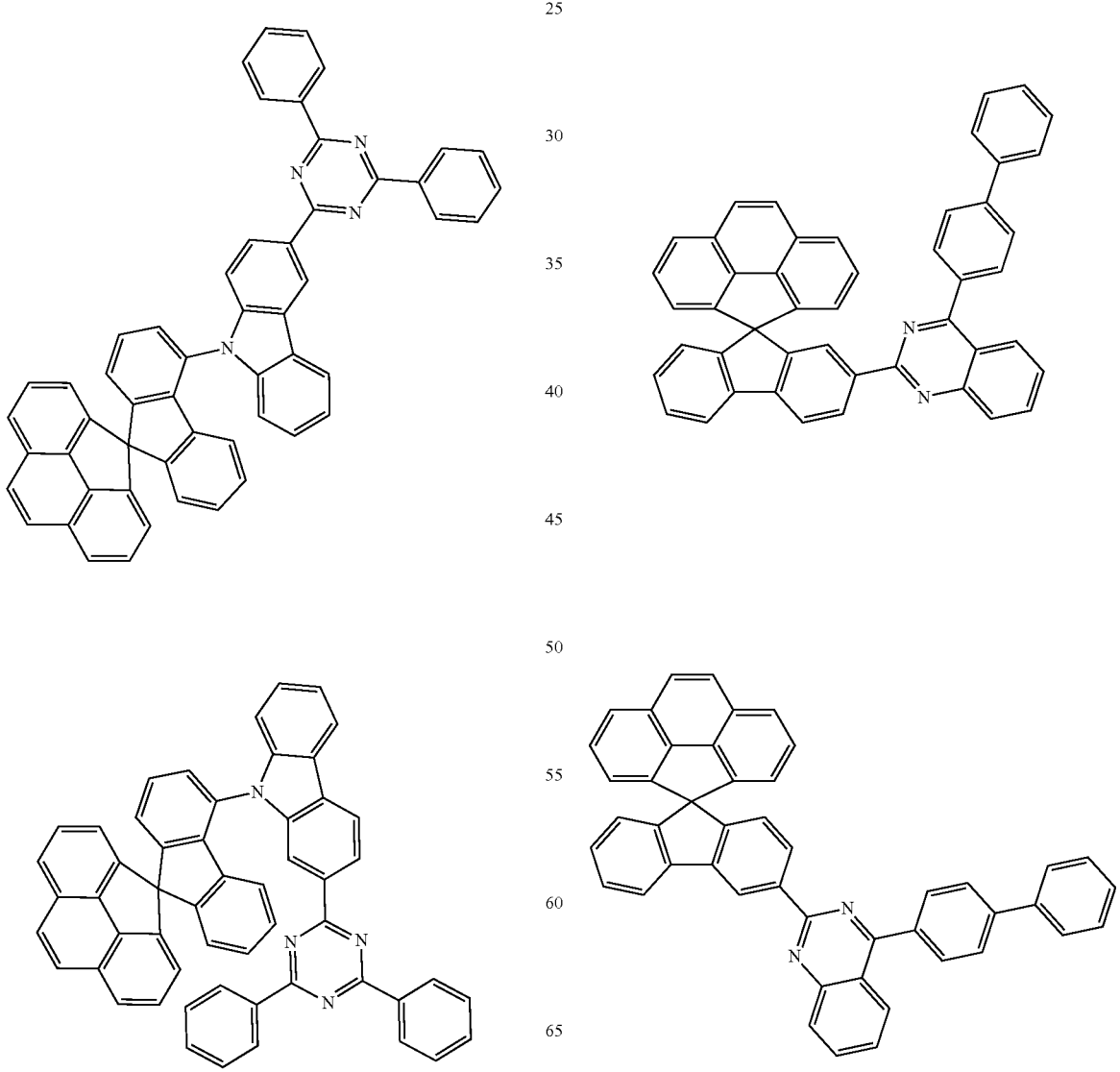

69
-continued
70
-continued
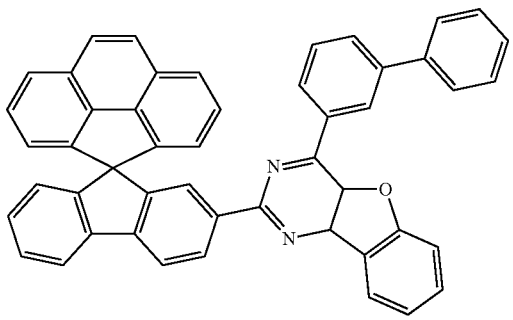
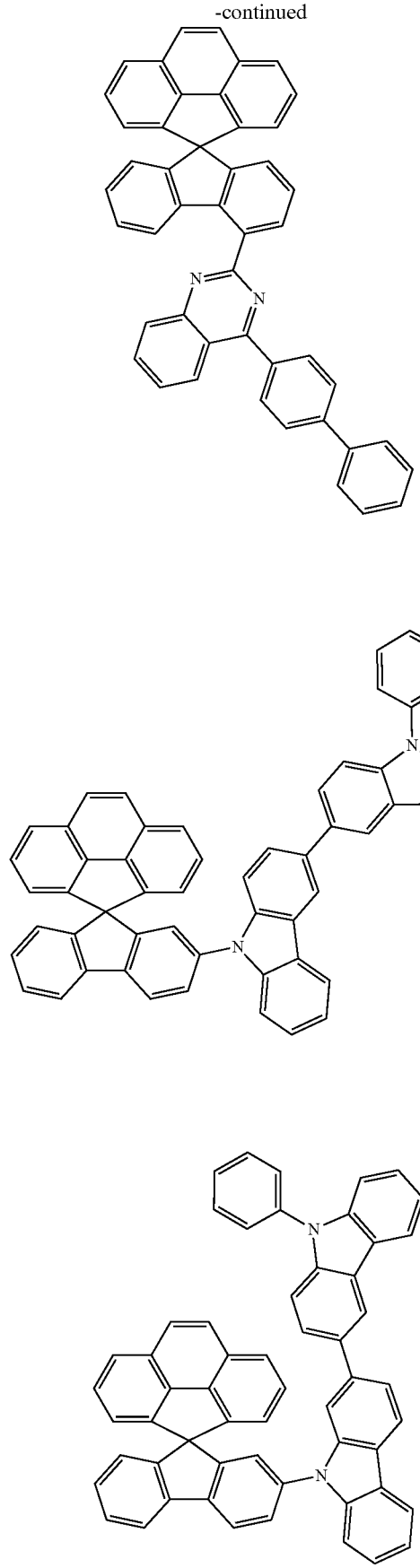
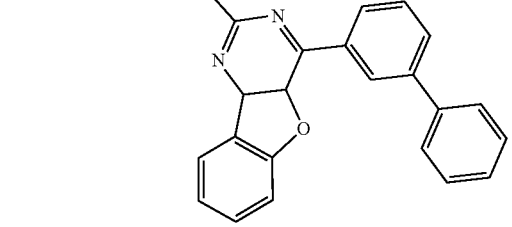
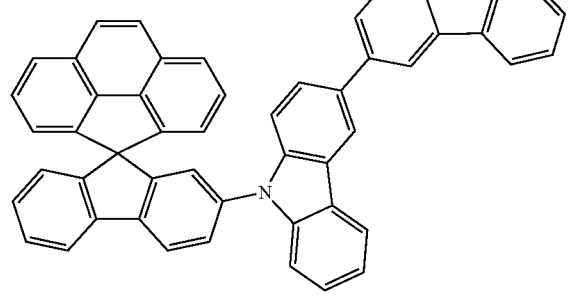
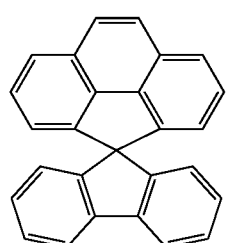
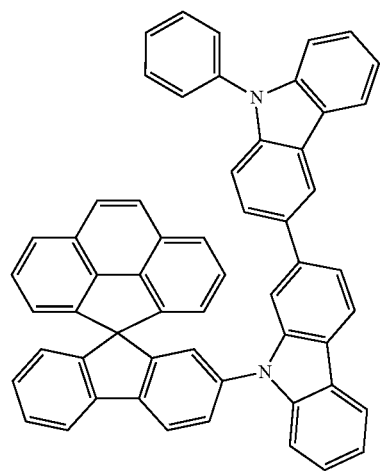
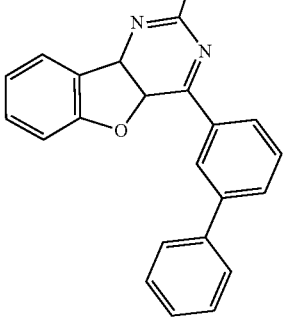

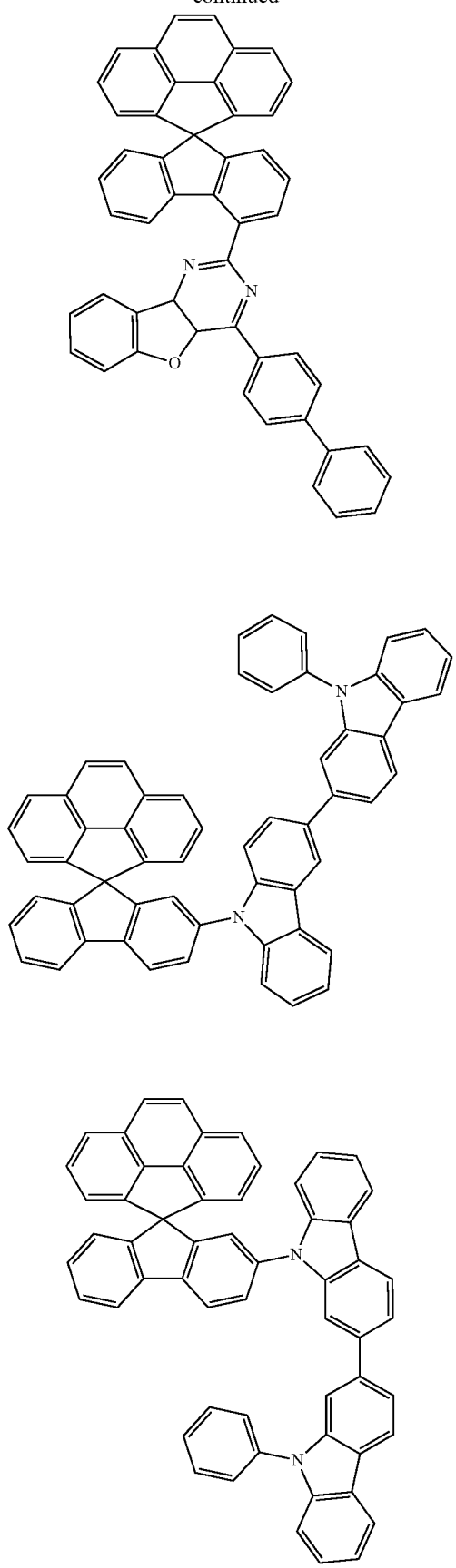
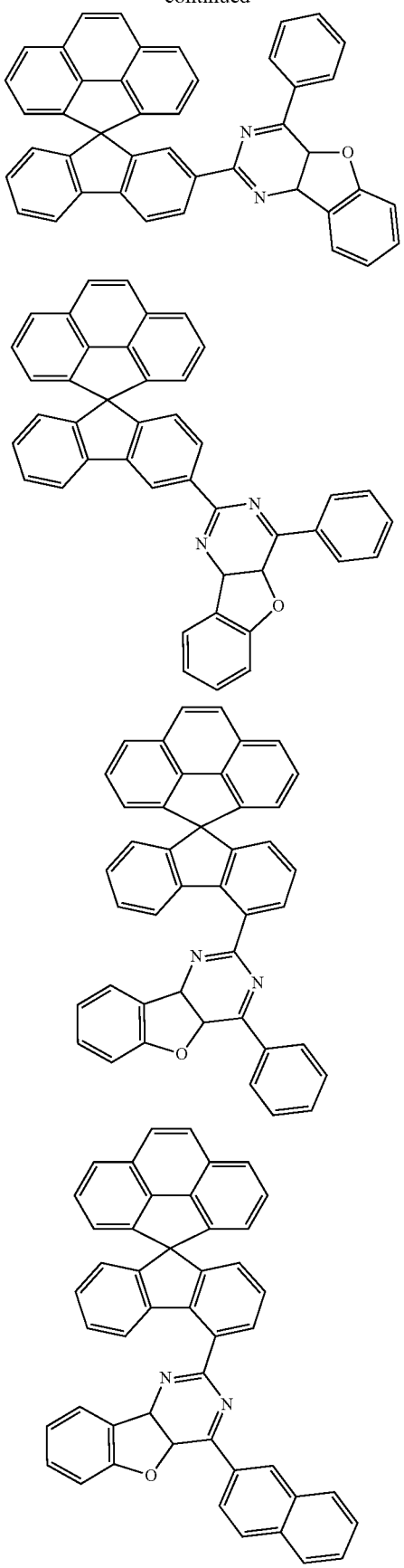

-continued
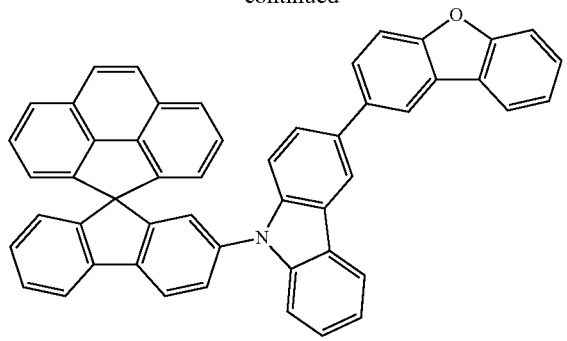
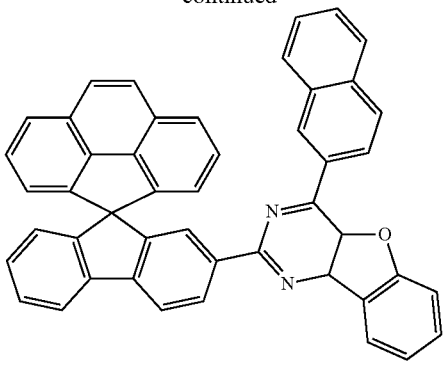
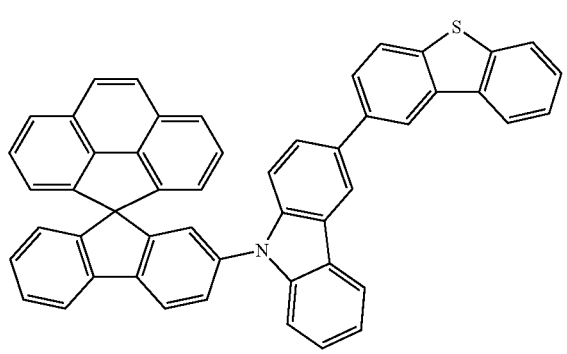
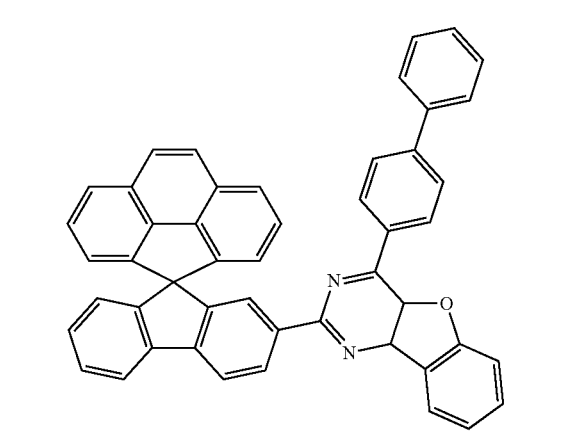
In another embodiment of the invention, provided is a process for preparing a compound of Chemical Formula 1 as shown in the following Reaction Scheme 1 or 2:
Reaction Scheme 1
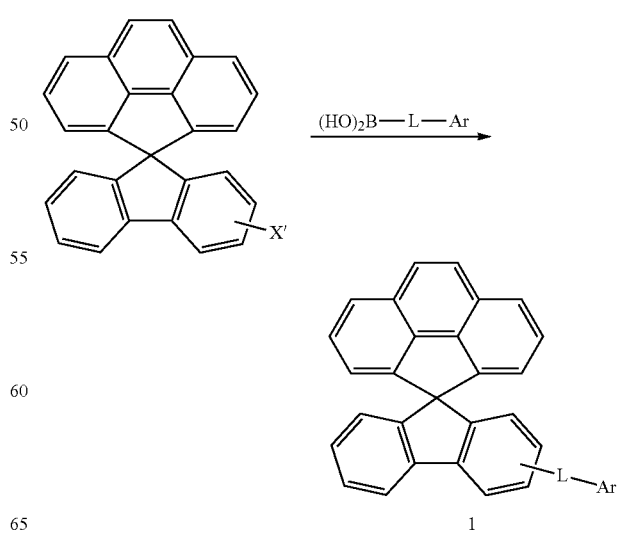

Reaction Scheme 2

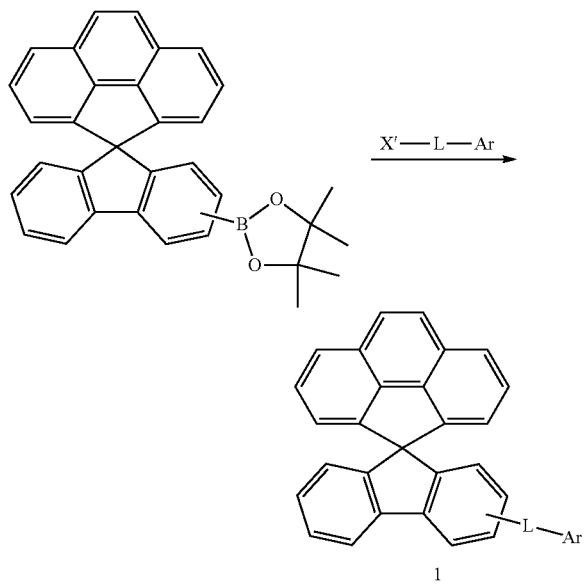

In the reaction schemes 1 and 2, L and Ar are same as those defined above, and X' is halogen, preferably bromo, or chloro. Reaction Schemes 1 and 2 are Suzuki coupling reactions, which are preferably carried out in the presence of a palladium catalyst and a base, and the reactive group for the Suzuki coupling reaction can be modified as known in the art. The above preparation method is further described in Preparation Examples to be described later.

In still another embodiment of the invention, provided is an organic light emitting device including a compound of Chemical Formula 1. As an example, provided is an organic light emitting device including: a first electrode; a second electrode provided opposite to the first electrode; and one or more organic material layers provided between the first electrode and the second electrode, wherein one or more layers of the organic material layers includes the compound of Chemical Formula 1.

The organic material layer of the organic light emitting device of the present invention can have a single layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a light emitting layer, wherein the light emitting layer includes a compound of Chemical Formula 1. In particular, the compound according to the present invention can be used as a dopant in a light emitting layer.

Further, the organic material layer can include an electron transport layer, or an electron injection layer, wherein the electron transport layer, or the electron injection layer includes a compound of Chemical Formula 1.

Further, the electron transport layer, the electron injection layer, or a layer simultaneously performing electron transport and electron injection includes a compound of Chemical Formula 1.

Further, the organic material layer includes a light emitting layer and an electron transport layer, wherein the electron transport layer can include a compound of Chemical Formula 1.

Further, the organic light emitting device according to the present invention can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, an organic material layer 3, and a cathode 4. In such a structure, the compound of Chemical Formula 1 can be included in the organic material layer.

FIG. 2 shows an example of an organic light emitting device comprising a substrate 1, an anode 2, a hole injection layer 5, a hole transport layer 6, an electron blocking layer 7, a light emitting layer 8, a hole blocking layer 9, an electron transport layer 10, an electron injection layer 11, and a cathode 4. In such a structure, the compound of Chemical Formula 1 can be included in one or more layers of the hole injection layer, the hole transport layer, the electron blocking layer, the light emitting layer, the hole blocking layer, the electron transport layer, and the electron injection layer.

The organic light emitting device according to the present invention can be manufactured by materials and methods known in the art, except that one or more layers of the organic material layers includes the compound of Chemical Formula 1. In addition, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device can be manufactured by sequentially depositing a cathode material, an organic material layer and an anode material on a substrate.

In addition, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as $ZnO:Al$ or $SnO_2:Sb$; conductive polymers such as poly(3-methylthiophene), poly[3,4-(ethylene-1,2-dioxy)-thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as $LiF/Al$ or $LiO_2/Al$, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylene-vinylene)(PPV)-based polymer; a Spiro compound; polyfluorene, rubrene, and the like, but are not limited thereto.

The light emitting layer can include a host material and a dopant material. The host material can be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxy-benzo[h]quinolinato)beryllium, bis(10-hydroxybenzo[h]-quinolinato)zinc, bis(2-methyl-8-quinolinato)chlorogallium, bis(2-methyl-8-quinolinato)(o-cresolato)gallium, bis(2-methyl-8-quinolinato)(1-naphtholato)-aluminum, bis(2-methyl-8-quinolinato)-(2-naphtholato)gallium, and the like, but are not limited thereto.

The organic light emitting device according to the present invention can be a front side emission type, a back side emission type, or a double side emission type according to the used material.

In addition, the compound of Chemical Formula 1 can be included in an organic solar cell or an organic transistor in addition to an organic light emitting device.

The preparation of the compound of Chemical Formula 1 and the organic light emitting device comprising the same will be described in detail in the following examples. However, these examples are presented for illustrative purposes only, and are not intended to limit the scope of the present invention.

Examples

Example 1: Preparation of Compound 1

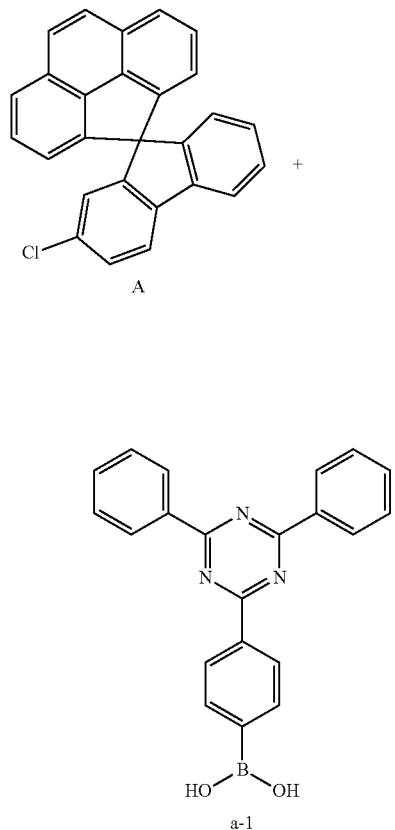

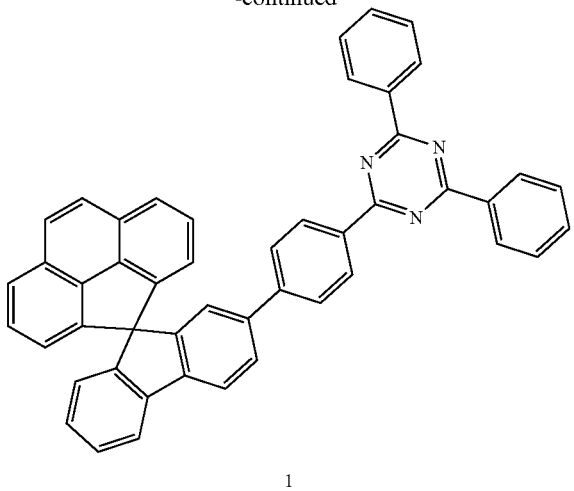

Compound A (7.50 g, 20.05 mmol) and Compound a-1 (7.43 g, 21.06 mmol) were completely dissolved in tetrahydrofuran (240 ml) in a 500-ml round bottom flask under a nitrogen atmosphere, to which a 2 M aqueous potassium carbonate solution (120 ml) was added and tetrakis-(triphenylphosphine)-palladium (0.70 g, 0.60 mmol) was added, and then the resulting mixture was heated and stirred for 4 hours. The temperature was lowered to room temperature, the aqueous layer was removed, and the resulting product was dried over anhydrous magnesium sulfate, and then concentrated under reduced pressure, and recrystallized with tetrahydrofuran (180 ml) to prepare Compound 1 (8.76 g, yield: 67%).

MS: $[M+H]^+=648$

Example 2: Preparation of Compound 2

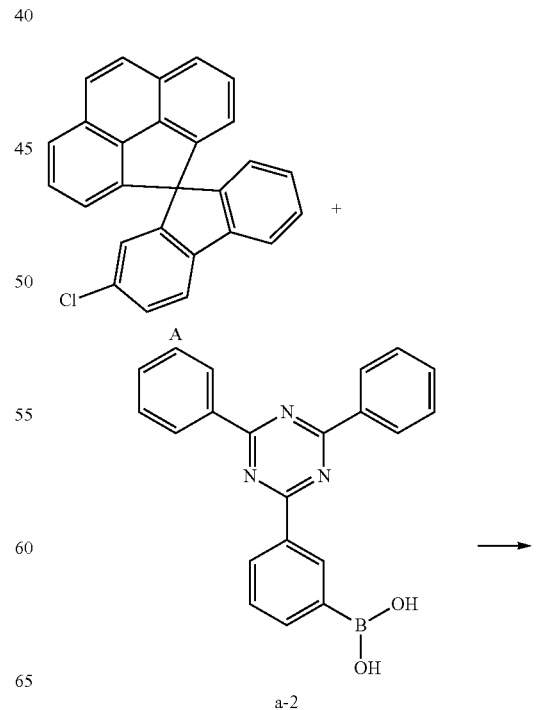

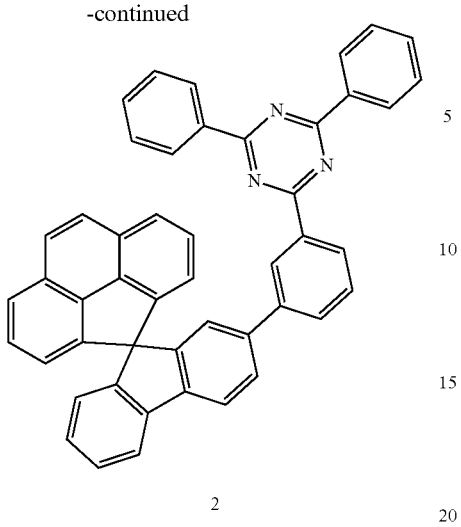

2

Compound A (6.50 g, 17.38 mmol) and Compound a-2 (6.44 g, 18.25 mmol) were completely dissolved in tetrahydrofuran (260 ml) in a 500-ml round bottom flask under a nitrogen atmosphere, to which a 2 M aqueous potassium carbonate solution (130 ml) was added and tetrakis-(triphenylphosphine)-palladium (0.60 g, 0.52 mmol) was added, and then the resulting mixture was heated and stirred for 3 hours. The temperature was lowered to room temperature, the aqueous layer was removed, and the resulting product was dried over anhydrous magnesium sulfate, and then concentrated under reduced pressure, and recrystallized with ethyl acetate (270 ml) to prepare Compound 2 (7.46 g, yield: 66%).

MS: [M+H]$^+$=648

Example 3: Preparation of Compound 3

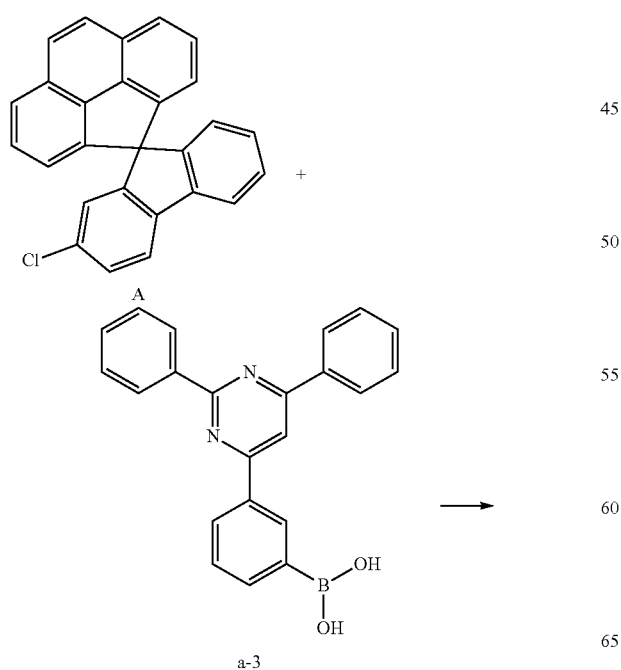

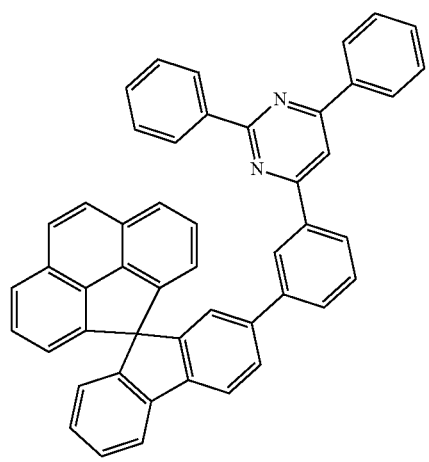

3

Compound A (8.50 g, 22.73 mmol) and Compound a-3 (8.42 g, 23.86 mmol) were completely dissolved in tetrahydrofuran (240 ml) in a 500-ml round bottom flask under a nitrogen atmosphere, to which a 2 M aqueous potassium carbonate solution (120 ml) was added and tetrakis-(triphenylphosphine)-palladium (0.79 g, 0.68 mmol) was added, and then the resulting mixture was heated and stirred for 2 hours. The temperature was lowered to room temperature, the aqueous layer was removed, and the resulting product was dried over anhydrous magnesium sulfate, and then concentrated under reduced pressure, and recrystallized with ethyl acetate (210 ml) to prepare Compound 3 (7.89 g, yield: 54%).

MS: [M+H]$^+$=647

Example 4: Preparation of Compound 4

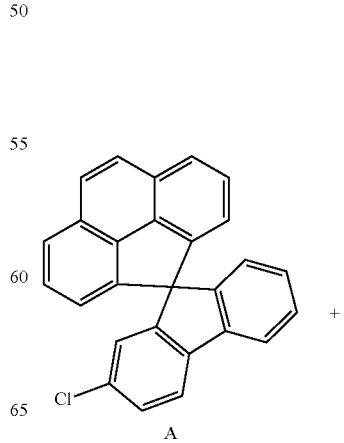

Example 5: Preparation of Compound 5

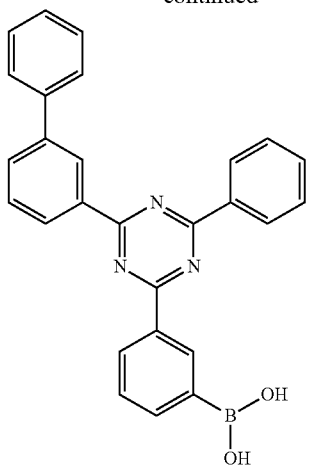

a-4

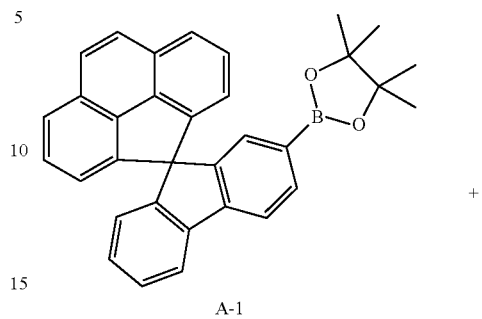

A-1

+

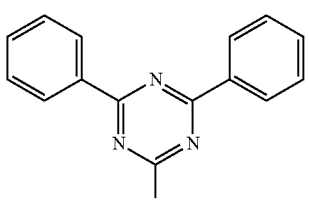

a-5

→

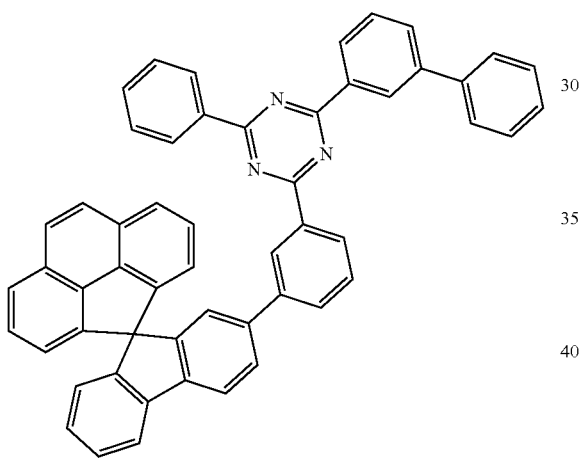

4

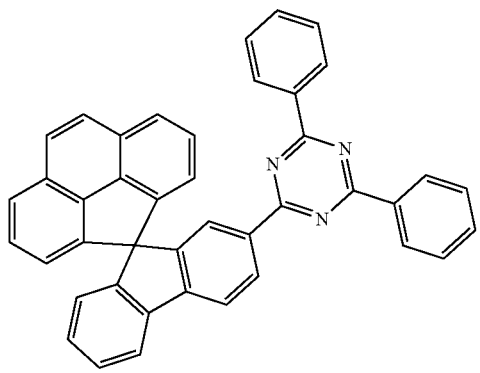

5

Compound A (7.50 g, 20.05 mmol) and Compound a-4 (9.03 g, 21.06 mmol) were completely dissolved in tetrahydrofuran (220 ml) in a 500-ml round bottom flask under a nitrogen atmosphere, to which a 2 M aqueous potassium carbonate solution (110 ml) was added and tetrakis-(triphenylphosphine)-palladium (0.70 g, 0.60 mmol) was added, and then the resulting mixture was heated and stirred for 5 hours. The temperature was lowered to room temperature, the aqueous layer was removed, and the resulting product was dried over anhydrous magnesium sulfate, and then concentrated under reduced pressure, and recrystallized with ethyl acetate (320 ml) to prepare Compound 4 (9.11 g, yield: 63%).

MS: $[M+H]^+=724$

Compound A-1 (15.58 g, 33.43 mmol) and Compound a-5 (8.50 g, 31.84 mmol) were completely dissolved in tetrahydrofuran (240 ml) in a 500-ml round bottom flask under a nitrogen atmosphere, to which a 2 M aqueous potassium carbonate solution (120 ml) was added and tetrakis-(triphenylphosphine)-palladium (1.10 g, 0.96 mmol) was added, and then the resulting mixture was heated and stirred for 4 hours. The temperature was lowered to room temperature, the aqueous layer was removed, and the resulting product was dried over anhydrous magnesium sulfate, and then concentrated under reduced pressure, and recrystallized with ethyl acetate (280 ml) to prepare Compound 5 (11.24 g, yield: 62%).

MS: $[M+H]^+=572$

Example 6: Preparation of Compound 6

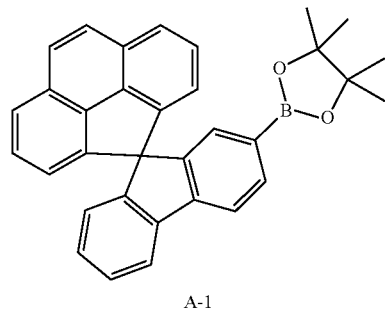
A-1

+

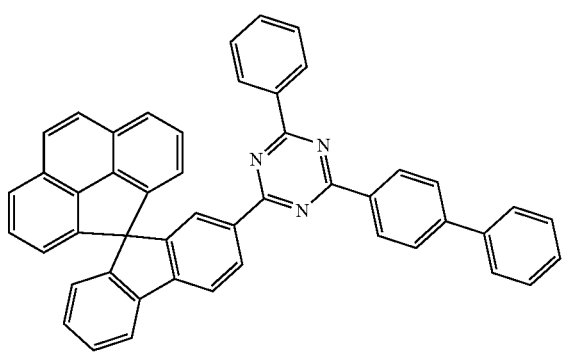
a-5

→

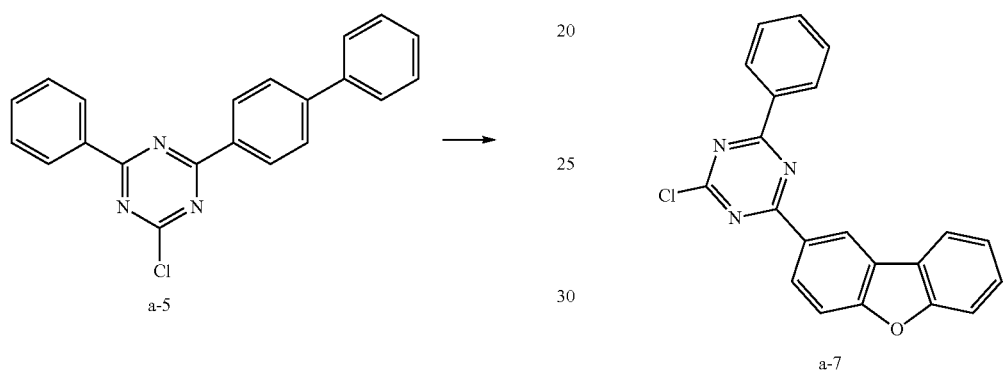
6

Compound A-1 (12.13 g, 26.02 mmol) and Compound a-6 (8.50 g, 24.78 mmol) were completely dissolved in tetrahydrofuran (260 ml) in a 500-ml round bottom flask under a nitrogen atmosphere, to which a 2 M aqueous potassium carbonate solution (130 ml) was added and tetrakis-(triphenylphosphine)-palladium (0.86 g, 0.74 mmol) was added, and then the resulting mixture was heated and stirred for 5 hours. The temperature was lowered to room temperature, the aqueous layer was removed, and the resulting product was dried over anhydrous magnesium sulfate, and then concentrated under reduced pressure, and recrystallized with ethyl acetate (270 ml) to prepare Compound 6 (10.67 g, yield: 66%).

MS: $[M+H]^+=648$

Example 7: Preparation of Compound 7

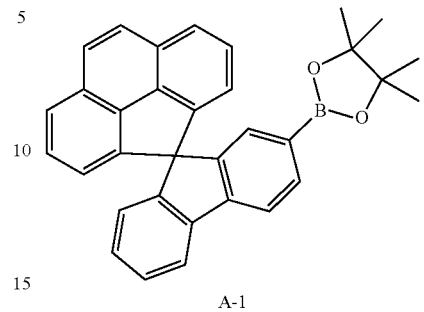
A-1

+

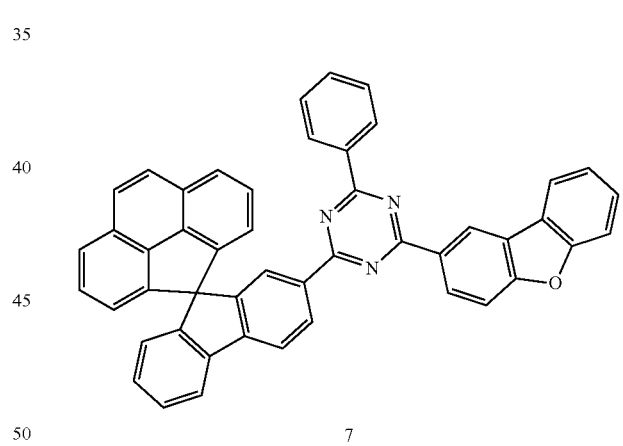
a-7

→

7

Compound A-1 (10.28 g, 22.06 mmol) and Compound a-7 (7.50 g, 21.01 mmol) were completely dissolved in tetrahydrofuran (280 ml) in a 500-ml round bottom flask under a nitrogen atmosphere, to which a 2 M aqueous potassium carbonate solution (140 ml) was added and tetrakis-(triphenylphosphine)-palladium (0.73 g, 0.63 mmol) was added, and then the resulting mixture was heated and stirred for 5 hours. The temperature was lowered to room temperature, the aqueous layer was removed, and the resulting product was dried over anhydrous magnesium sulfate, and then concentrated under reduced pressure, and recrystallized with ethyl acetate (310 ml) to prepare Compound 7 (8.84 g, yield: 64%).

MS: $[M+H]^+=662$

Example 8: Preparation of Compound 8

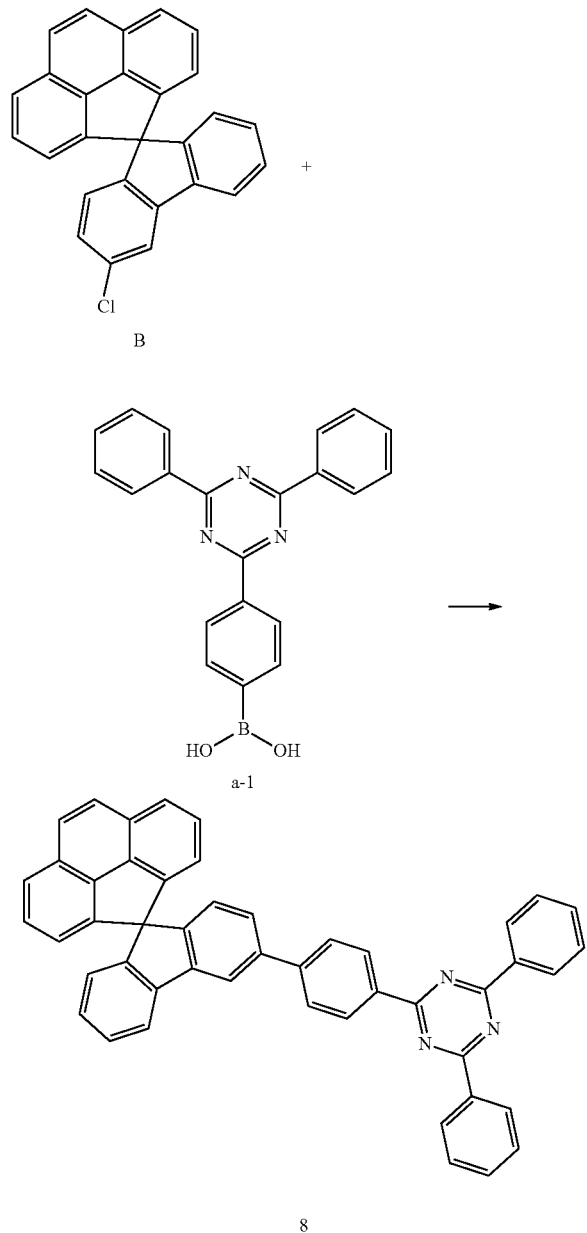

Compound B (8.50 g, 23.81 mmol) and Compound a-1 (11.65 g, 25.01 mmol) were completely dissolved in tetrahydrofuran (280 ml) in a 500-ml round bottom flask under a nitrogen atmosphere, to which a 2 M aqueous potassium carbonate solution (140 ml) was added and tetrakis-(triphenylphosphine)-palladium (0.83 g, 0.71 mmol) was added, and then the resulting mixture was heated and stirred for 4 hours. The temperature was lowered to room temperature, the aqueous layer was removed, and the resulting product was dried over anhydrous magnesium sulfate, and then concentrated under reduced pressure, and recrystallized with ethyl acetate (280 ml) to prepare Compound 8 (10.22 g, yield: 65%).

MS: $[M+H]^+=648$

Example 9: Preparation of Compound 9

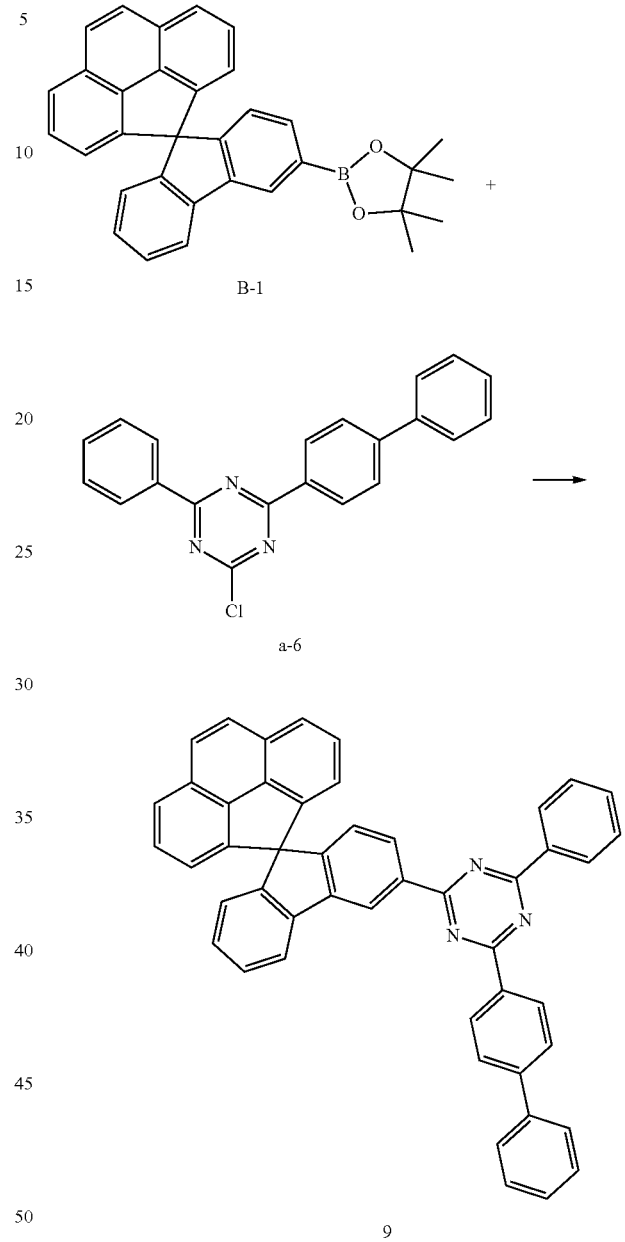

Compound B-1 (10.70 g, 22.96 mmol) and Compound a-6 (7.50 g, 21.87 mmol) were completely dissolved in tetrahydrofuran (180 ml) in a 500-ml round bottom flask under a nitrogen atmosphere, to which a 2 M aqueous potassium carbonate solution (90 ml) was added and tetrakis-(triphenylphosphine)palladium (0.76 g, 0.66 mmol) was added, and then the resulting mixture was heated and stirred for 4 hours. The temperature was lowered to room temperature, the aqueous layer was removed, and the resulting product was dried over anhydrous magnesium sulfate, and then concentrated under reduced pressure, and recrystallized with ethyl acetate (280 ml) to prepare Compound 9 (8.71 g, yield: 60%).

MS: $[M+H]^+=650$

Example 10: Preparation of Compound 10

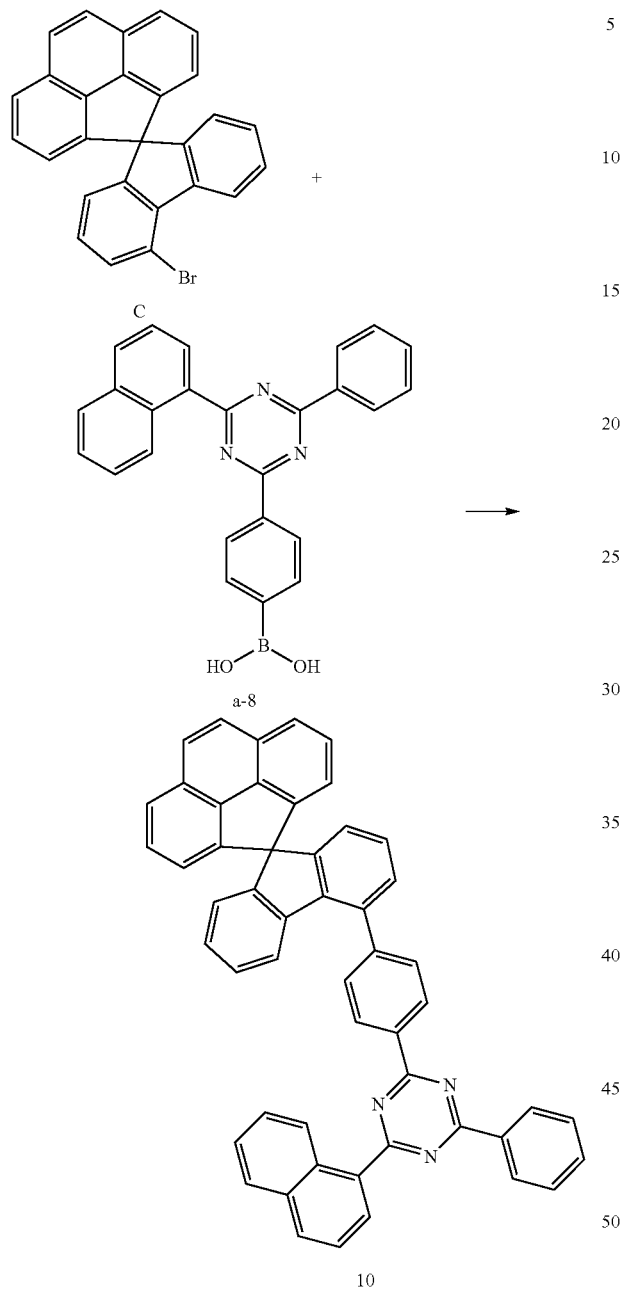

Compound C (9.50 g, 22.73 mmol) and Compound a-8 (9.62 g, 23.86 mmol) were completely dissolved in tetrahydrofuran (260 ml) in a 500-ml round bottom flask under a nitrogen atmosphere, to which a 2 M aqueous potassium carbonate solution (130 ml) was added and tetrakis-(triphenylphosphine)-palladium (0.79 g, 0.68 mmol) was added, and then the resulting mixture was heated and stirred for 4 hours. The temperature was lowered to room temperature, the aqueous layer was removed, and the resulting product was dried over anhydrous magnesium sulfate, and then concentrated under reduced pressure, and recrystallized with ethyl acetate (240 ml) to prepare Compound 10 (9.82 g, yield: 62%).

MS: [M+H]$^+$=698

Example 11: Preparation of Compound 11

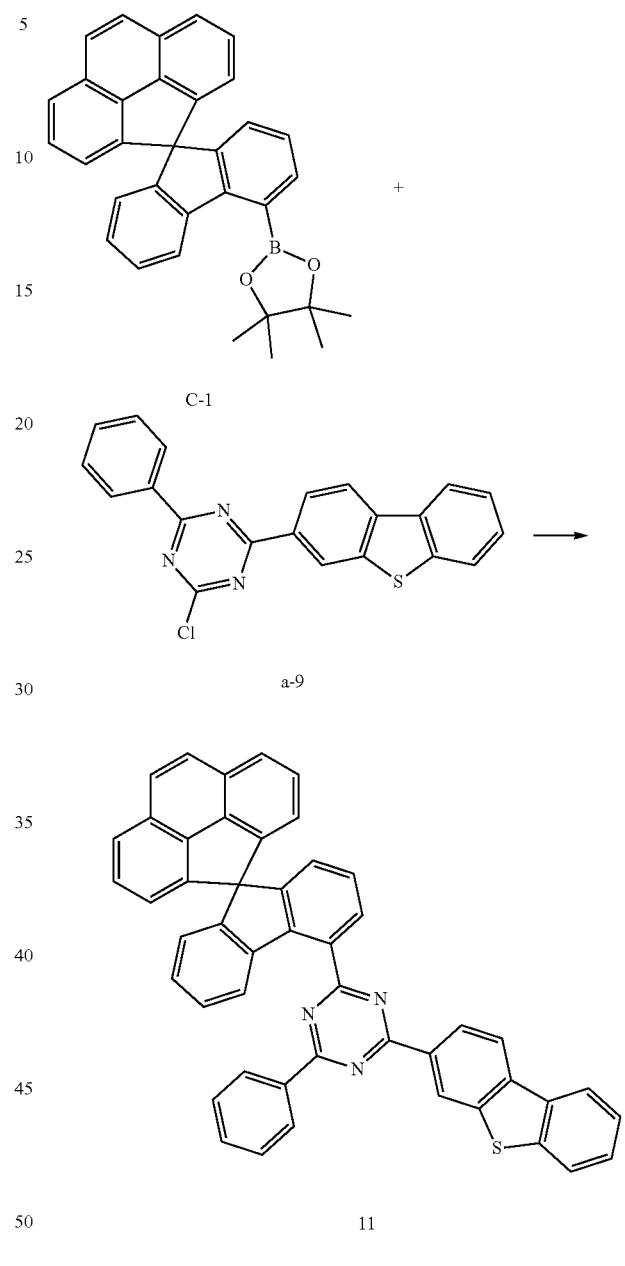

Compound C-1 (8.51 g, 21.11 mmol) and Compound a-9 (4.63 g, 9.91 mmol) were completely dissolved in tetrahydrofuran (260 ml) in a 500-ml round bottom flask under a nitrogen atmosphere, to which a 2 M aqueous potassium carbonate solution (130 ml) was added and tetrakis-(triphenylphosphine)-palladium (0.70 g, 0.60 mmol) was added, and then the resulting mixture was heated and stirred for 5 hours. The temperature was lowered to room temperature, the aqueous layer was removed, and the resulting product was dried over anhydrous magnesium sulfate, and then concentrated under reduced pressure, and recrystallized with ethyl acetate (310 ml) to prepare Compound 11 (7.85 g, yield: 58%).

MS: [M+H]$^+$=678

Experimental Examples

Experimental Example 1

A glass substrate on which ITO (indium tin oxide) was coated as a thin film to a thickness of 1,000 Å was put into distilled water in which a detergent was dissolved, and ultrasonically cleaned. In this case, a product manufactured by Fischer Co., was used as the detergent, and as the distilled water, distilled water filtered twice using a filter manufactured by Millipore Co., was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. The substrate was cleaned for 5 minutes using oxygen plasma, and then transferred to a vacuum depositor.

On the ITO transparent electrode which is the anode electrode thus prepared, the following compound HI1 and the following compound HI2 were thermally vacuum deposited at a ratio of 98:2 (molar ratio) to have a thickness of 100 Å, thereby forming a hole injection layer. The following compound HT1 was vacuum deposited on the hole injection layer to a thickness of 1150 Å to form a hole transfer layer. The following compound EB1 was vacuum deposited on the hole transport layer to a thickness of 50 Å to form an electron blocking layer. Then, the following compound BH and the following compound BD were vacuum deposited at a weight ratio of 25:1 on the electron blocking layer to a thickness of 200 Å to form a light emitting layer. The Compound 1 prepared in Example 1 above was vacuum deposited on the light emitting layer to a thickness of 50 Å to form a hole blocking layer. The following compound ET1 and the following compound LiQ were vacuum deposited at a ratio of 1:1 on the hole blocking layer to a thickness of 310 Å to form an electron injection and transport layer. Lithium fluoride (LiF) and aluminum were sequentially deposited to have a thickness of 12 Å and 1,000 Å, respectively, on the electron injection and transport layer, thereby forming a cathode.

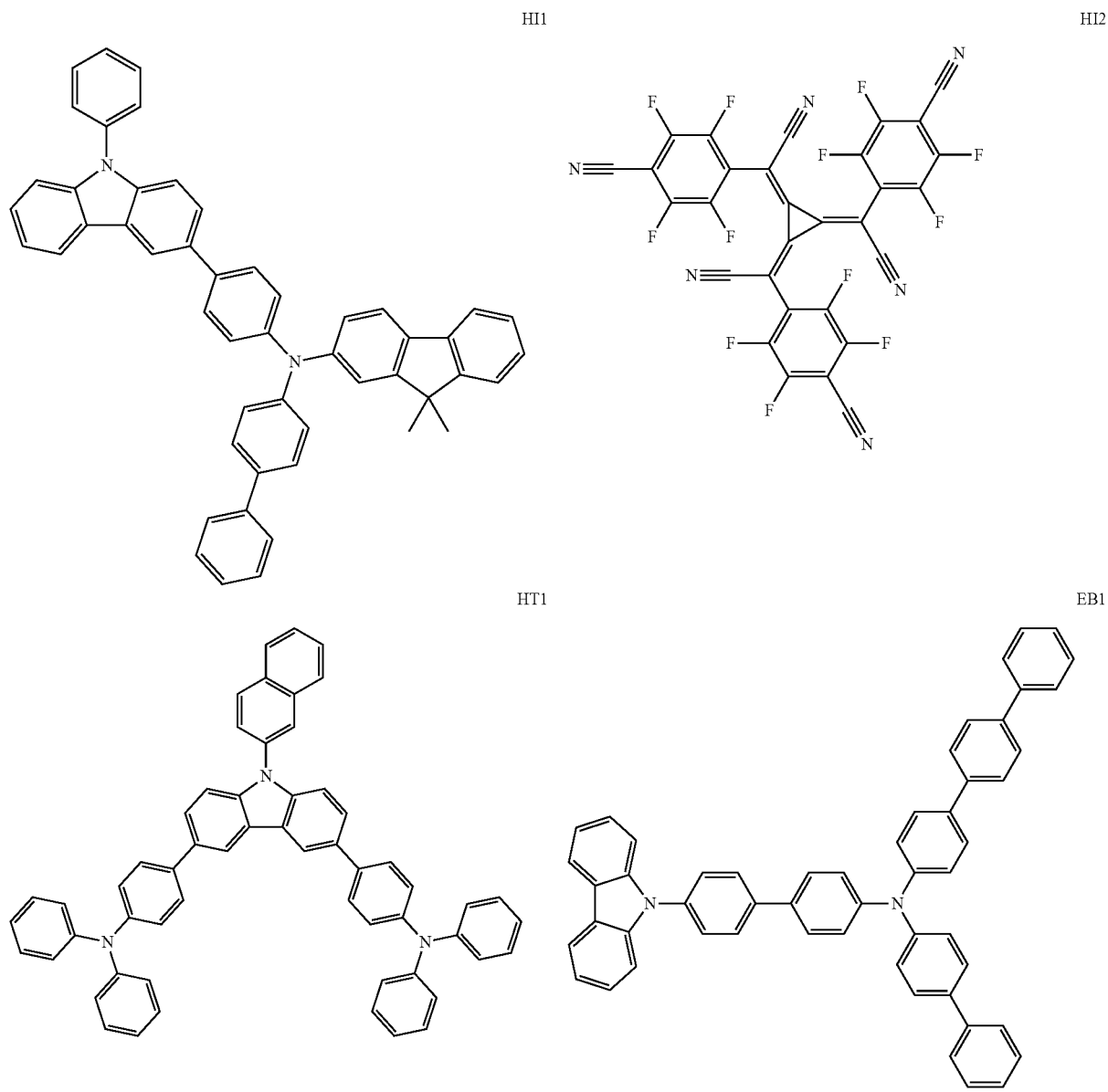

-continued

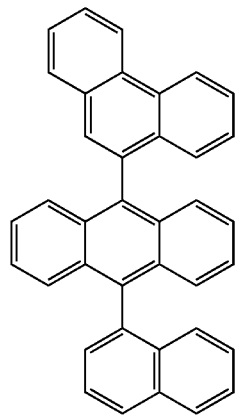
BH

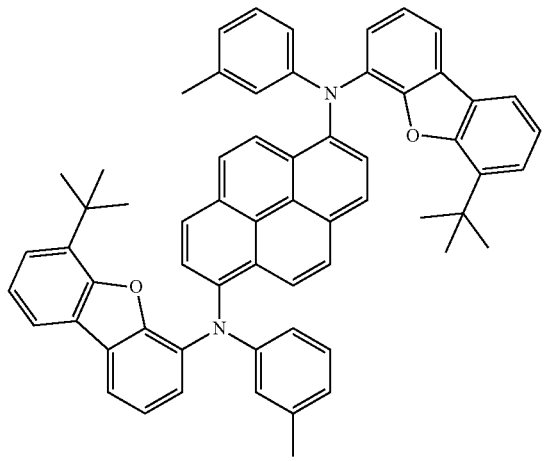
BD

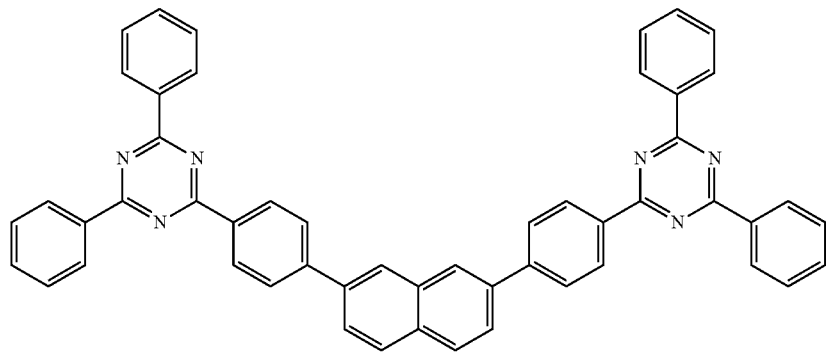
ET1

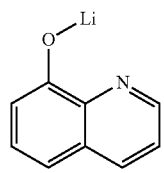
LiQ

In the above-mentioned process, the vapor deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Examples 2 to 11

An organic light emitting device was manufactured in the same manner as in Experimental Example 1, except that the compounds shown in Table 1 below were used instead of Compound 1.

Comparative Experimental Examples 1 to 3

An organic light emitting device was manufactured in the same manner as in Experimental Example 1, except that the compounds shown in Table 1 below were used instead of Compound 1. Compounds HB1, HB2 and HB3 shown in Table 1 below are as follows:

HB1

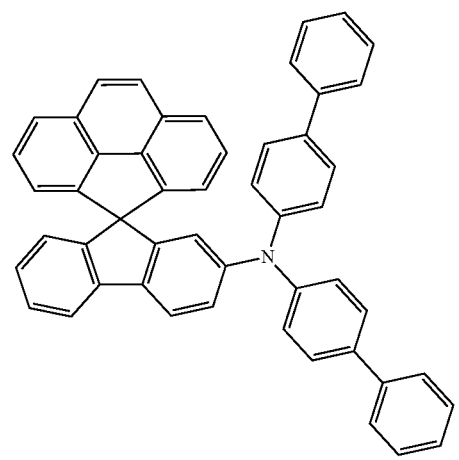

HB2

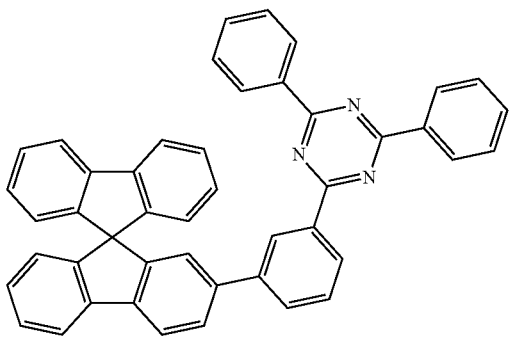

HB3

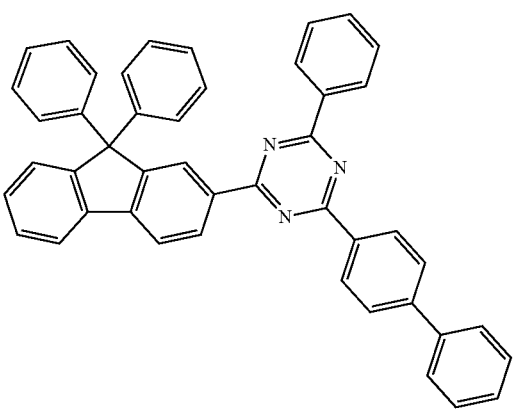

The voltage, efficiency, color coordinate, and lifetime were measured by applying a current to the organic light emitting devices manufactured in the Experimental Examples and Comparative Experimental Examples, and the results are shown in Table 1 below. T95 means the time required for the luminance to be reduced to 95% of the initial luminance (1600 nit).

TABLE 1

|  | Compound (hole blocking layer) | Voltage (V@10 mA/cm$^2$) | Efficiency (cd/A @10 mA/cm$^2$) | Color Coordinate (x, y) | T95 (hr @10 mA/cm$^2$) |
|---|---|---|---|---|---|
| Experimental Example 1 | Compound 1 | 4.47 | 6.59 | (0.145, 0.042) | 255 |
| Experimental Example 2 | Compound 2 | 4.48 | 6.54 | (0.144, 0.045) | 265 |
| Experimental Example 3 | Compound 3 | 4.43 | 6.58 | (0.146, 0.046) | 255 |
| Experimental Example 4 | Compound 4 | 4.45 | 6.54 | (0.147, 0.047) | 240 |
| Experimental Example 5 | Compound 5 | 4.42 | 6.56 | (0.146, 0.044) | 250 |
| Experimental Example 6 | Compound 6 | 4.44 | 6.52 | (0.144, 0.045) | 265 |
| Experimental Example 7 | Compound 7 | 4.45 | 6.58 | (0.145, 0.046) | 255 |
| Experimental Example 8 | Compound 8 | 4.55 | 6.49 | (0.146, 0.047) | 245 |
| Experimental Example 9 | Compound 9 | 4.51 | 6.48 | (0.146, 0.046) | 235 |
| Experimental Example 10 | Compound 10 | 4.66 | 6.34 | (0.144, 0.045) | 245 |
| Experimental Example 11 | Compound 11 | 4.67 | 6.31 | (0.145, 0.046) | 230 |
| Comparative Experimental Example 1 | Compound HB1 | 6.12 | 2.35 | (0.145, 0.045) | 15 |
| Comparative Experimental Example 2 | Compound HB2 | 4.98 | 5.23 | (0.146, 0.046) | 180 |
| Comparative Experimental Example 3 | Compound HB3 | 5.14 | 5.60 | (0.147, 0.044) | 195 |

As shown in Table 1, the organic light emitting device using the compound of the present invention as the hole blocking layer exhibited excellent characteristics in terms of efficiency, driving voltage and stability of the organic light emitting device. In particular, compared to the organic light emitting devices of Comparative Experimental Examples 2 and 3 manufactured using Compounds HB2 and HB3 in which triazine substituents are linked to 9,9'-spirobi[fluorene] and 9,9-diphenyl-9H-fluorene cores, the organic light emitting devices of Experimental Examples 1 to 11 using the compound of the present invention exhibited low voltage, high efficiency and long lifetime characteristics. In addition, the organic light emitting device of Comparative Experimental Example 1 manufactured using Compound HB-1 having a structure in which an amine-based substituent was substituted for the core of the present invention, did not exhibit these characteristics.

EXPLANATION OF SIGNS

| | |
|---|---|
| 1: substrate | 2: anode |
| 3: organic material layer | 4: cathode |
| 5: hole injection layer | 6: hole transport layer |
| 7: electron blocking layer | 8: light emitting layer |
| 9: hole blocking layer | 10: electron transport layer |
| 11: electron injection layer | |

The invention claimed is:

1. A compound of Chemical Formula 1:

Chemical Formula 1

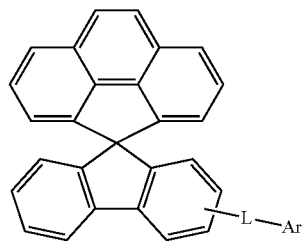

wherein in Chemical Formula 1:
L is a single bond, a substituted or unsubstituted $C_{6-60}$ arylene, or a substituted or unsubstituted $C_{2-60}$ heteroarylene containing at least one selected from the group consisting of N, O and S; and
Ar is any one selected from the group consisting of the following:

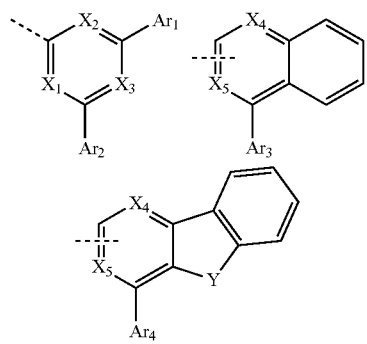

wherein:
$X_1$ to $X_3$ are N, or CH, with the proviso that at least one of $X_1$ to $X_3$ is N;
$Ar_1$ and $Ar_2$ are each independently a substituted or unsubstituted $C_{6-60}$ aryl, or a substituted or unsubstituted $C_{2-60}$ heteroaryl containing at least one selected from the group consisting of N, O and S;
$X_4$ and $X_5$ are N or CH, with the proviso that at least one of $X_4$ and $X_5$ is N;
$Ar_3$ is independently a substituted or unsubstituted $C_{6-60}$ aryl, or a substituted or unsubstituted $C_{2-60}$ heteroaryl containing at least one selected from the group consisting of N, O and S.
Y is $N(Ar_5)$, O, or S;
Ar4 is hydrogen, a substituted or unsubstituted $C_{6-60}$ aryl, or a substituted or unsubstituted $C_{2-60}$ heteroaryl containing at least one selected from the group consisting of N, O and S, and
$Ar_5$ is a substituted or unsubstituted $C_{6-60}$ aryl.

2. The compound according to claim 1,
wherein Chemical Formula 1 is one of the following Chemical Formula 1-1, 1-2 or 1-3:

Chemical Formula 1-1

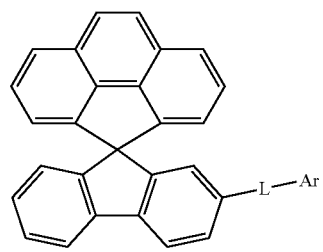

Chemical Formula 1-2

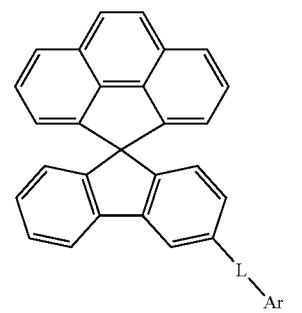

Chemical Formula 1-3

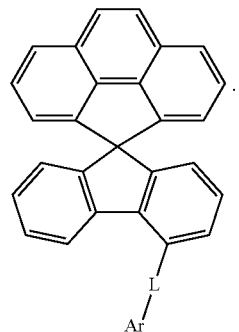

3. The compound according to claim 1,
wherein L is a single bond, phenylene, or carbazoldiyl.
4. The compound according to claim 1,
wherein $Ar_1$ and $Ar_2$ are each independently phenyl, biphenylyl, terphenylyl, naphthyl, phenanthrenyl, triphenylenyl, dibenzofuranyl, dibenzothiophenyl, or 9-phenyl-9H-carbazolyl.

5. The compound according to claim 1,
wherein $Ar_3$ is phenyl, biphenylyl, or naphthyl.
6. The compound according to claim 1,
wherein $Ar_4$ is hydrogen, phenyl, biphenylyl, or naphthyl.
7. The compound according to claim 1,
wherein $Ar_5$ is phenyl.
8. The compound according to claim 1,
wherein the compound of Chemical Formula 1 is selected from the group consisting of the following:

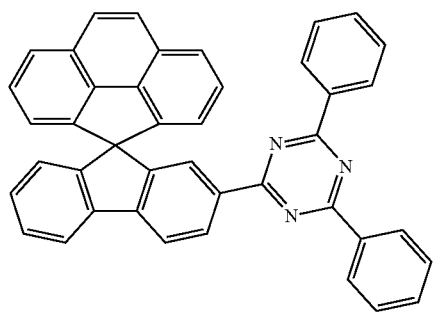

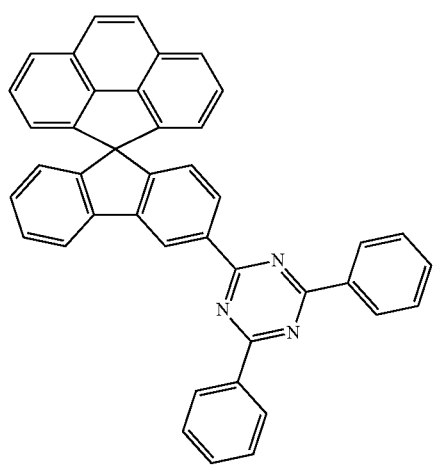

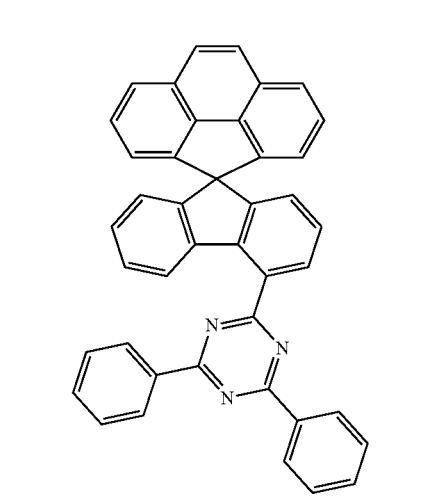

-continued

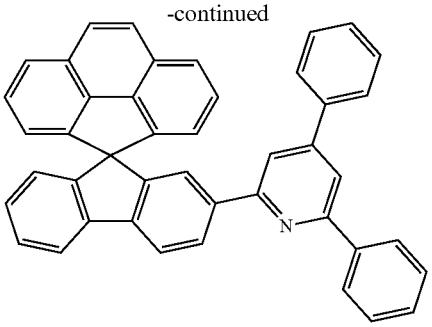

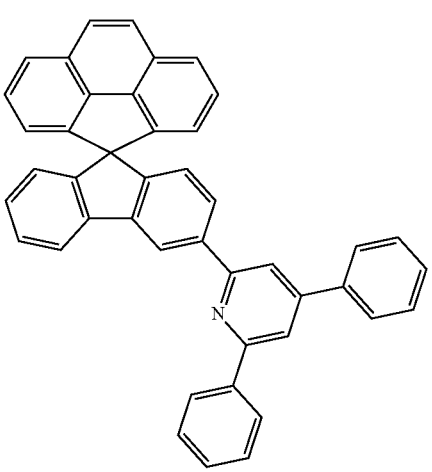

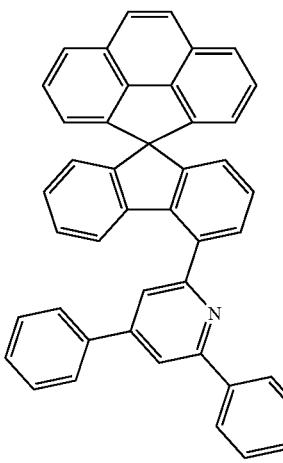

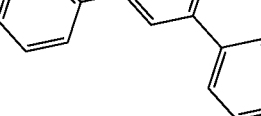

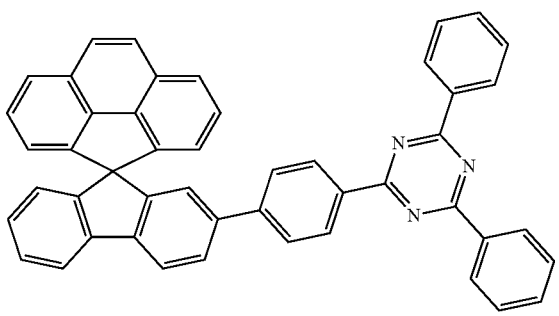

101
-continued
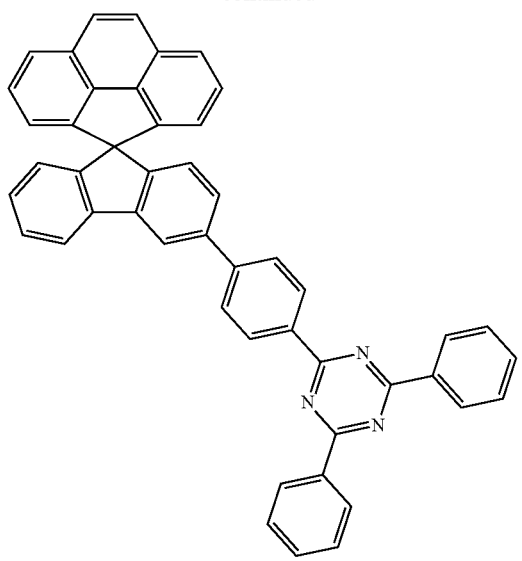
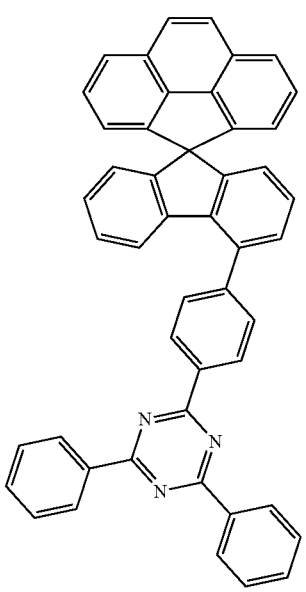
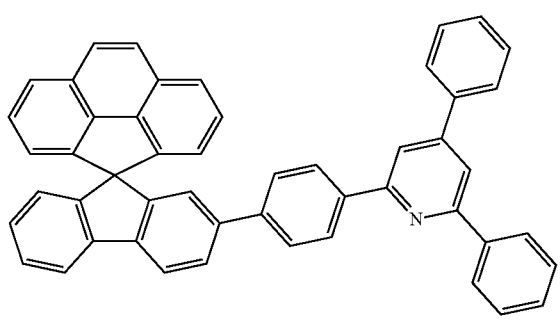
102
-continued
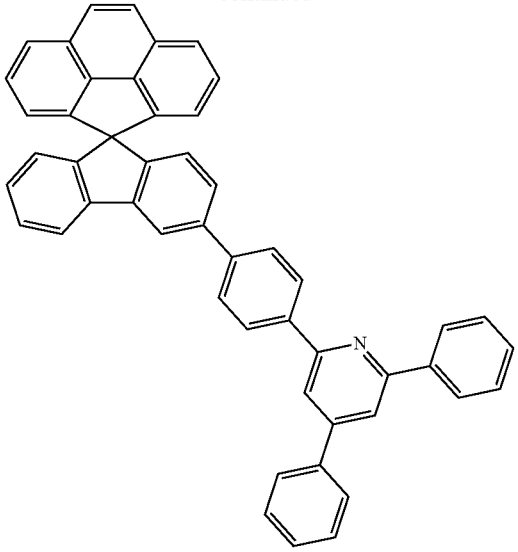
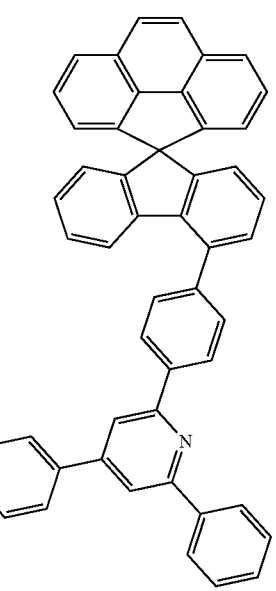
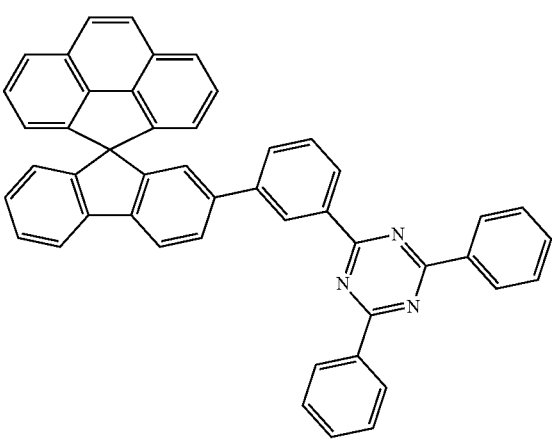

103
-continued
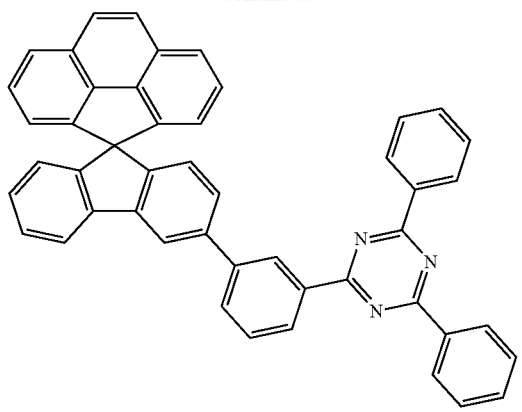
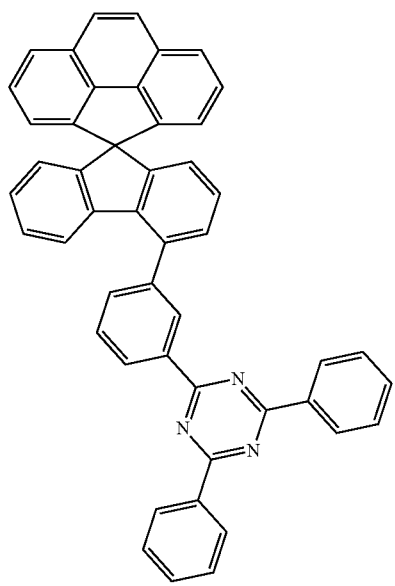
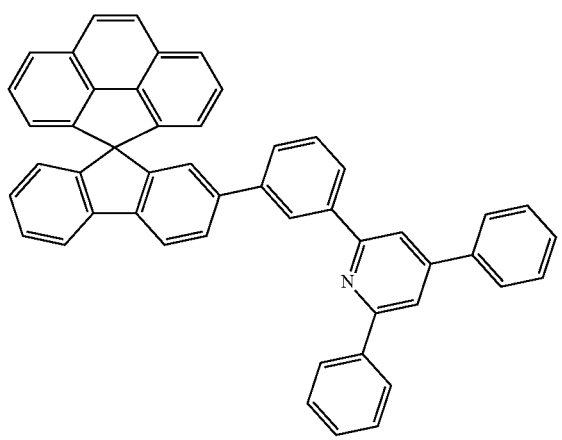
104
-continued
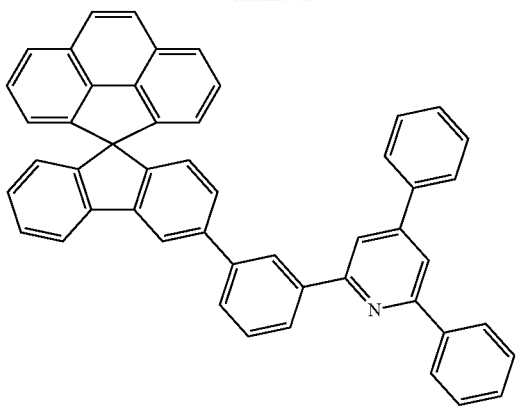
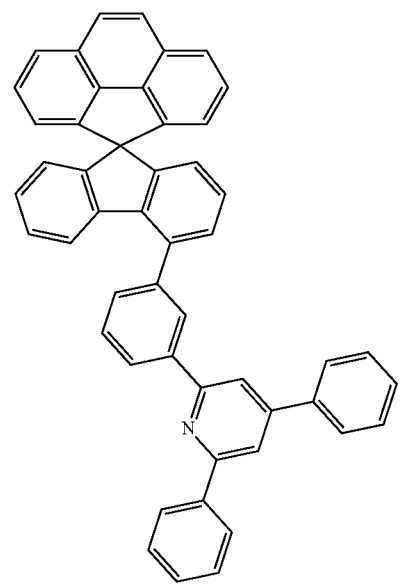
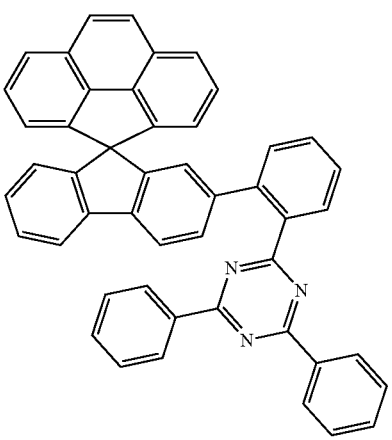

105
-continued
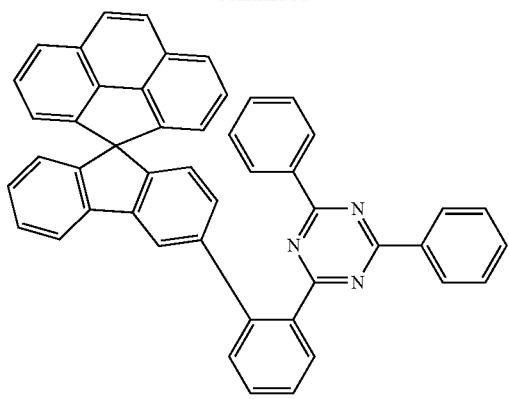
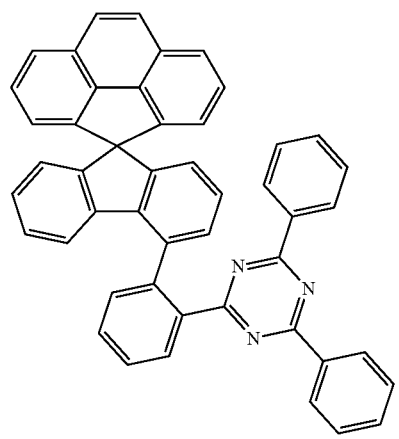
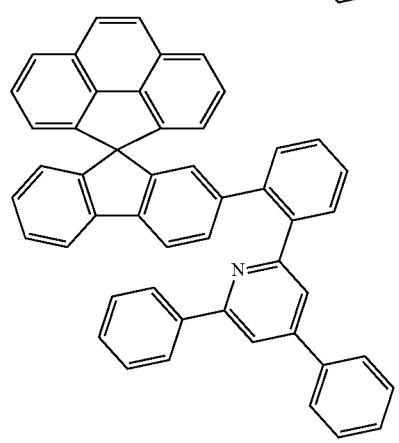
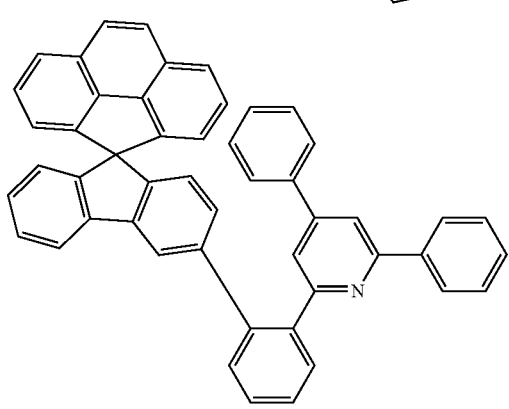
106
-continued
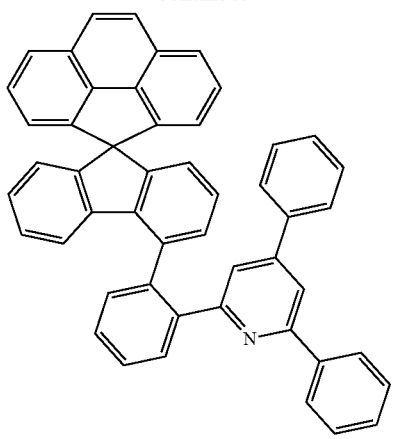
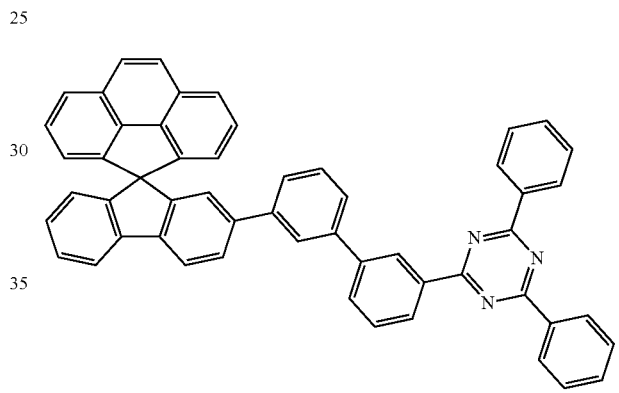
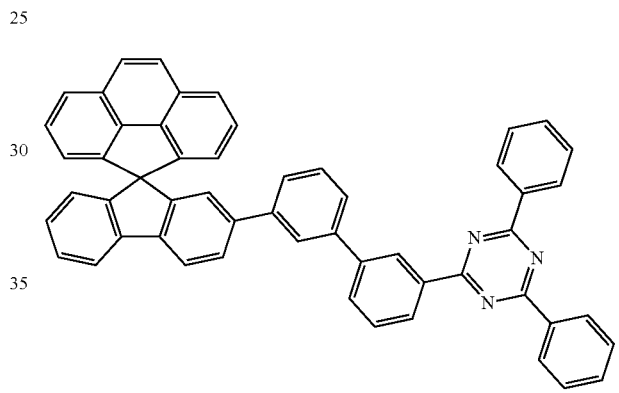

107
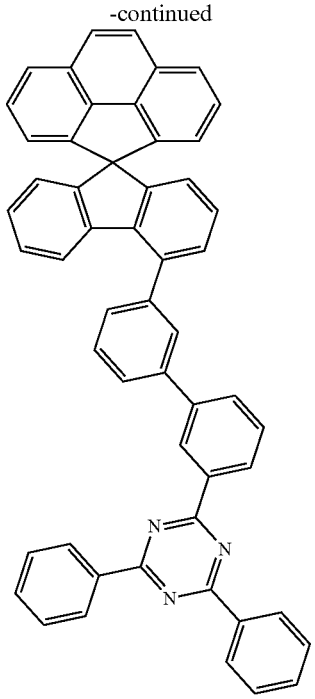
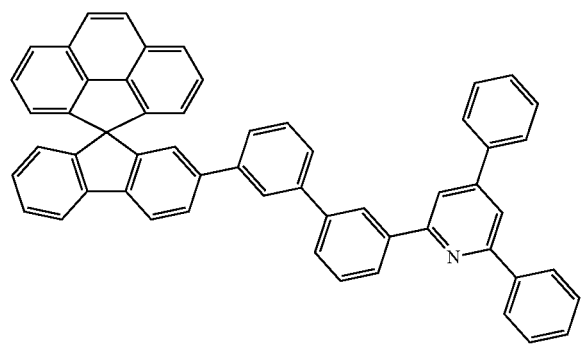
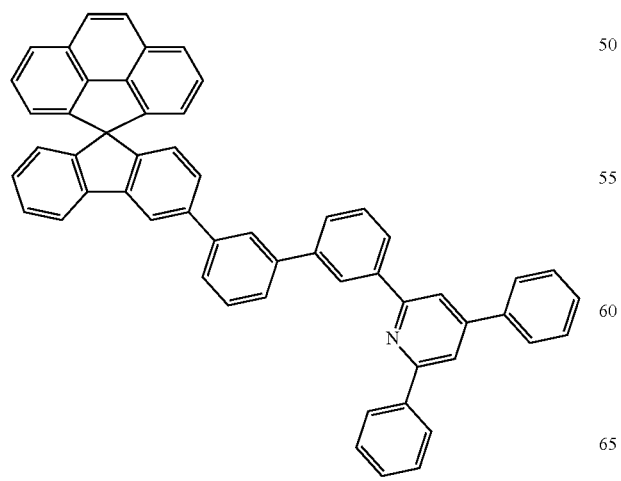
108
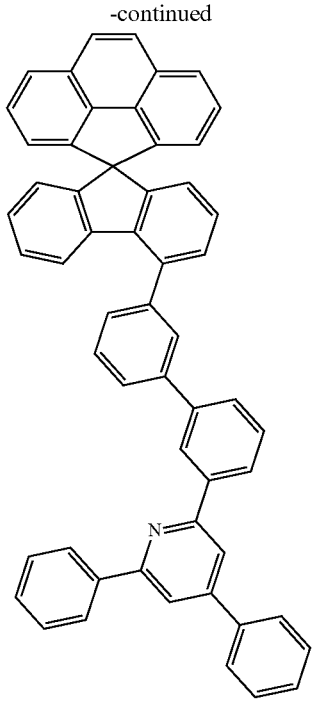
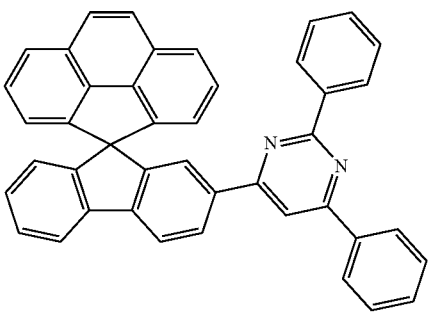
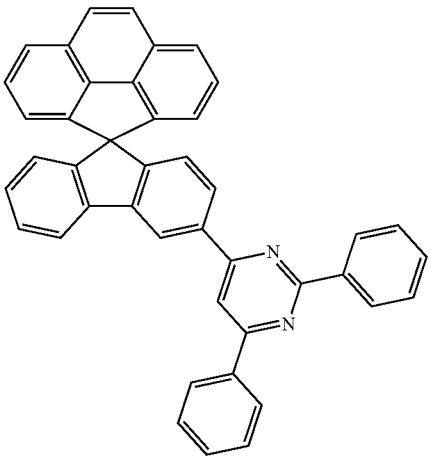

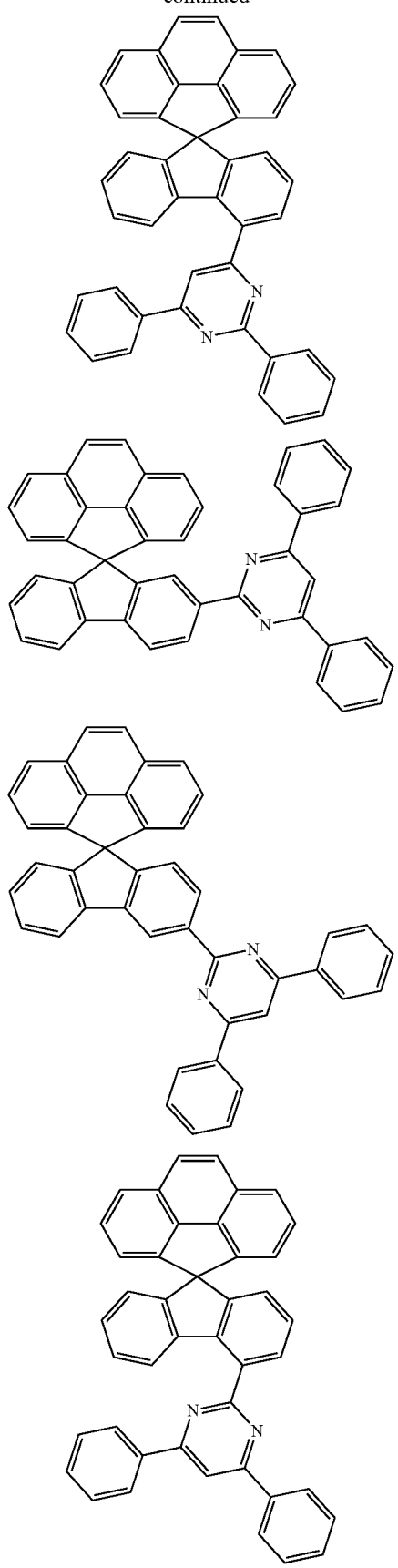
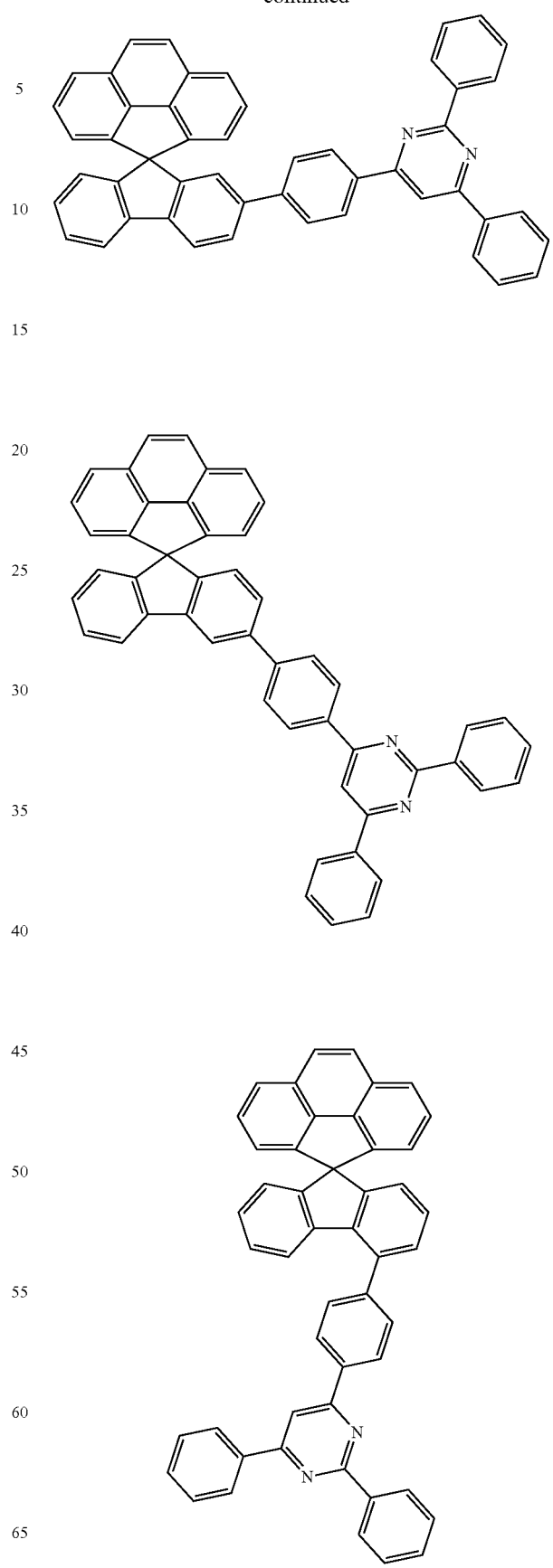

111
-continued
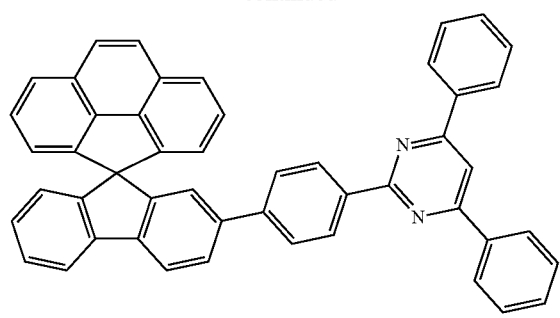
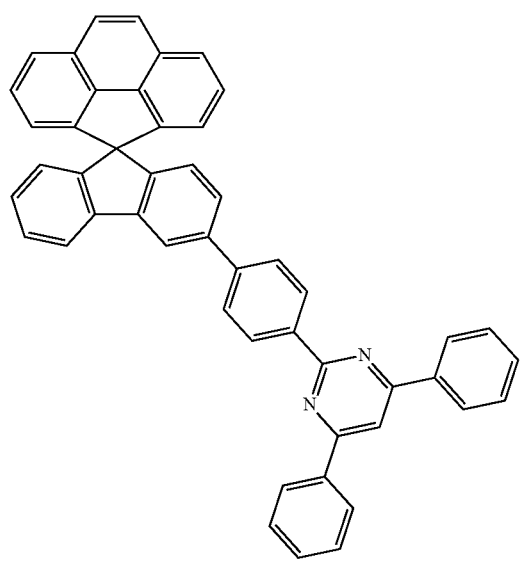
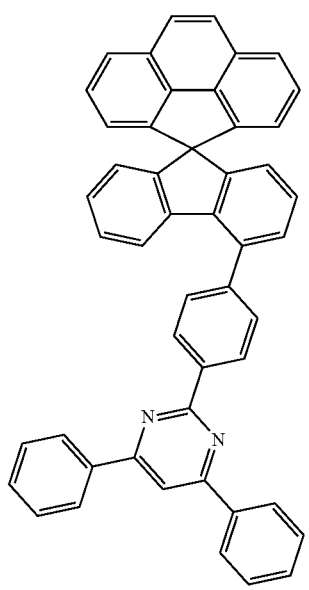
112
-continued
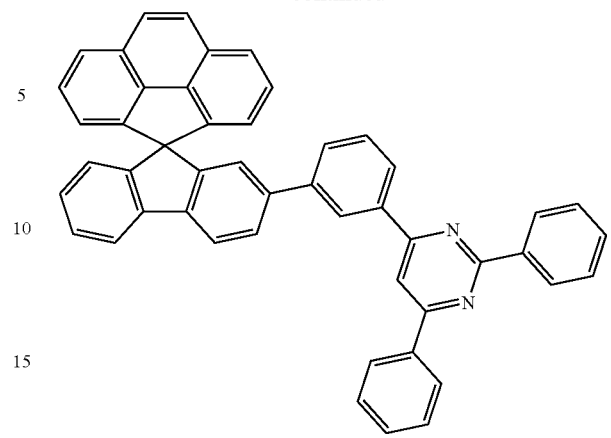
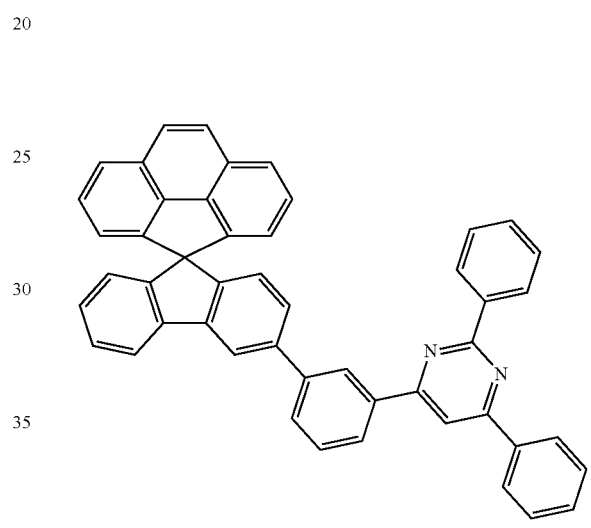
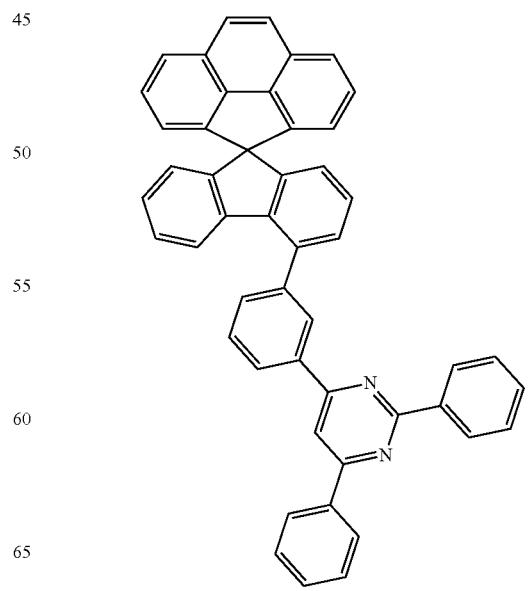

113
-continued
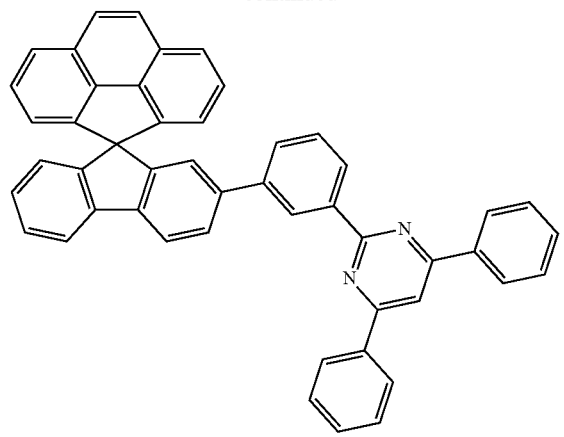
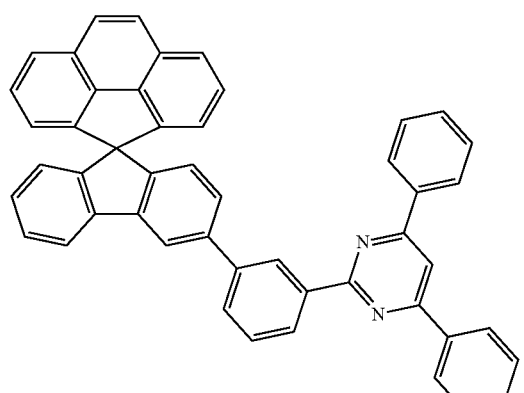
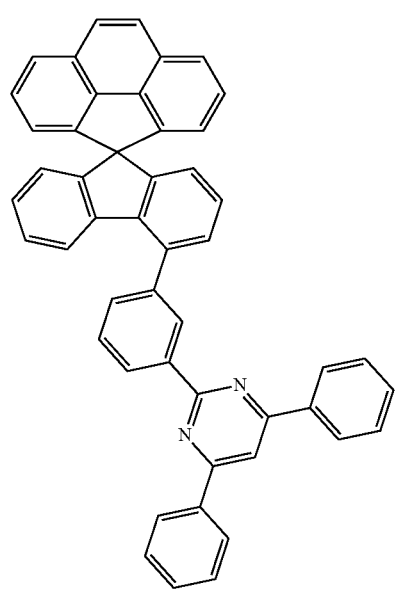
114
-continued
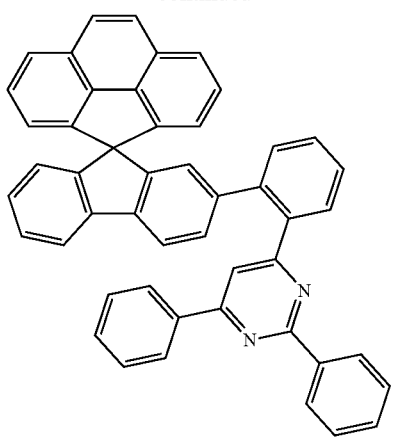
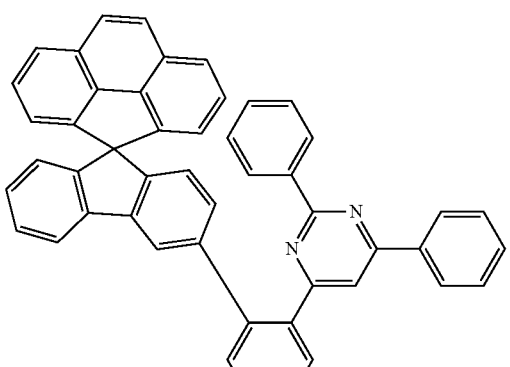
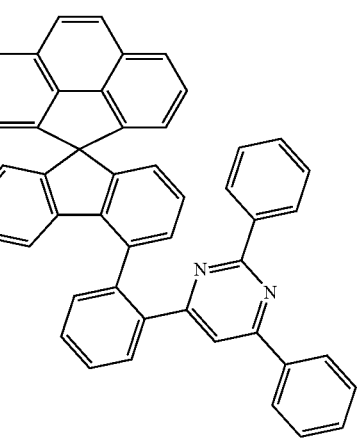
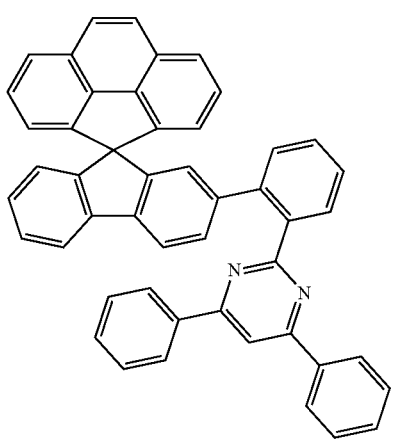

115
-continued
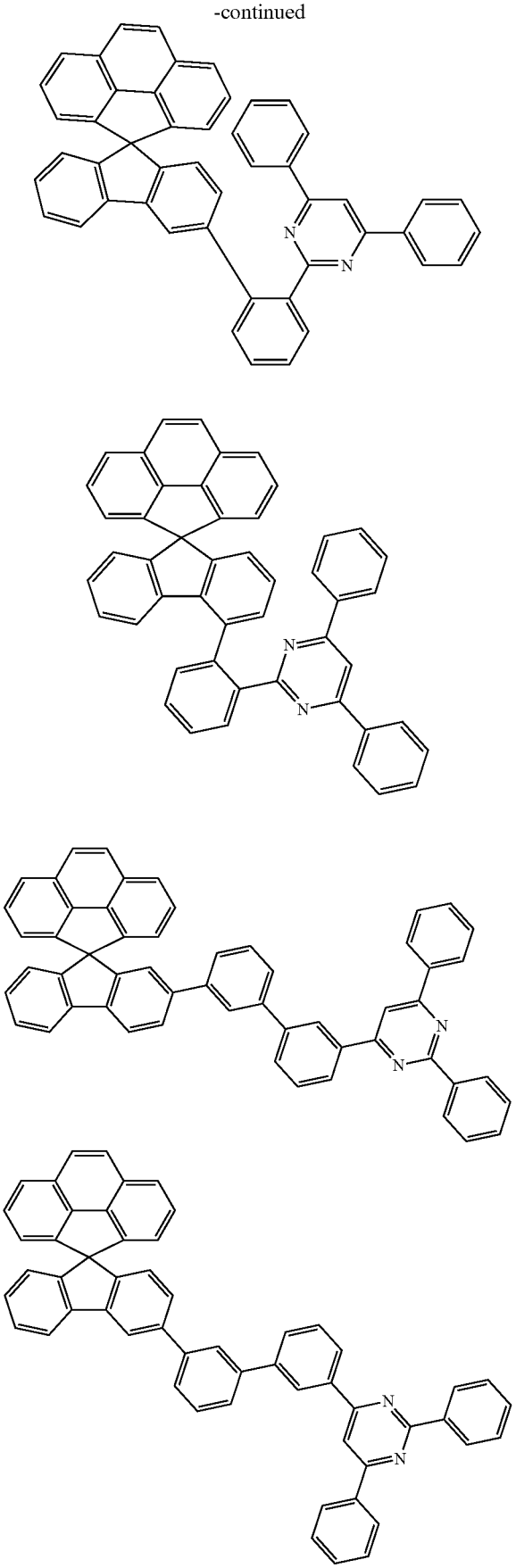
116
-continued
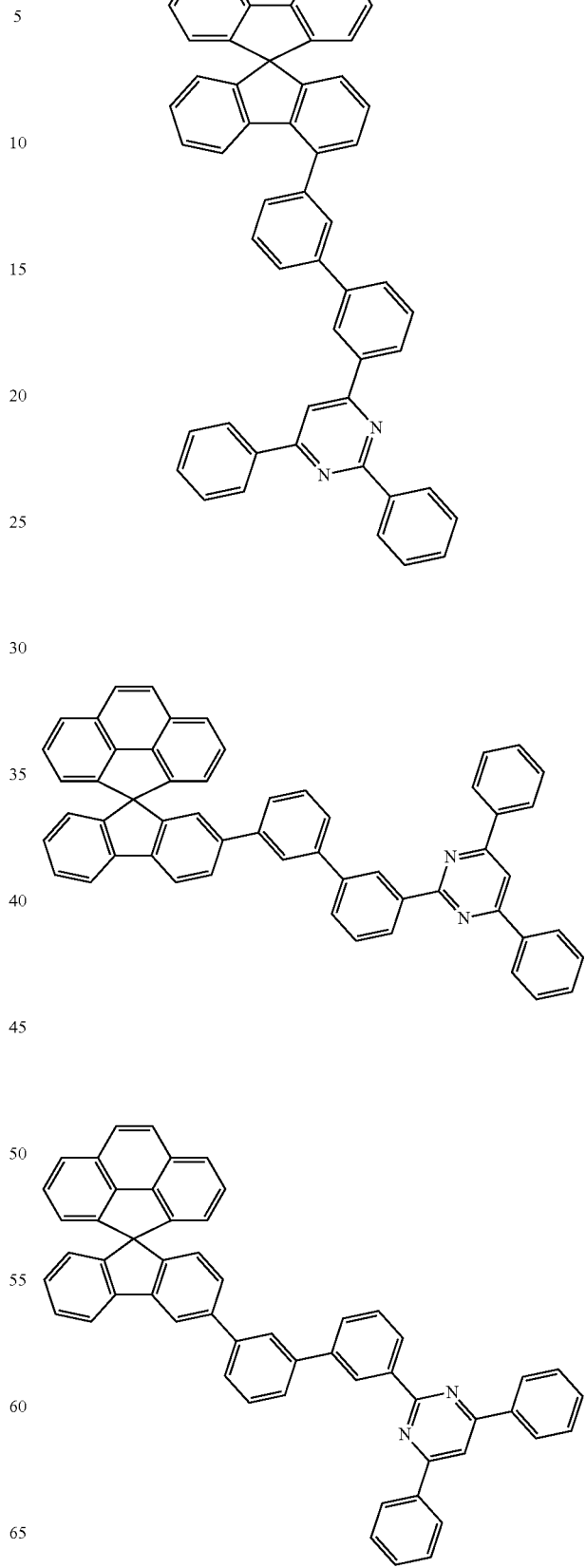

117
-continued
118
-continued
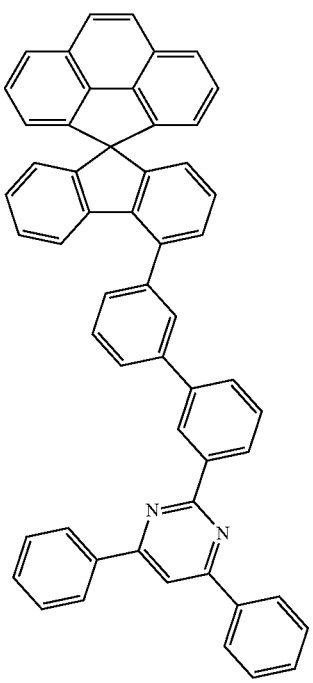
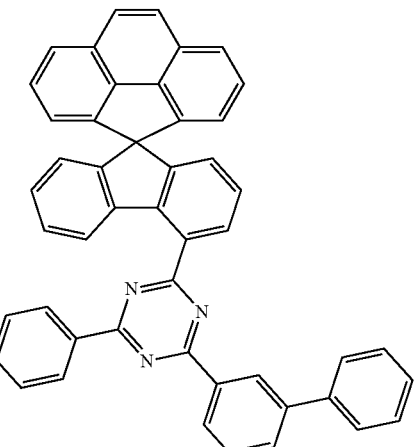
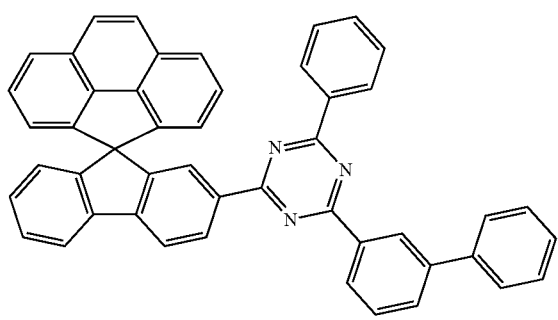
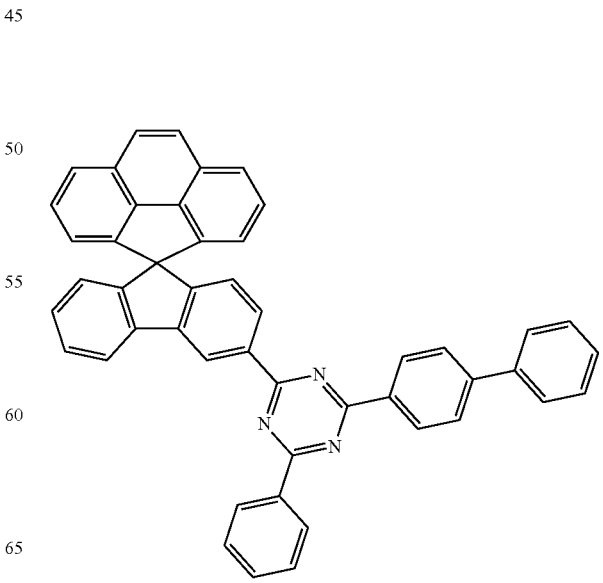

119
-continued
120
-continued
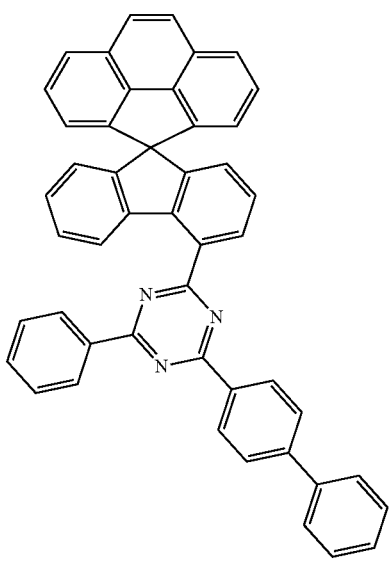
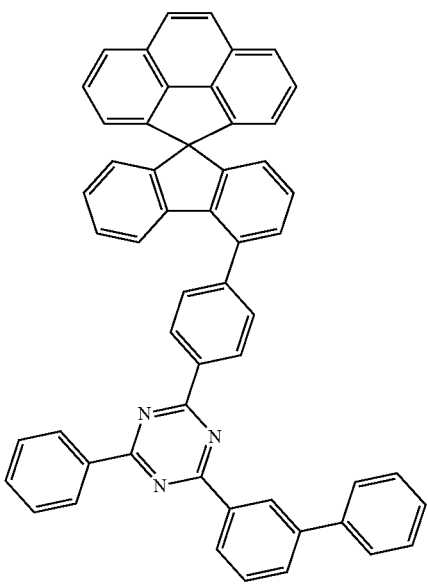
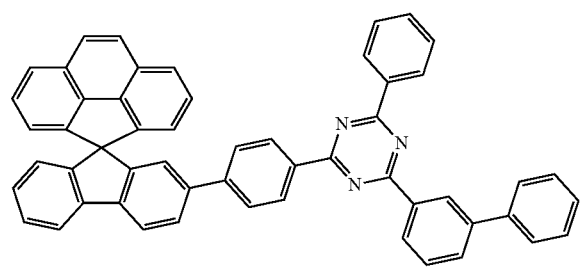
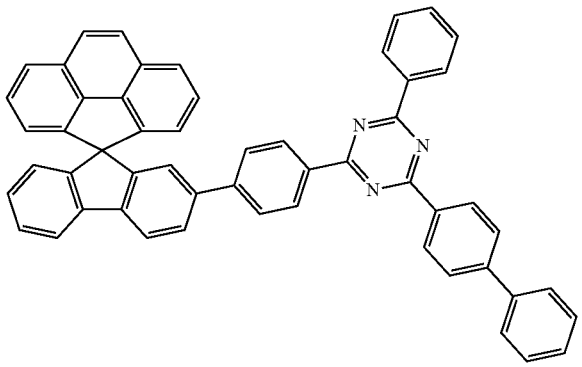
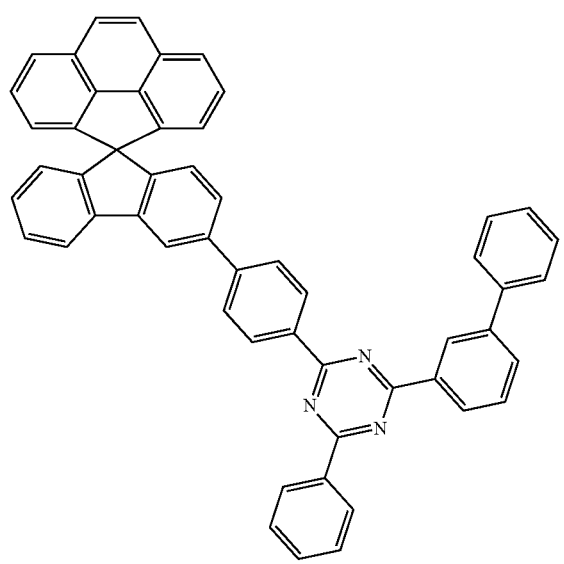
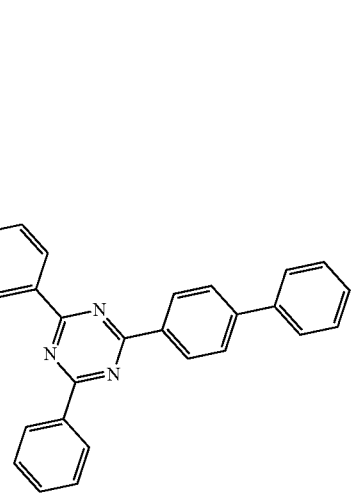

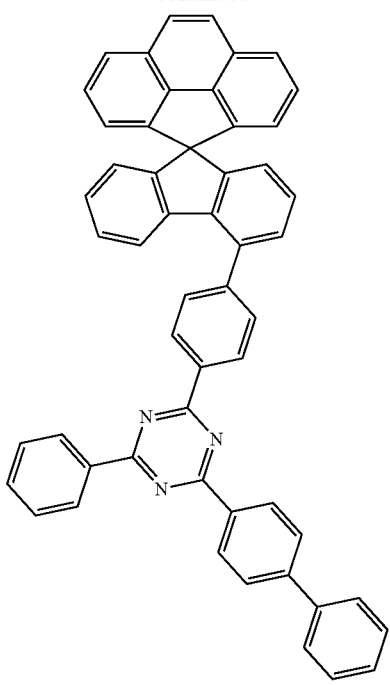
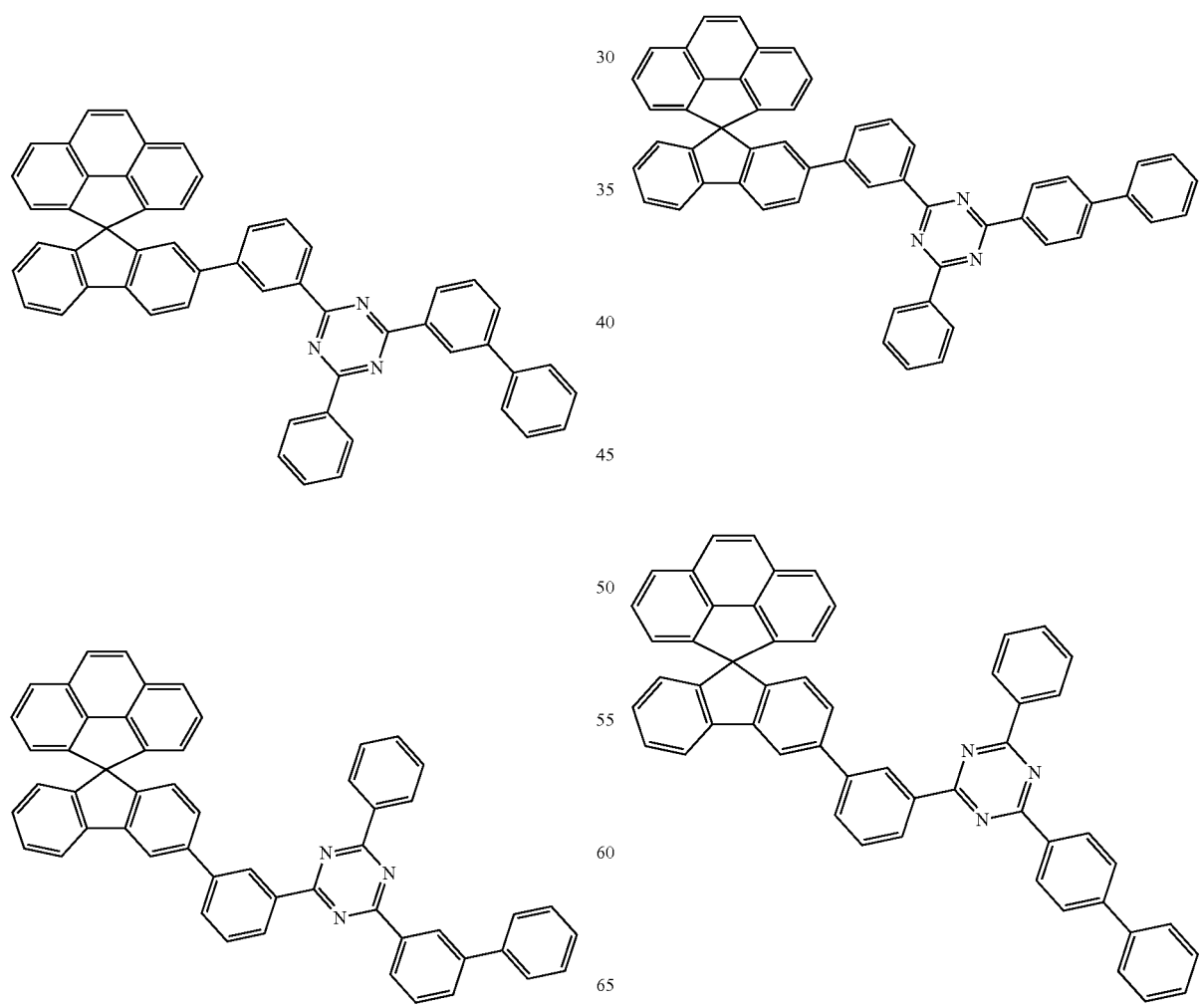

123
-continued
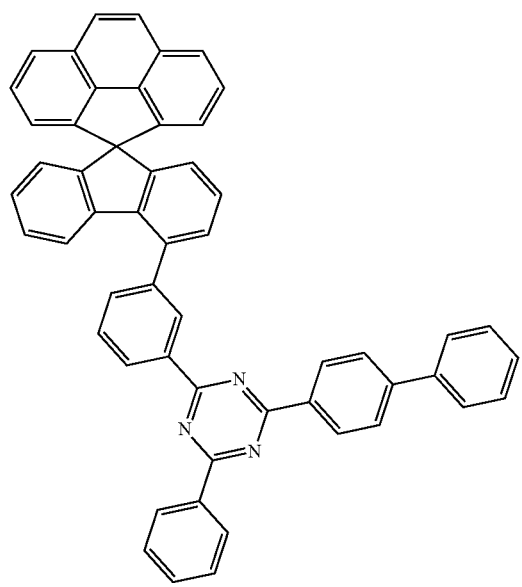
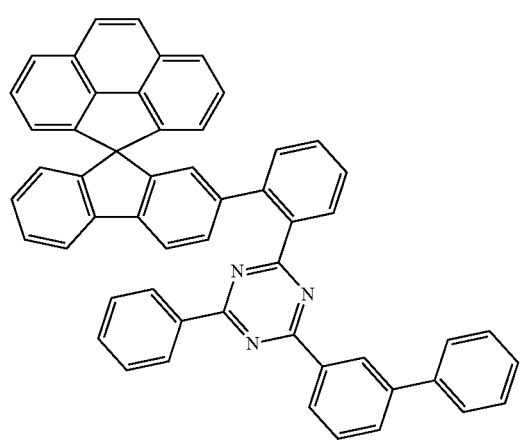
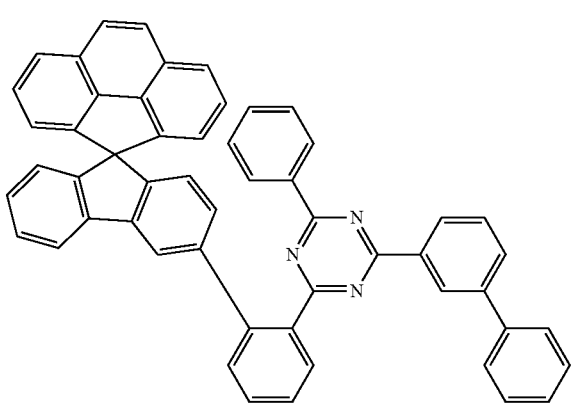
124
-continued
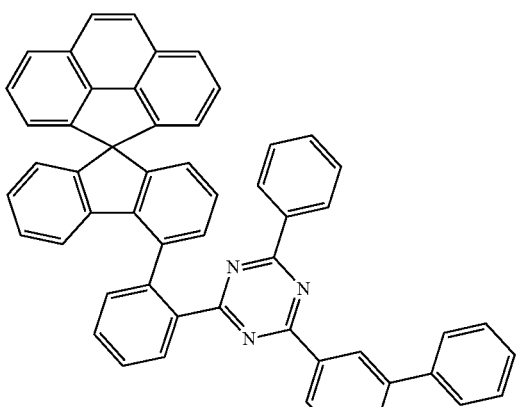
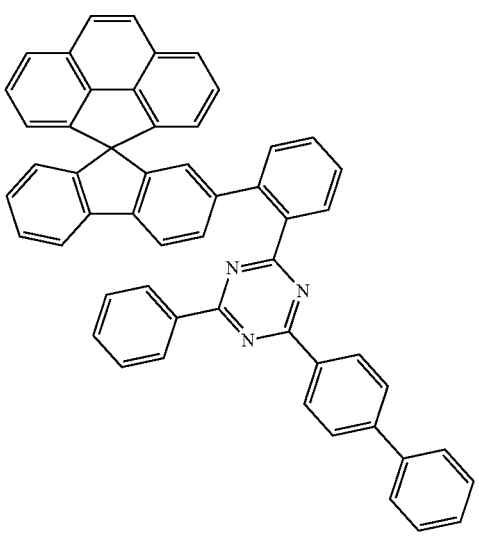
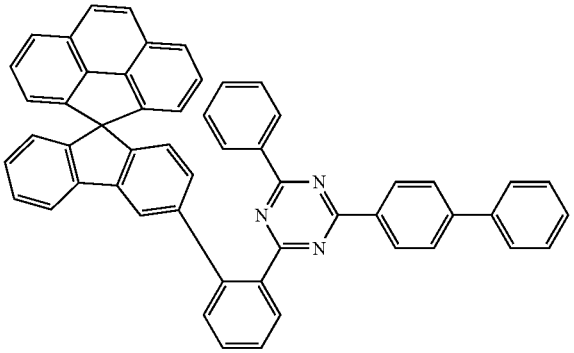

125
-continued
126
-continued
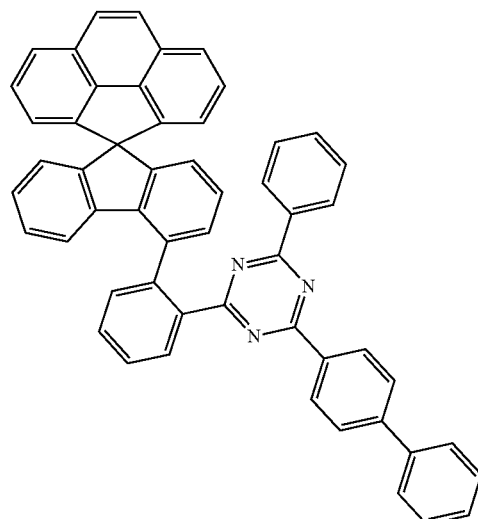
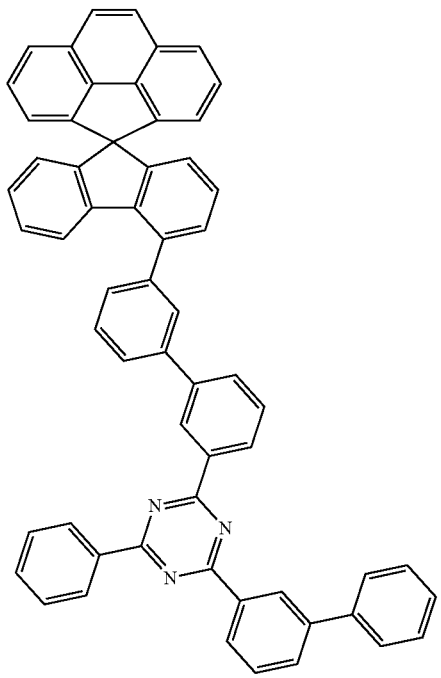
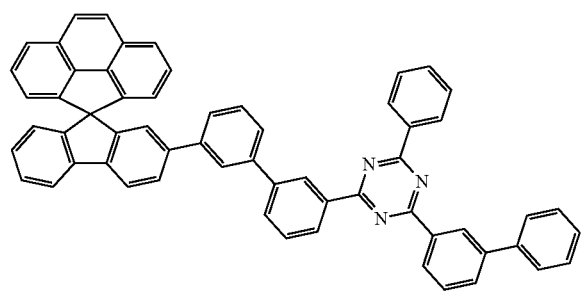
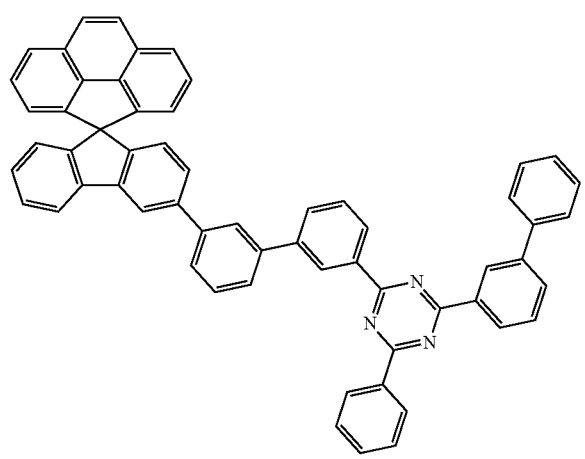
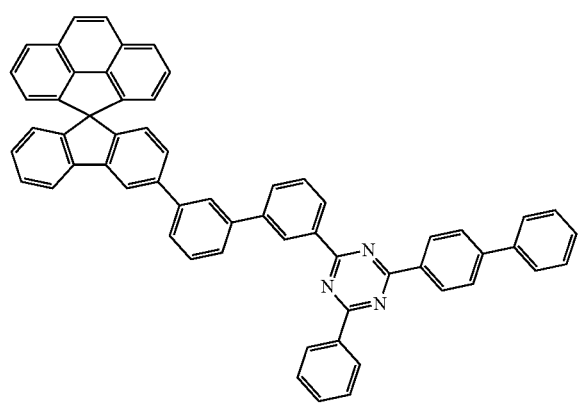

127
-continued
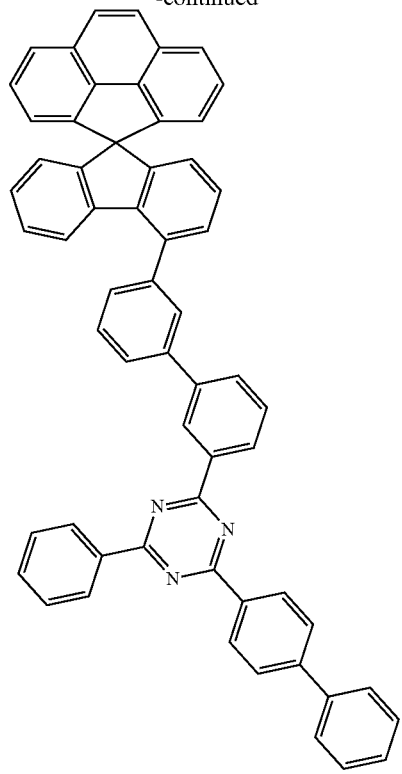
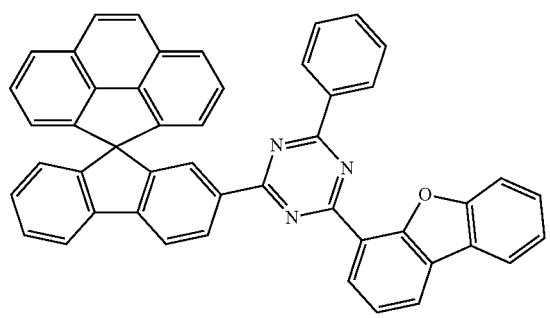
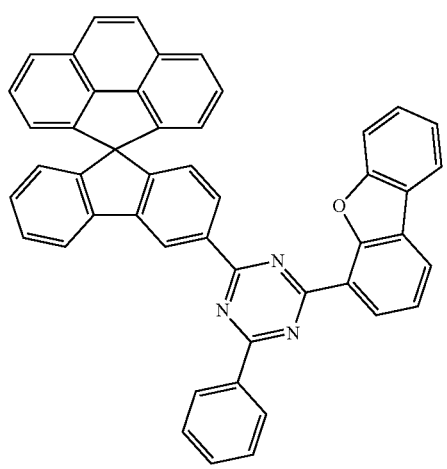
128
-continued
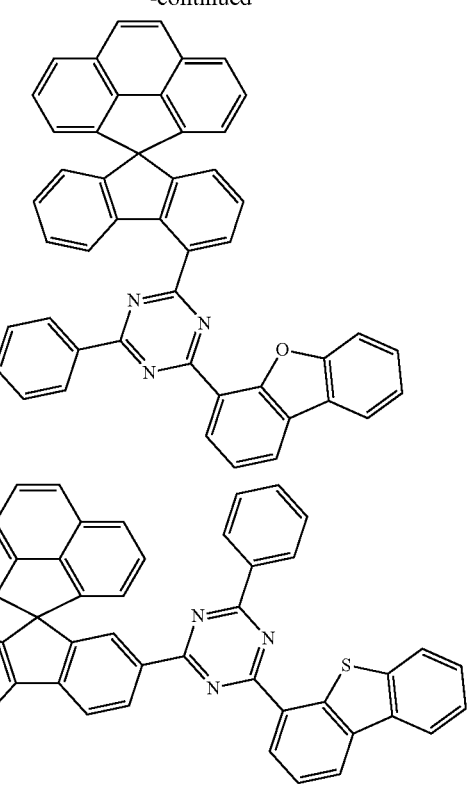
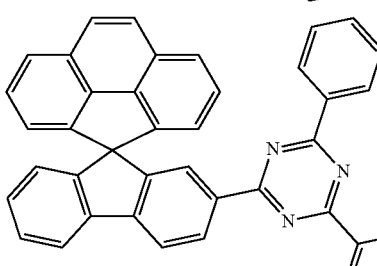
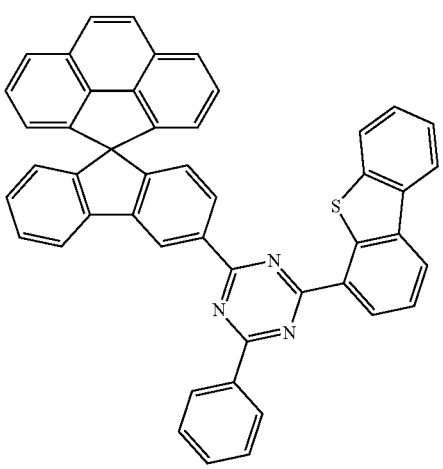
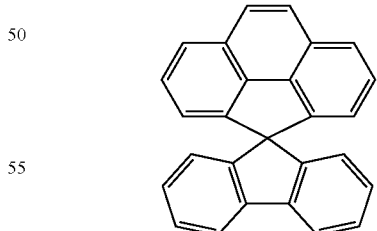
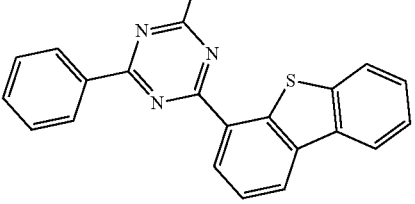

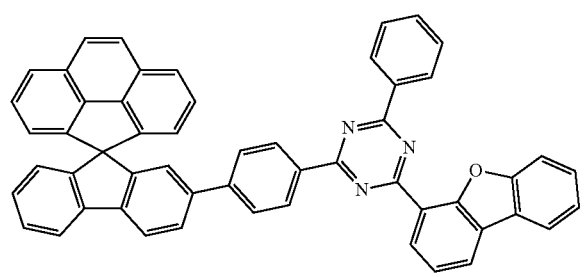
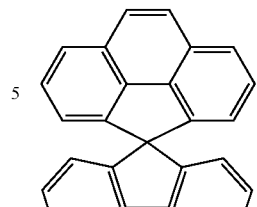
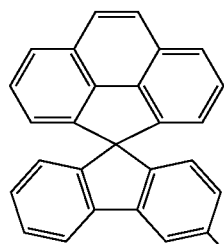
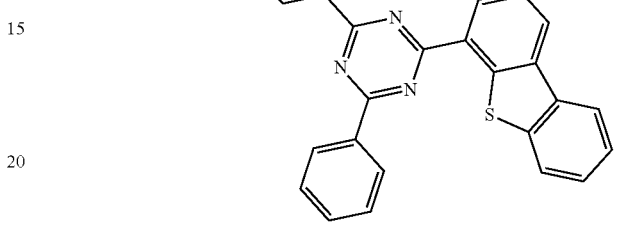
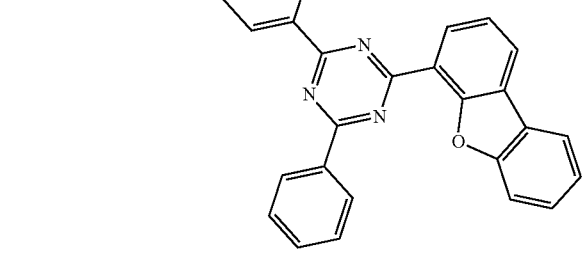
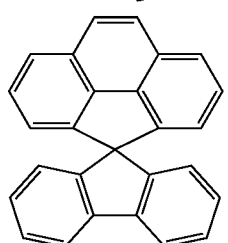
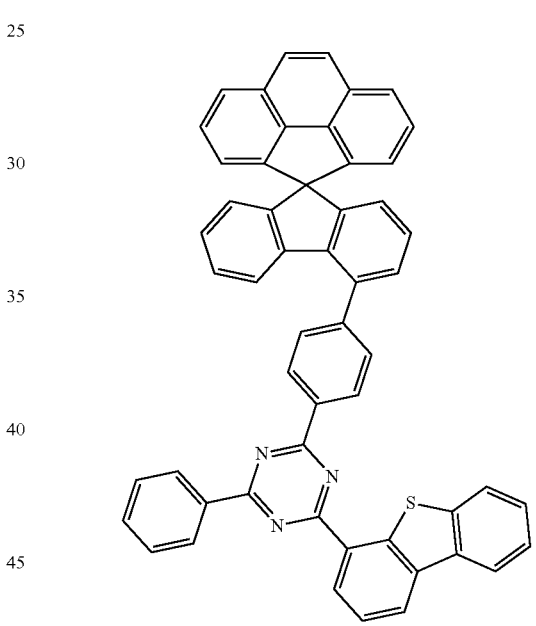
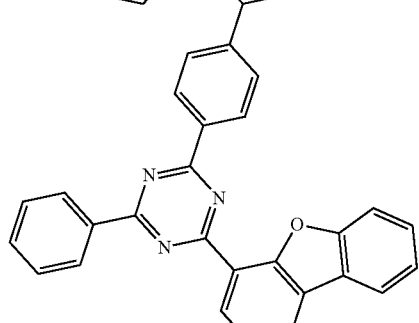
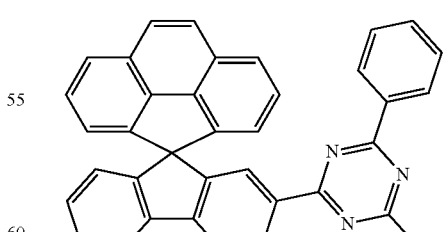
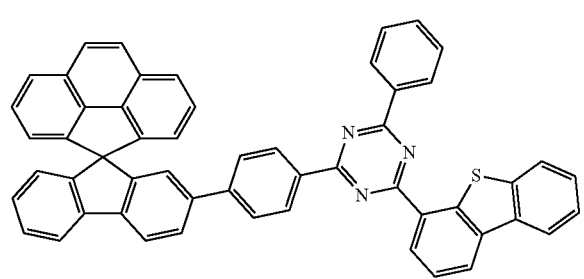

131
-continued
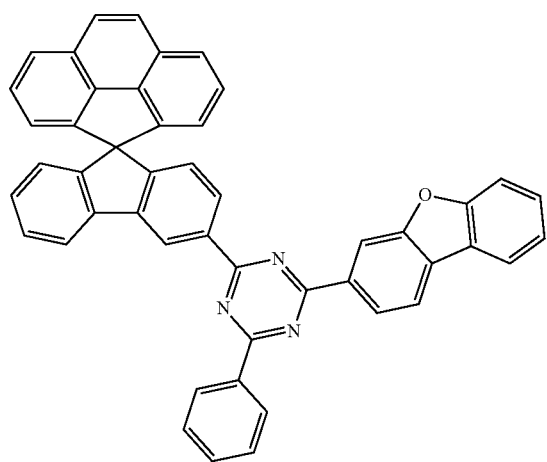
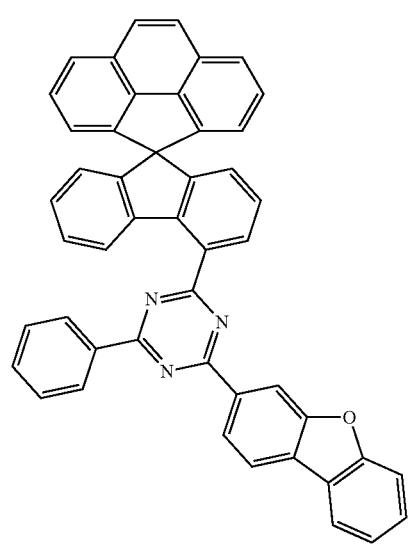
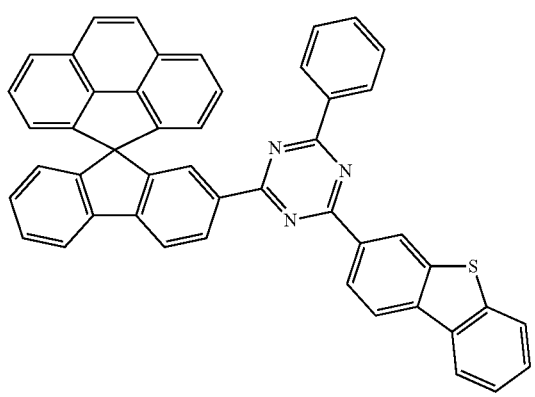
132
-continued
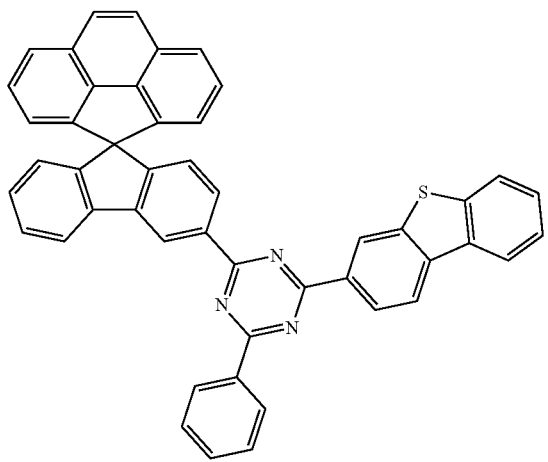
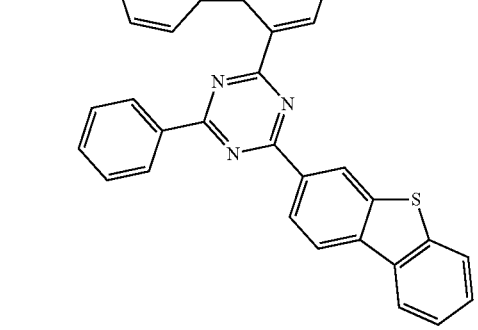
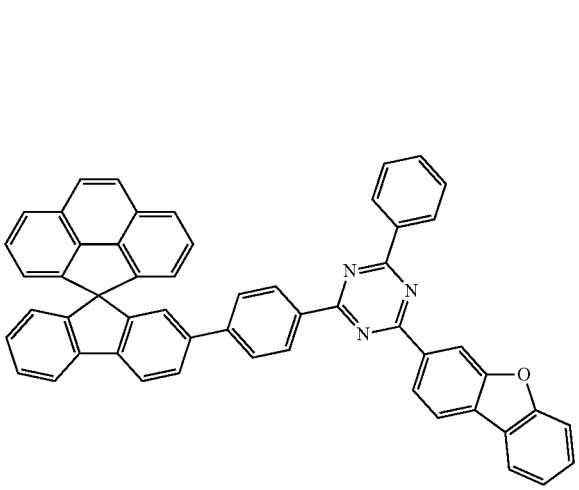

133
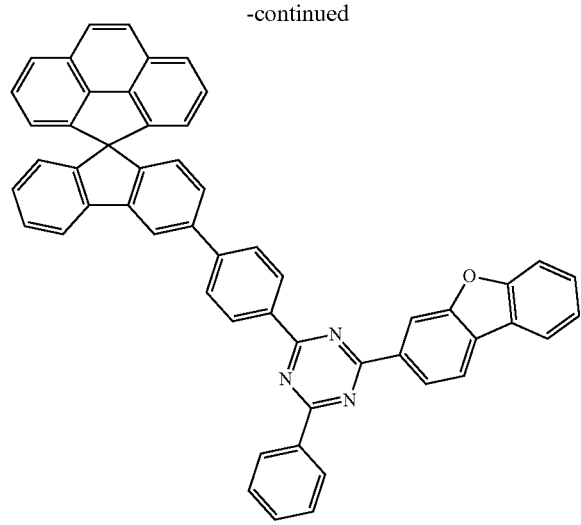
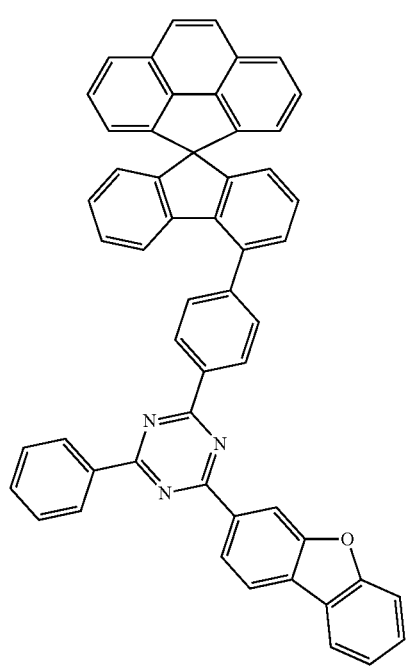
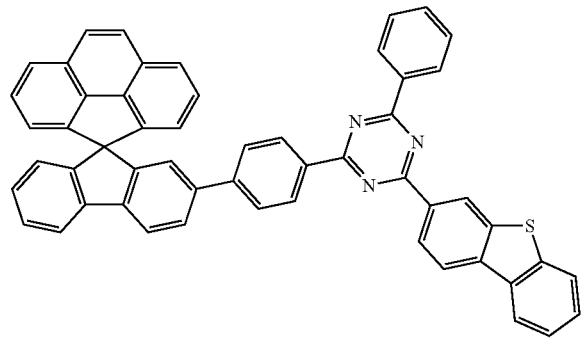
134
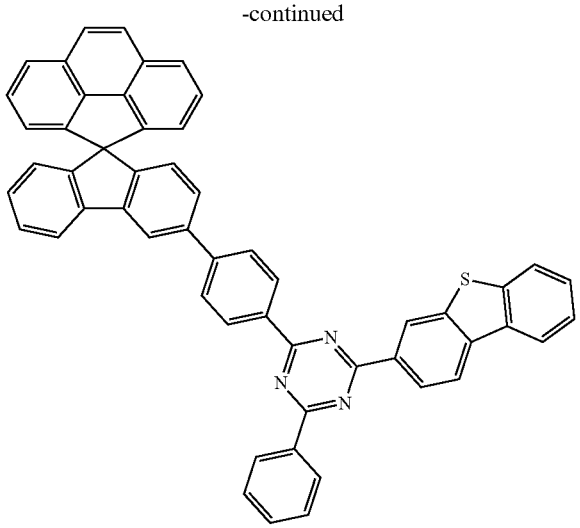
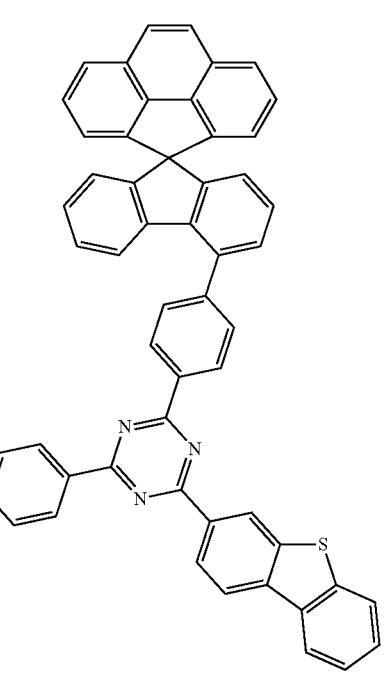
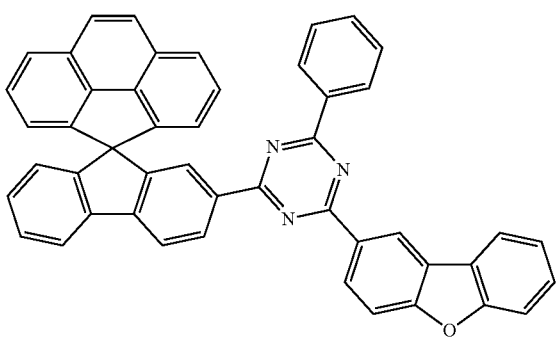

135
-continued
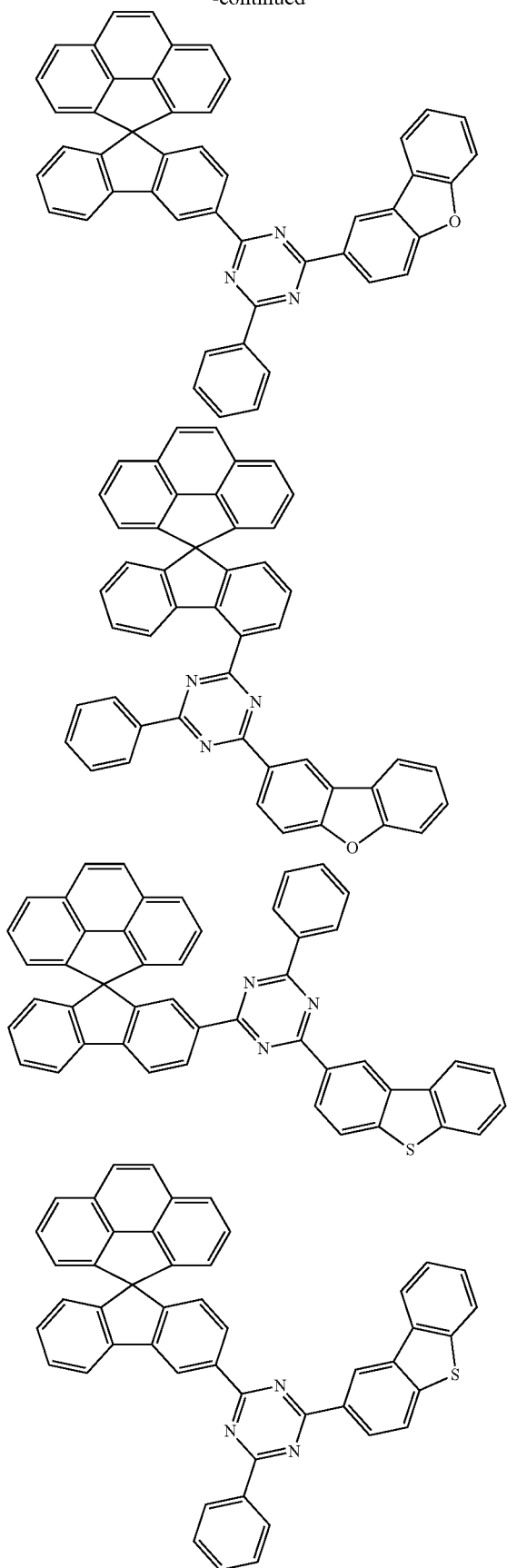
136
-continued
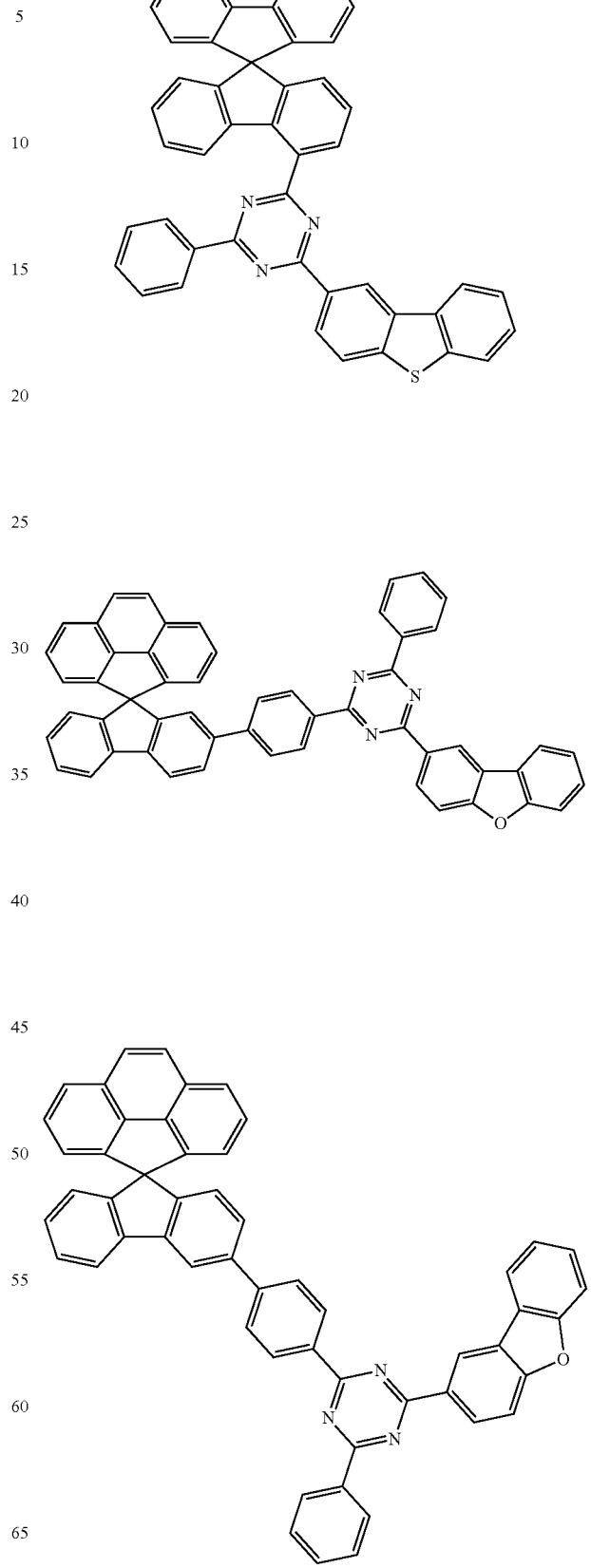

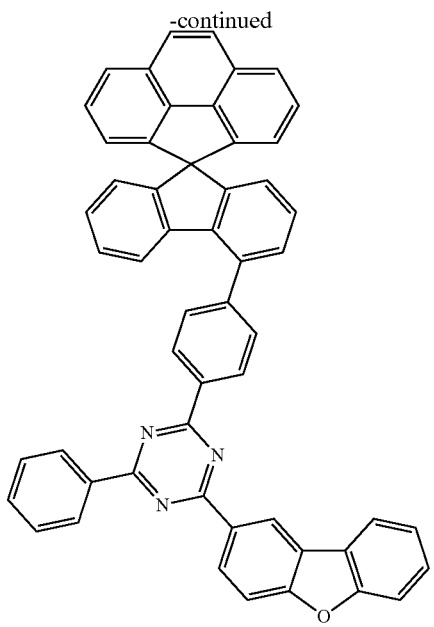
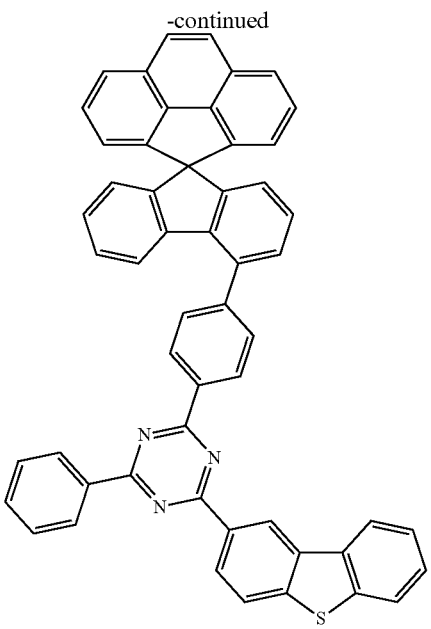
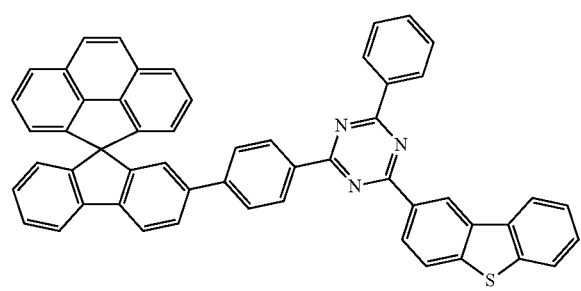
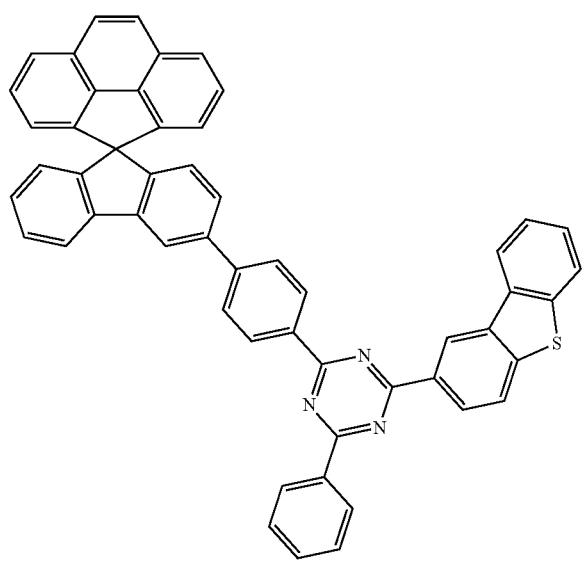
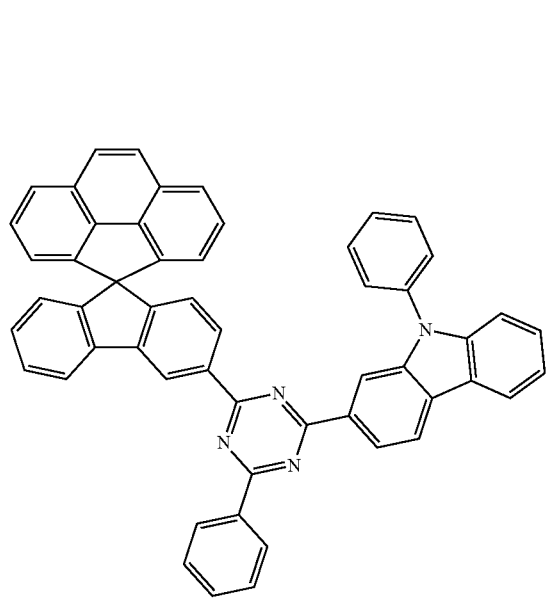

139
-continued
140
-continued
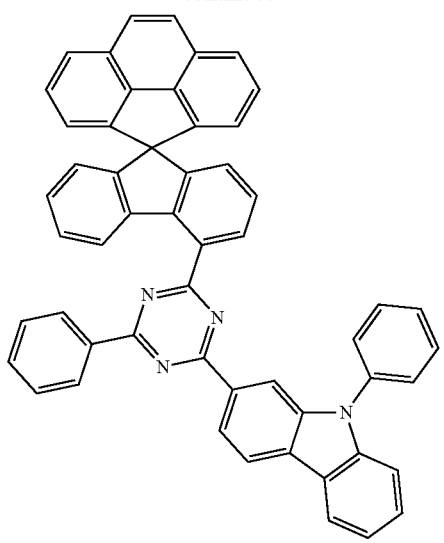
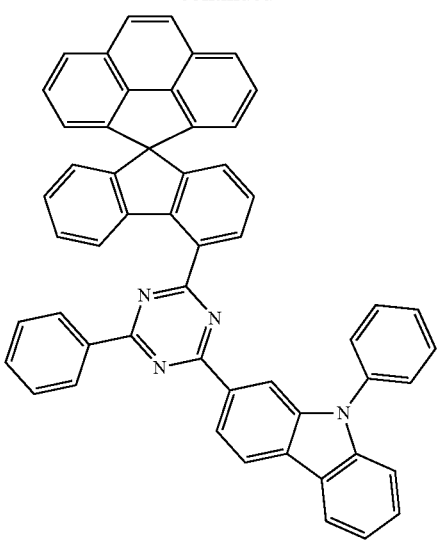
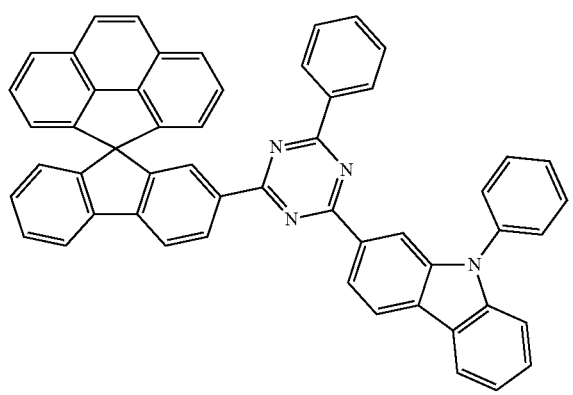
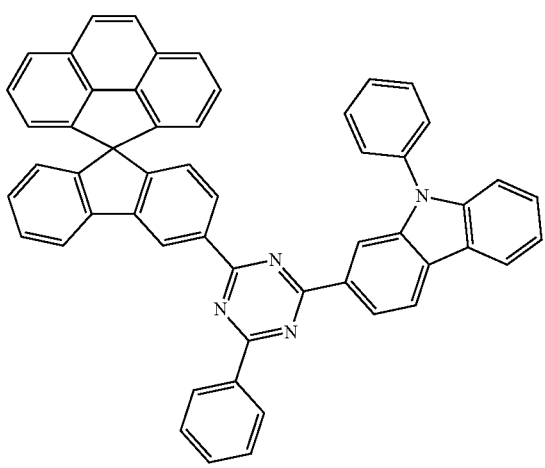
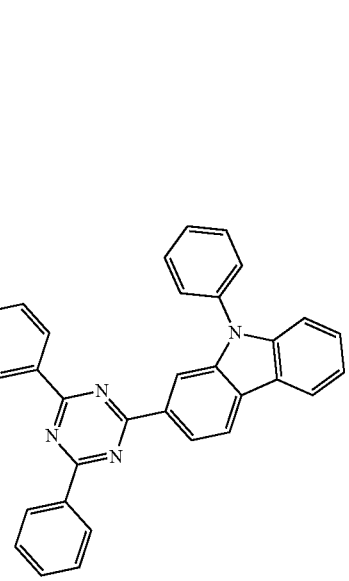

141
-continued
142
-continued
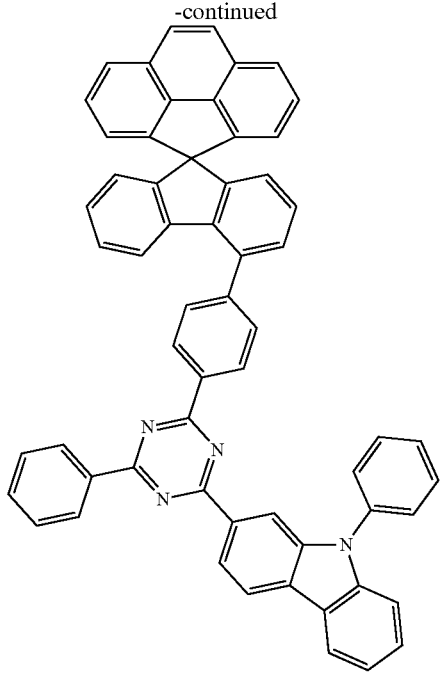
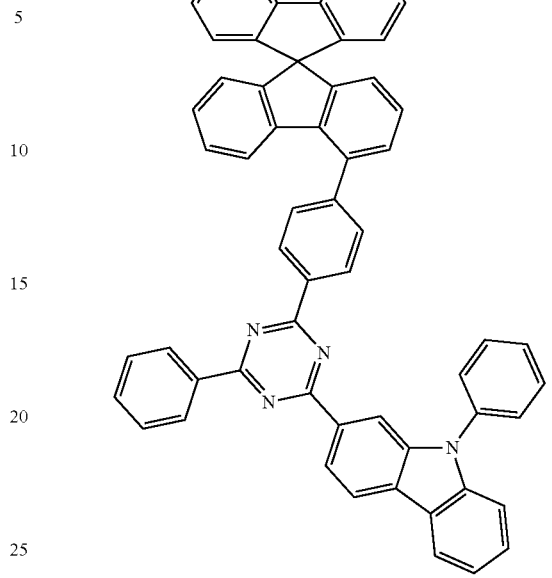
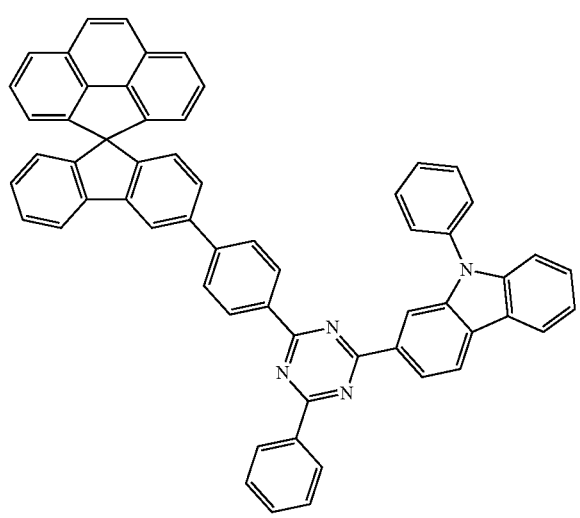
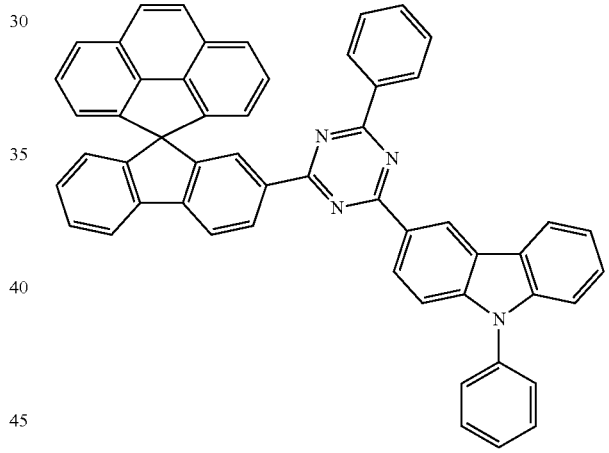
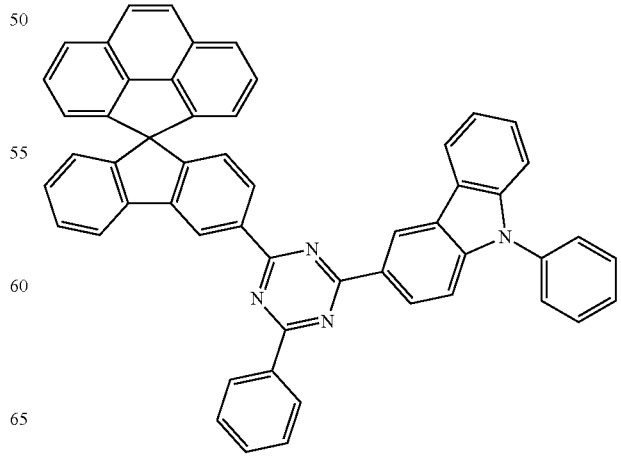

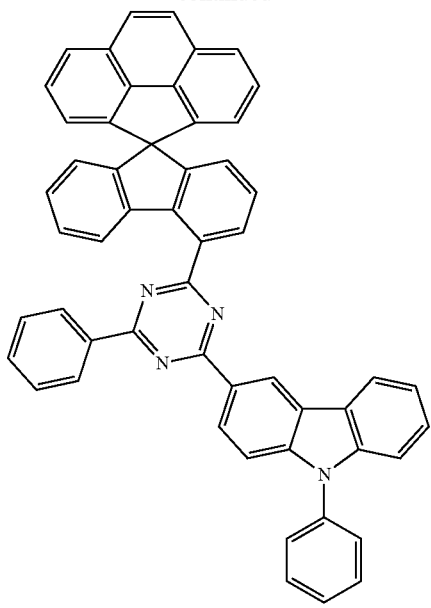
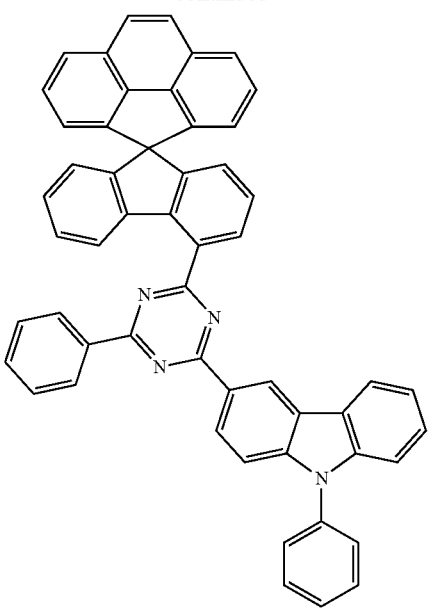
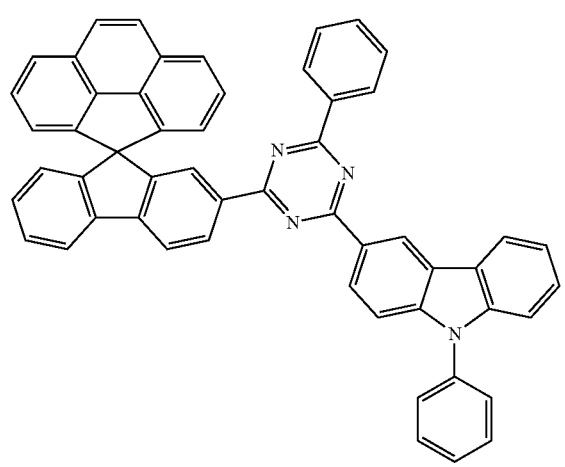
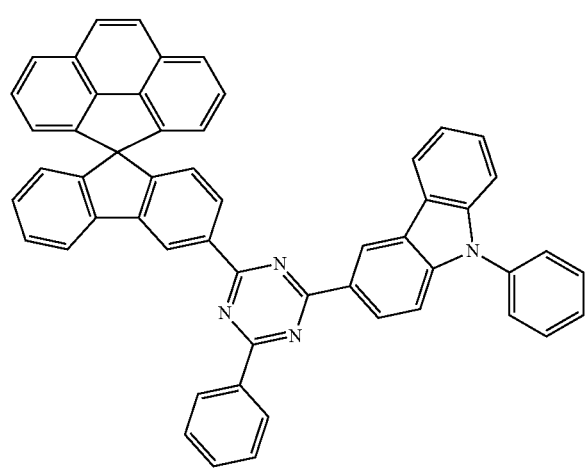
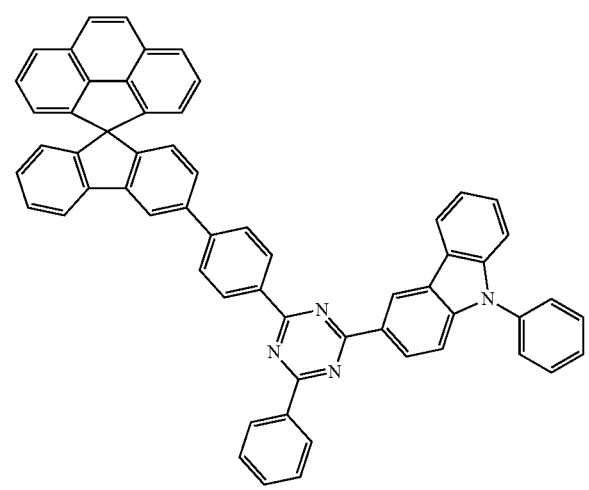

145
-continued
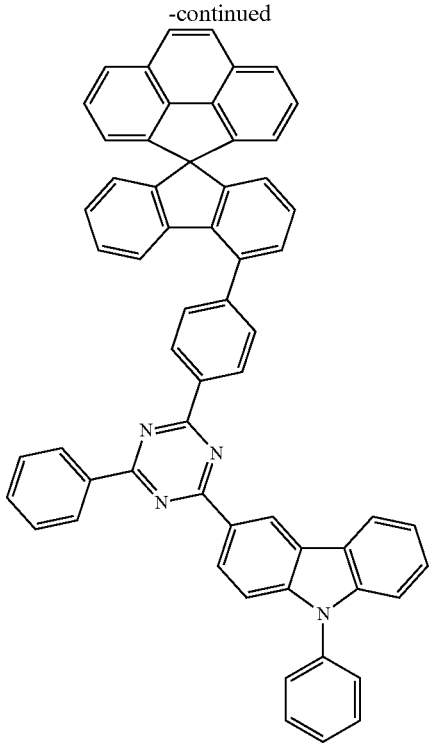
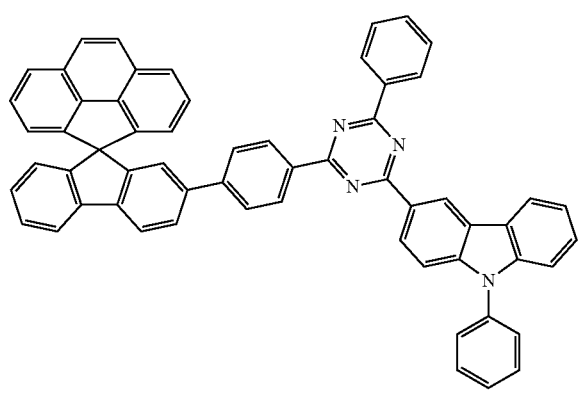
146
-continued
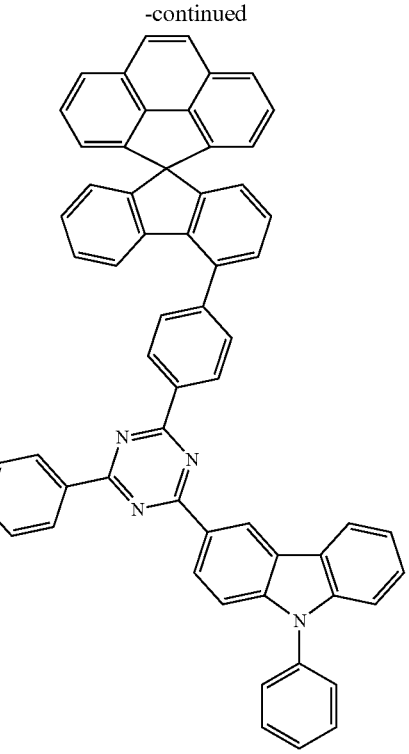
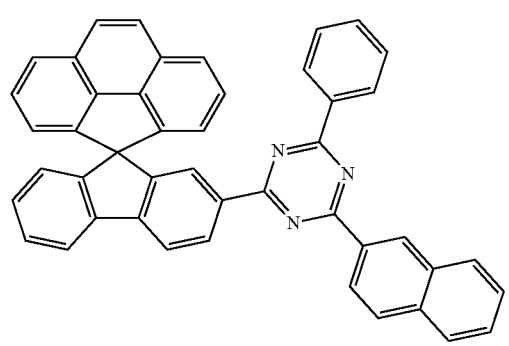
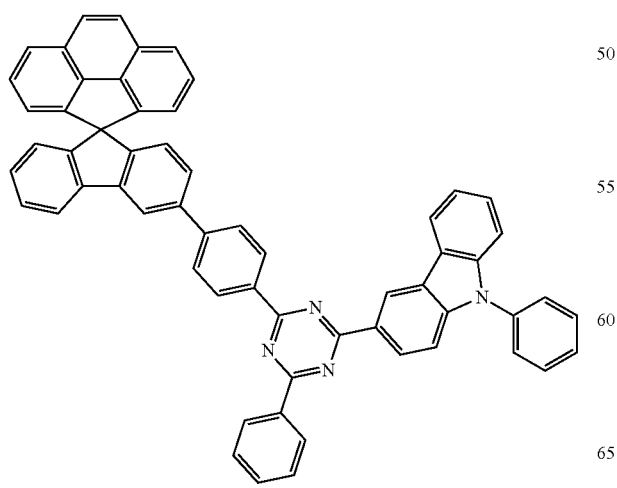
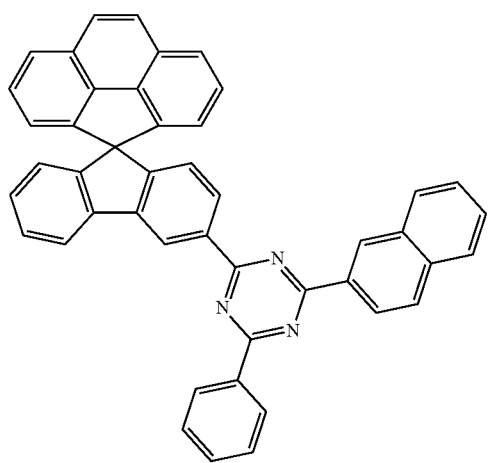

147
-continued
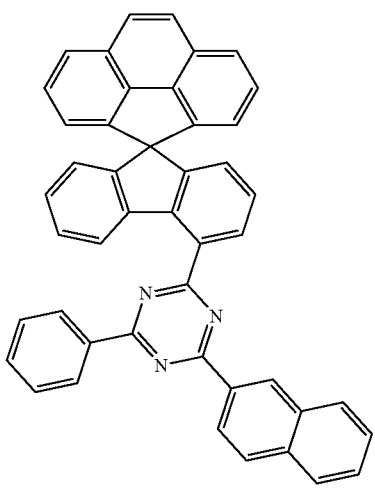
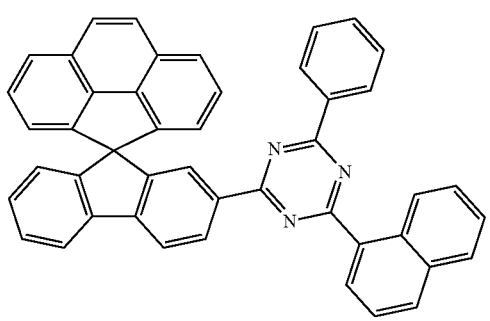
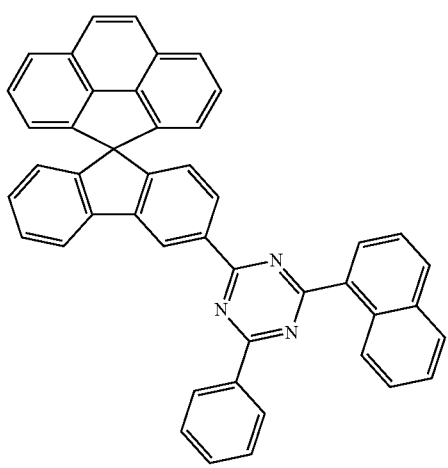
148
-continued
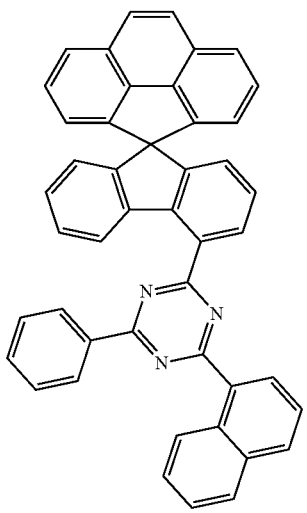
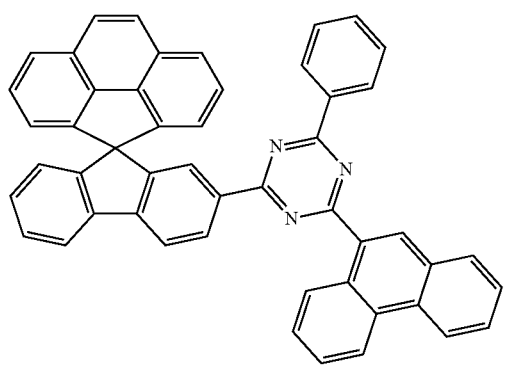
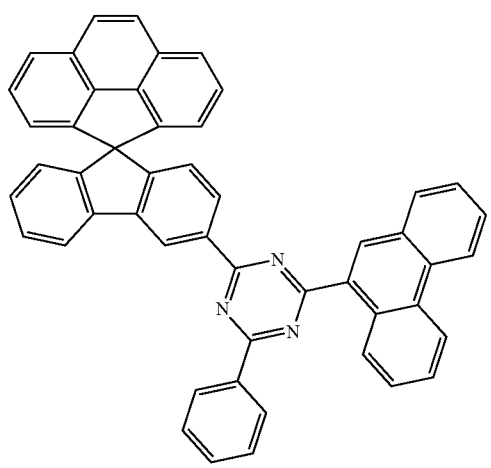

149
-continued
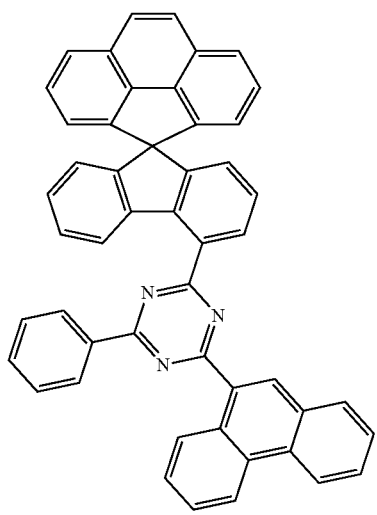
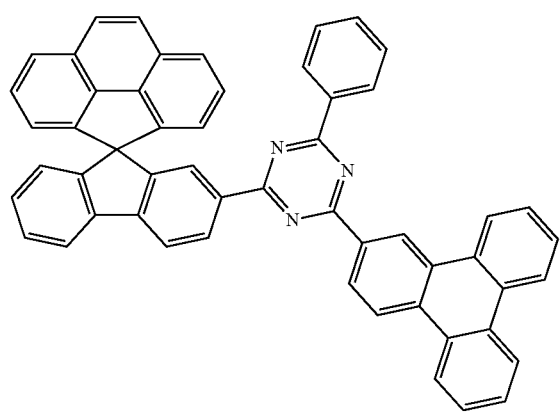
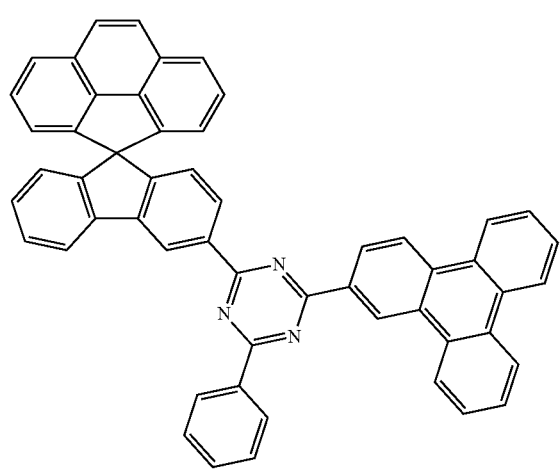
150
-continued
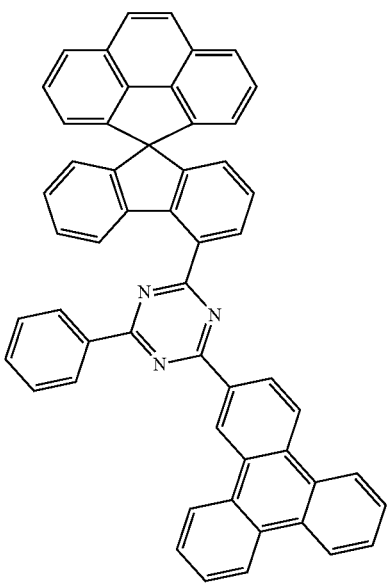
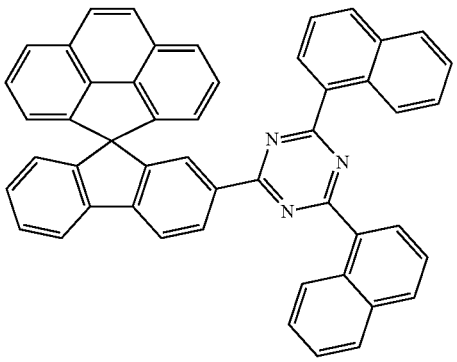
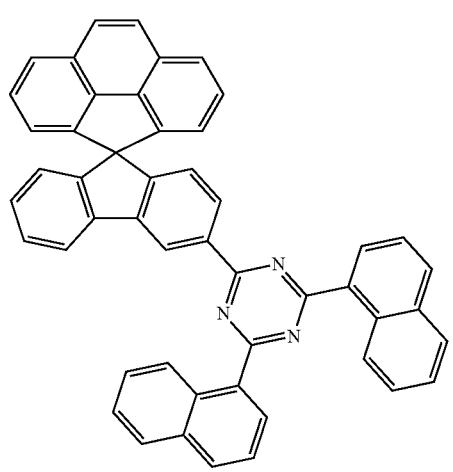

151
-continued
152
-continued
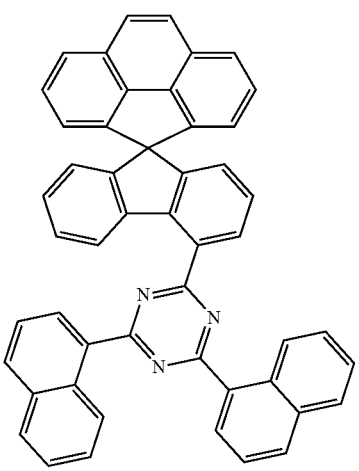
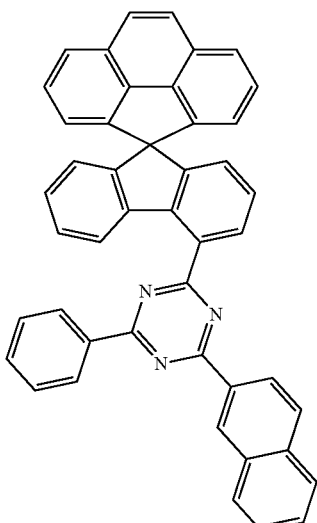
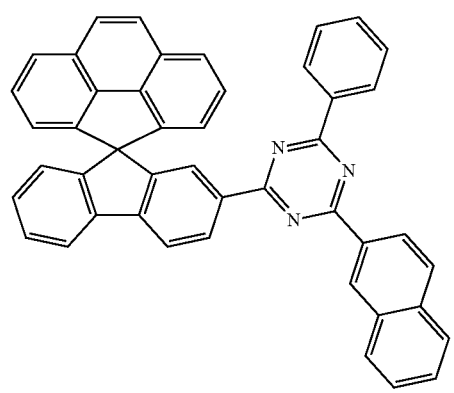
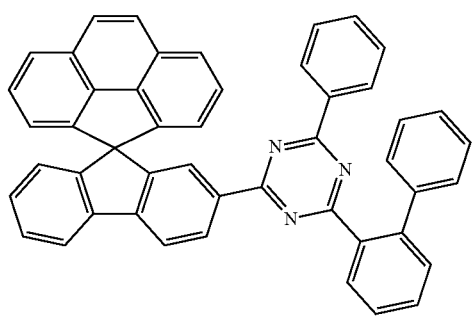
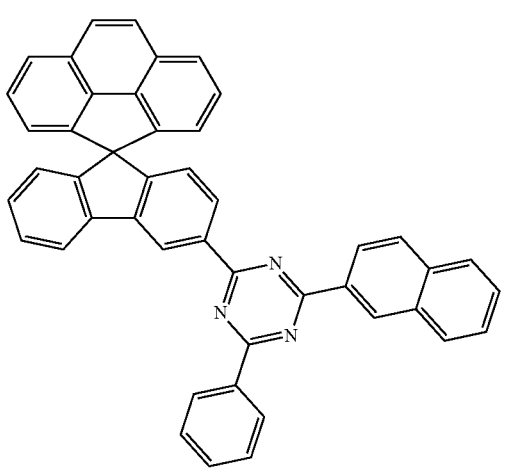
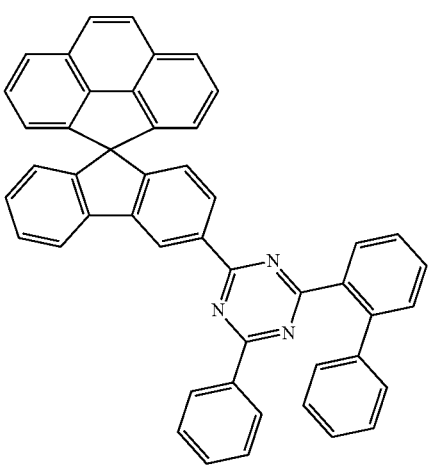

153
-continued
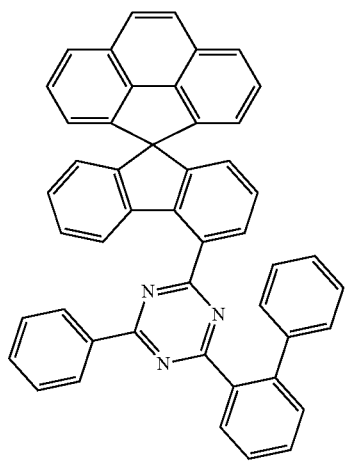
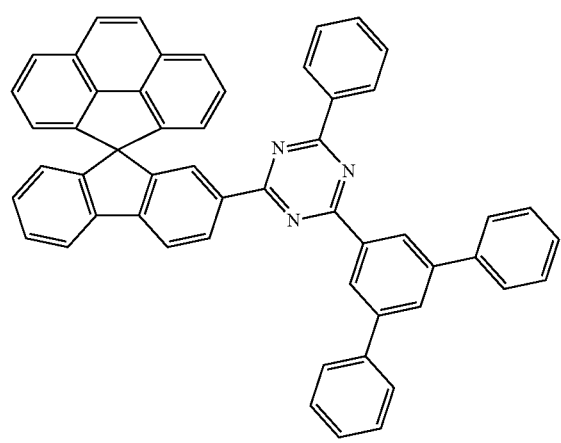
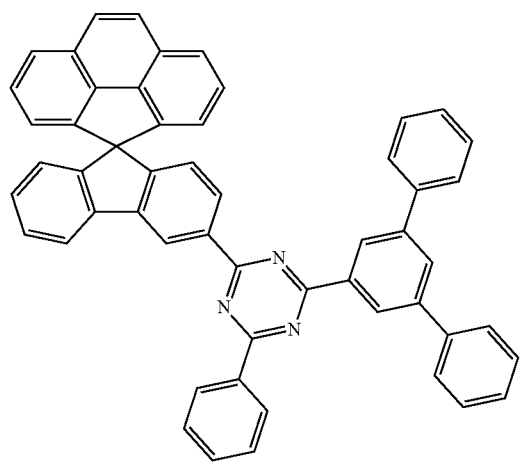
154
-continued
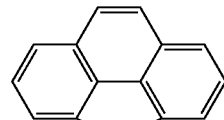
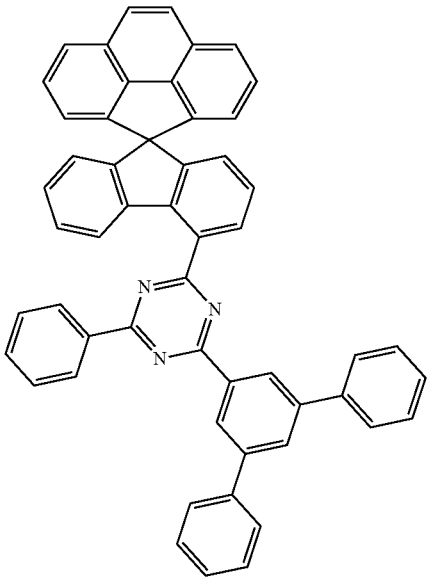
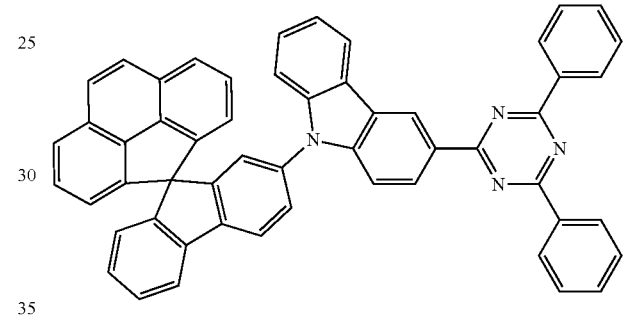
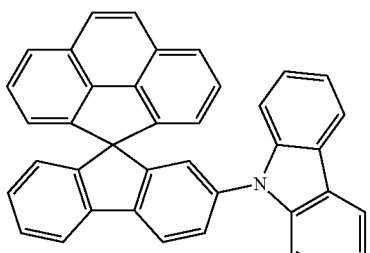
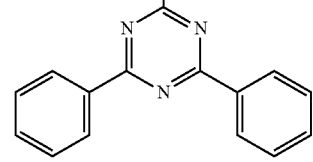
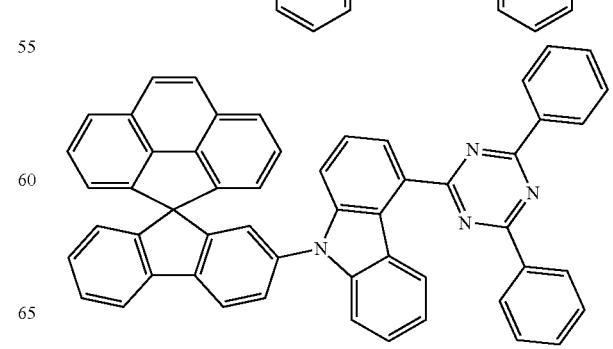

155
-continued

156
-continued

-continued
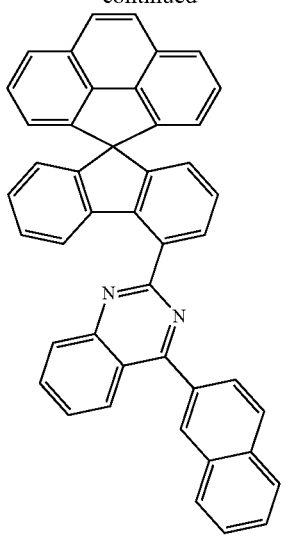
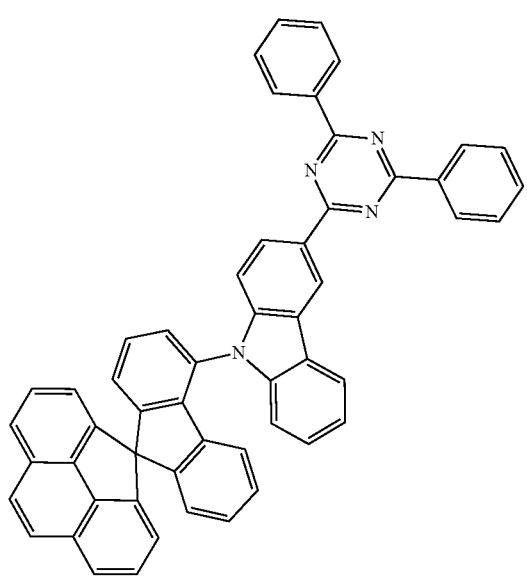
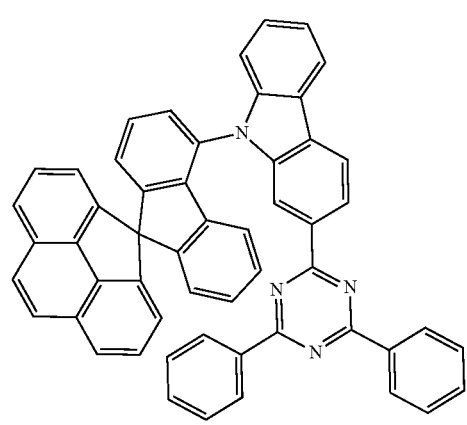
-continued
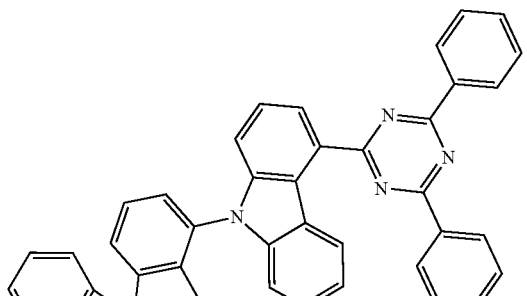
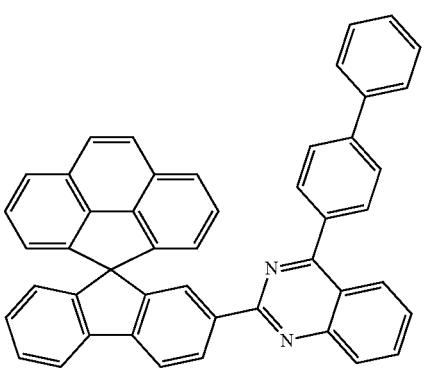
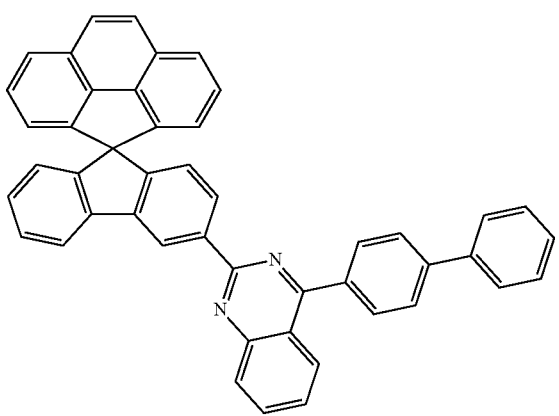

159
-continued
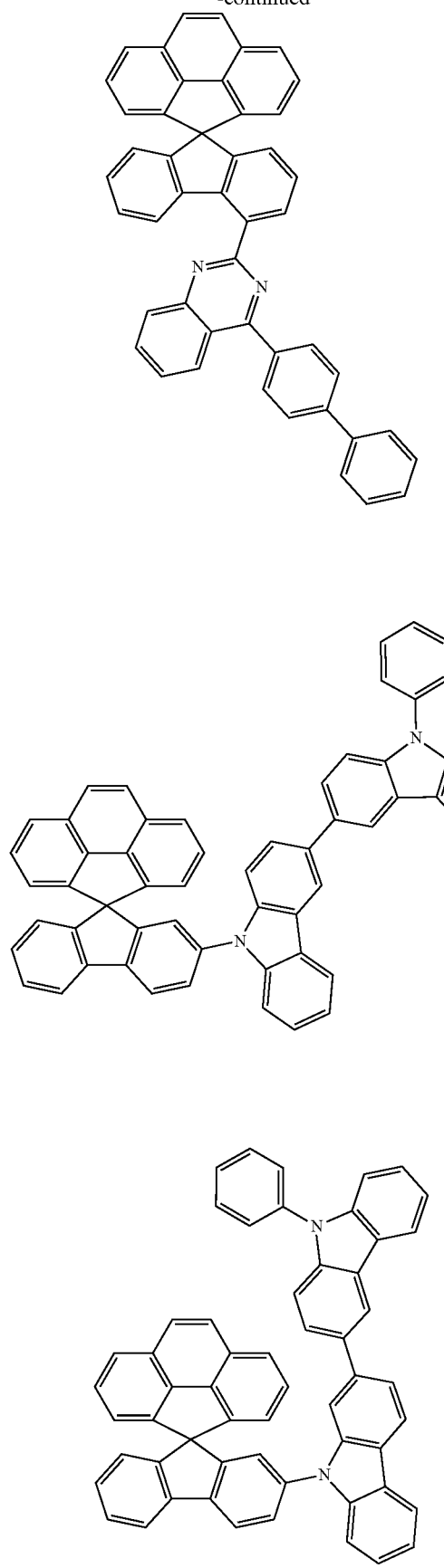
160
-continued
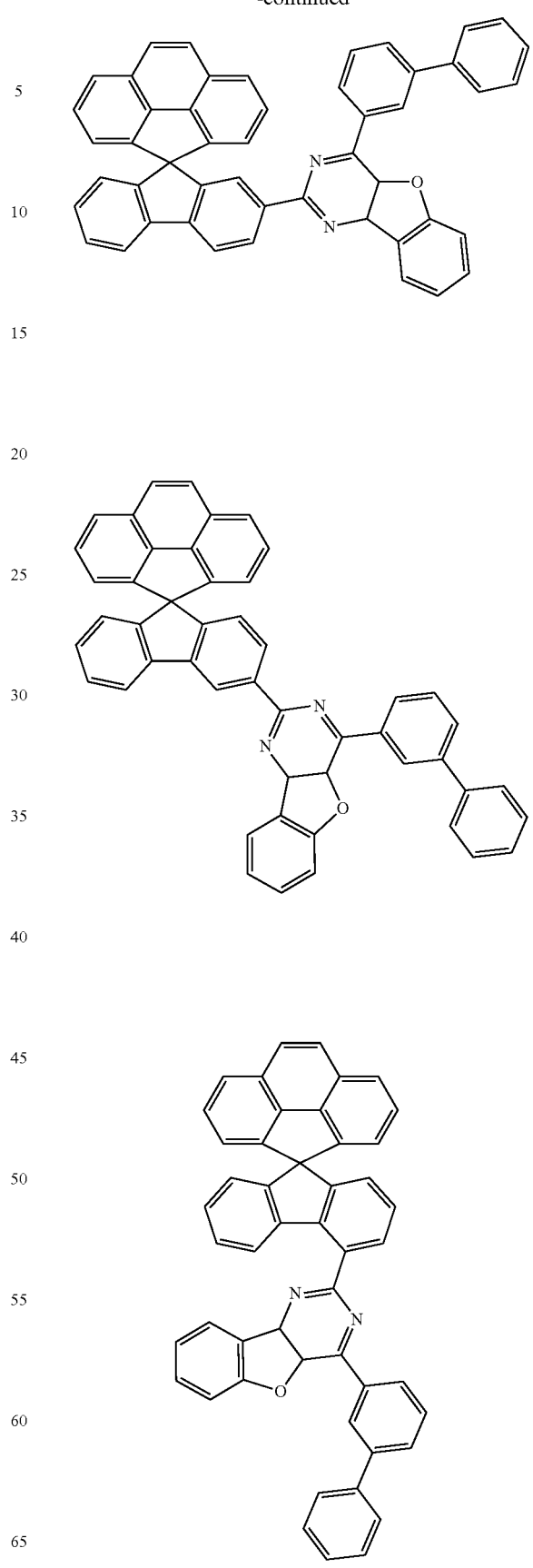

-continued
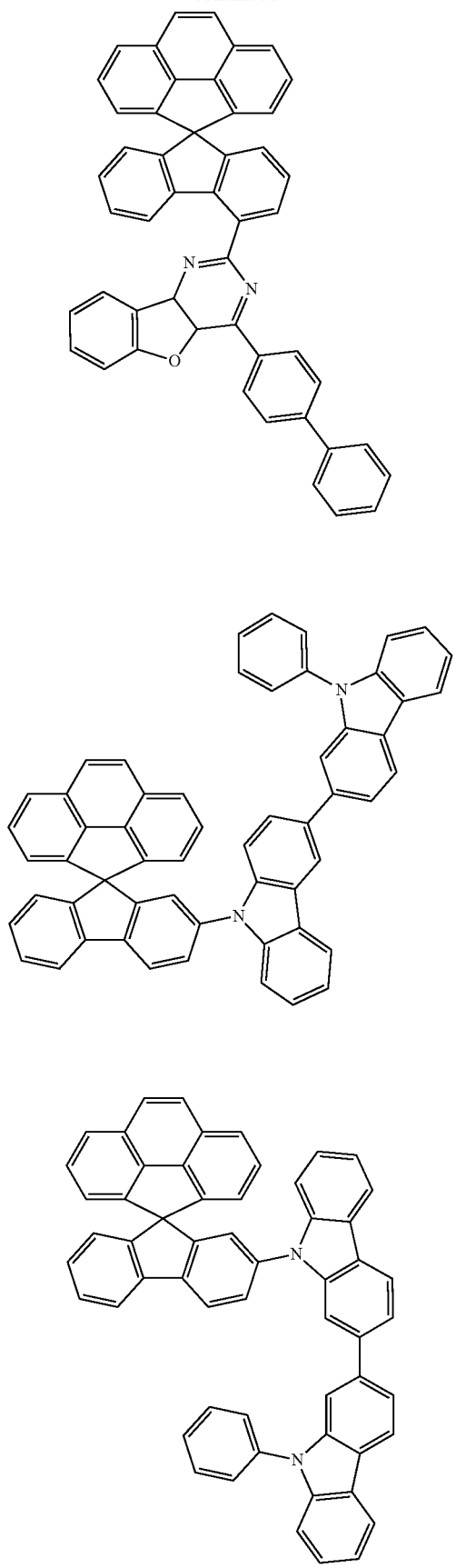
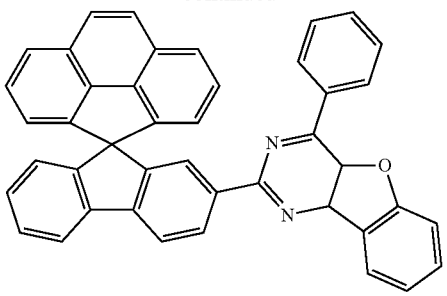
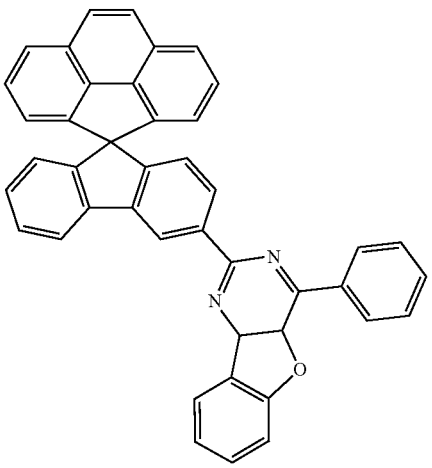
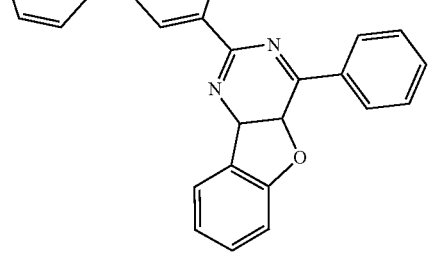
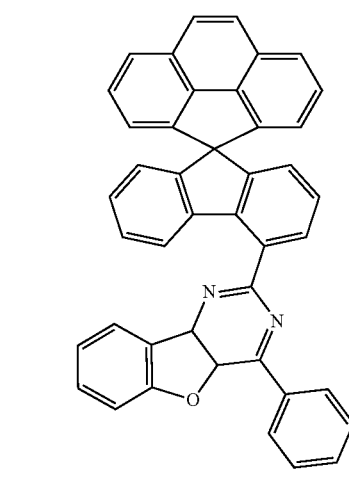
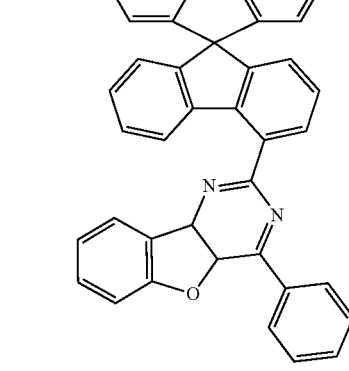

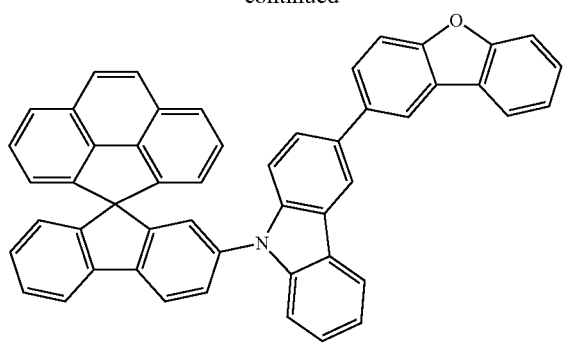
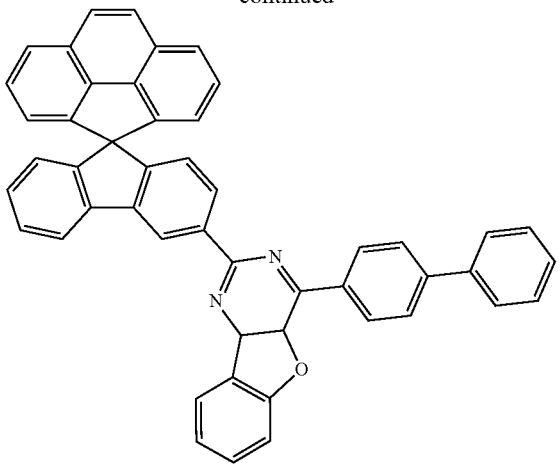
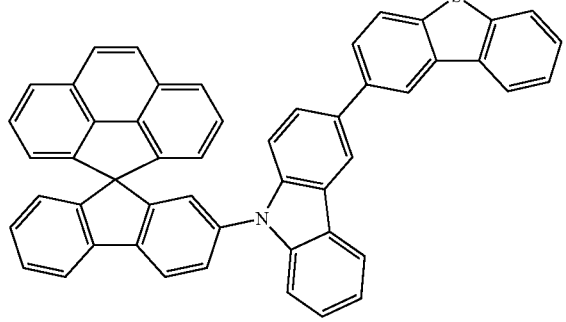
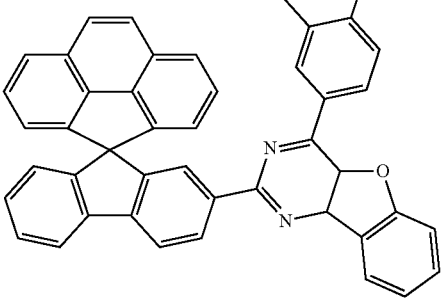
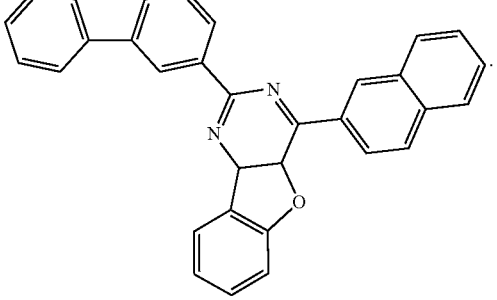
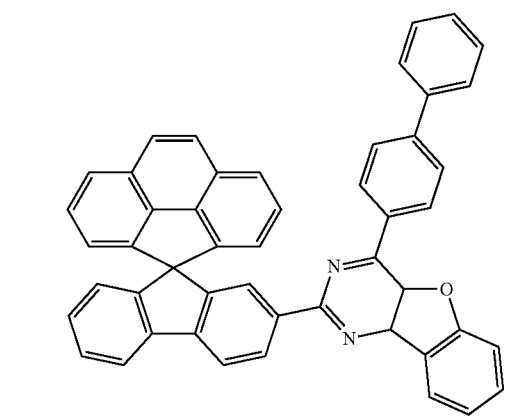
9. An organic light emitting device, comprising:
a first electrode;
a second electrode provided opposite to the first electrode; and
one or more organic material layers provided between the first electrode and the second electrode, wherein one or more layers of the organic material layers comprise the compound of claim 1.
* * * * *